US006703219B1

(12) United States Patent
Potempa et al.

(10) Patent No.: US 6,703,219 B1
(45) Date of Patent: *Mar. 9, 2004

(54) MUTANT PROTEIN AND METHODS AND MATERIALS FOR MAKING AND USING IT

(75) Inventors: Lawrence A. Potempa, Deerfield, IL (US); Hans H. Liao, Oakville (CA); Becky L. Crump, Evanston, IL (US)

(73) Assignee: Immtech International Inc., Vernon Hills, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/274,454

(22) Filed: Mar. 22, 1999

Related U.S. Application Data

(60) Division of application No. 09/212,850, filed on Dec. 16, 1998, which is a division of application No. 08/480,270, filed on Jun. 7, 1995, now Pat. No. 5,874,238, which is a division of application No. 08/296,545, filed on Aug. 26, 1994, now abandoned, which is a continuation-in-part of application No. 08/023,952, filed on Feb. 26, 1993, now abandoned.

(51) Int. Cl.[7] ................................................ C12P 21/06
(52) U.S. Cl. ........................ 435/69.1; 530/350; 530/380
(58) Field of Search ................................ 530/380, 350; 435/69.1

(56) References Cited

U.S. PATENT DOCUMENTS

| | | | |
|---|---|---|---|
| 5,272,258 A | 12/1993 | Siegel et al. | 530/388.25 |
| 5,283,238 A | 2/1994 | Potempa et al. | 514/12 |
| 5,405,832 A | 4/1995 | Potempa | 514/12 |
| 5,474,904 A | 12/1995 | Potempa et al. | 435/7.23 |
| 5,547,931 A | 8/1996 | Potempa | 514/2 |
| 5,585,349 A | 12/1996 | Potempa | 514/12 |
| 5,593,897 A | 1/1997 | Potempa et al. | 436/507 |
| 5,874,238 A | 2/1999 | Potempa et al. | 435/69.1 |

FOREIGN PATENT DOCUMENTS

| | | |
|---|---|---|
| WO | WO 89/09628 | 10/1989 |
| WO | WO 91/00872 | 1/1991 |
| WO | WO 93/10799 | 6/1993 |
| WO | WO 93/10800 | 6/1993 |
| WO | WO 93/21944 | 11/1993 |

OTHER PUBLICATIONS

Nguyen et al. The amino acid sequence of Limulus C–reactive protein: Evidence of polymorphism. J. Biol. Chem. 267(22): 10456–10465, 1986.*

Agrawal et al. Probing the Phosphocholine–binding site of human C–reactive protein by site–directed mutagenesis. J. Biol. Chem. 267(35): 25352–25358, 1992.*

(List continued on next page.)

Primary Examiner—Gabrielle Bugaisky
Assistant Examiner—Laurie Mayes
(74) Attorney, Agent, or Firm—Sheridan Ross P.C.

(57) ABSTRACT

The invention provides a mutant protein which has the same amino acid sequence as an unmutated C-reactive protein (CRP) subunit or an unmutated preCRP, except that at least one amino acid of the unmutated CRP subunit or unmutated preCRP has been deleted, at least one amino acid of the unmutated CRP subunit or unmutated preCRP has been replaced by another amino acid, at least one amino acid has been added to the unmutated CRP subunit or preCRP, or a combination of such changes has been made. The amino acid(s) added, deleted and/or replaced are chosen so that the mutant protein is less likely to form covalently cross-linked aggregates than the unmutated CRP subunit or unmutated preCRP. The mutant protein also exhibits at least one of the biological activities of modified-CRP. The invention also provides DNA molecules coding for the mutant proteins of the invention, vectors for expressing the mutant proteins, host cells which have been transformed so that they can express the mutant proteins, and a method of producing the mutant proteins of the invention comprising culturing the transformed host cells. Finally, the invention provides methods and materials for using the mutant proteins.

43 Claims, 24 Drawing Sheets

OTHER PUBLICATIONS

Agrawal et al., *J. Biol. Chem.*, 267:25352–25358 (1992).
Nguyen et al., *J. Biol. Chem.*, 261:10456–10465 (1986).
Agrawal et al., *FASEBJ.*, 6:1427a (1992).
Arcone et al., *Nucleic Acids Res.*, 16:3195–3207 (1988).
Bray et al., *Clin. Immunol. Newsletter*, 8:137–140 (1987).
Chu et al., *Proc. Amer. Acad. Cancer Res.*, 30 (1989).
Chu et al., *Proc. Amer. Acad. Cancer Res.*, 28:334a (1987).
Chu et al., *Proc. Amer. Acad. Cancer Res.*, 29:371a (1988).
Chudwin et al., *J. Allergy Clin. Immunol.*, 77:216a (1986).
Ciliberto et al., *Nucleic Acids Res.*, 15:5895 (1987).
Ciliberto et al., *The EMBO J.*, 6:4017–4022 (1987).
Dayhoff et al., in *Atlas of Protein Sequence and Structure*, 5(3):345–352 (Dayhoff ed. 1978).
DuClos et al., *J. Immunol.*, 141:4266–4270 (1988).
DuClos et al., *J. Immunol.*, 146:1220–1225 (1991).
DuClos et al., *J. Immunol.*, 145:3869–75 (1990).
Floyd–Smith et al., *Immunogenetics*, 24:171–76 (1986).
Ganapathi et al., *J. Immunol.*, 147:1261–65 (1991).
Ganapathi et al., *Clin Res.*, 36:879A (1988).
Ganter et al., *The EMBO J.*, 3773–79 (1989).
Gewurz et al., *Adv. Int. Med.*, 27:345–372 (1982).
Goldberger et al., *J. Immunol.*, 138:3967–71 (1987).
Goldman et al., *J. Biol. Chem.*, 262:2363–68 (1987).
Gotschlich, *Ann. N.Y. Acad. Sci.*, 557:9–18 (1989).
Horowitz et al., *J. Immunol.*, 138:2598–2603 (1987).
Hu et al., *Biochem.*, 25:7834–39 (1986).
Hu et al., *Fed. Proc.*, 46:2107 (1987).
Hu et al., *J. Biol. Chem.*, 263:1500–1504 (1988).
Kaplan et al., *J. Immunol.*, 112:2135:2147 (1974).
Kilpatrick and Volanakis, *Immunol. Res.*, 10:43–53 (1991).
Kushner, *Prot. Biol. Fluids, Proceedings of the 34th Colloquim*, 259–61 (1986).
Kushner, *Ann. N.Y. Acad. Sci.*, 389:39–48 (1982).
Lei et al., *J. Biol. Chem.*, 260:13377–83 (1985).
Mackiewicz et al., *J. Immunol.*, 146:3032–37 (1991).
Mantzouranis et al., *Ped. Res.*, 18:260a (1984).
Marston, in *DNA Cloning*, vol. III, pp. 59–88 (Glover ed. 1987).
Mold et al., *J. Exp. Med.*, 154:1703–1708 (1981).
Mortensen et al., *J. Immunol.*, 150:216a (1993).
Nakayama et al., *Clin. Exp. Immunol.*, 54:319–326 (1983).
Narkates et al., *Ann. N.Y. Acad. Sci.*, 389:172–182 (1982).
Ollivier et al., *Protides Biol. Fluids*, 34:271–74 (1986).
Pepys et al., *Adv. Immunol.*, 34:141–212 (1983).
Potempa et al., *Mol. Immunol.*, 20:1165–75 (1983).
Potempa et al., *FASEB J.*, 2:731a (1988).
Potempa et al. *Mol. Immunol.*, 24:531–41 (1987).
Potempa et al., *Proc. Amer. Acad. Cancer Res.*, 28:344a (1987).
Potempa et al., *Inflammation*, 12:391–405 (1988).
Potempa et al., *Protides Biol. Fluids*, 34:287–290 (1986).
Rees et al., *Fed. Proc.*, 45:263a (1986).
Robey et al., *J. Biol. Chem.*, 259:7311–7316 (1984).
Robey et al., *J. Exp. Med.*, 161:1344–56 (1985).
Samols and Hu, *Protides Biol. Fluids*, 34:263–66 (1986).
Samols et al., *Biochem. J.*, 227:759–65 (1985).
Shepard et al., *Clin. Exp. Immunol.*, 63:718–27 (1986).
Siegel et al., *J. Exp. Med.*, 140:631–47 (1974).
Siegel et al., *J. Exp. Med.*, 142:709–21 (1975).
Syin et al., *J. Biol. Chem.*, 261:5473–79 (1986).
Tatsumi et al., *Clinica Chimica Acta*, 172:85–92 (1988).
Taylor et al., *J. Immunol.*, 145:2507–13 (1990).
Tenchini et al., *Inflammation*, 16:93–99 (1992).
Tillett and Francis, *J. Exp. Med.*, 52:561–71 (1930).
Tucci et al., *J. Immunol.*, 131:2416–2419 (1983).
Vigo, *J. Biol. Chem.*, 260:3418–3422 (1985).
Volanakis et al., *J. Immunol.*,4113:9–17 (1974).
Volanakis et al., *Defense Molecules*, pp. 161–175 (1990).
Whitehead et al., *Science*, 221:69–71 (1983).
Whitehead et al., *Biochem. J.*, 266:283–90 (1990).
Woo et al., *J. Biol. Chem.*, 260:13384–88 (1985).
Xia et al., *FASEB J.*, 6:1344a (1992).
Xia et al., *FASEB J.*, 5:A1628 (1991).
Ying et al., *J. Immunol.*, 143:221–228 (1989).
Ying et al., *Molec. Immunol.*, 29:677–687 (1992).
Ying et al., *Immunol.*, 76:324–330 (1992).
Zeller et al., *Fed. Proc.*, 46:1033a (1987).
Supplementary European Search Report (one page).

* cited by examiner

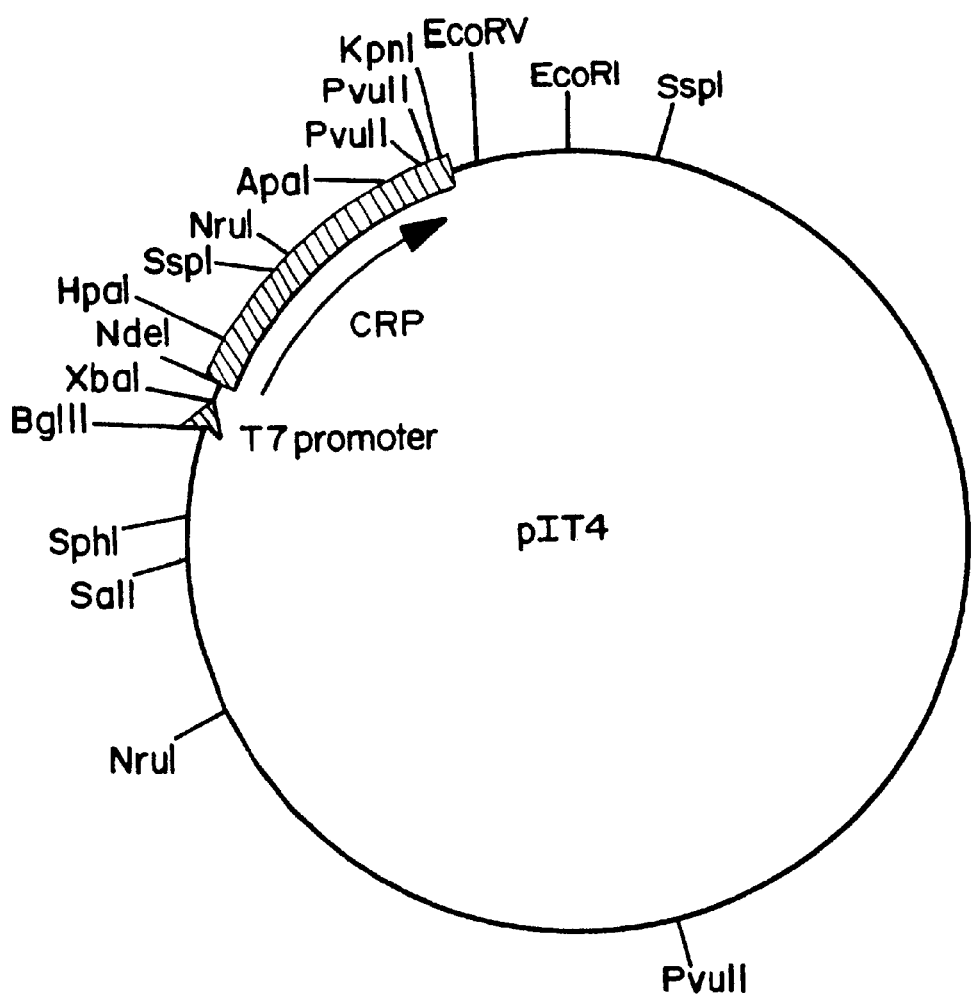
FIG. IB

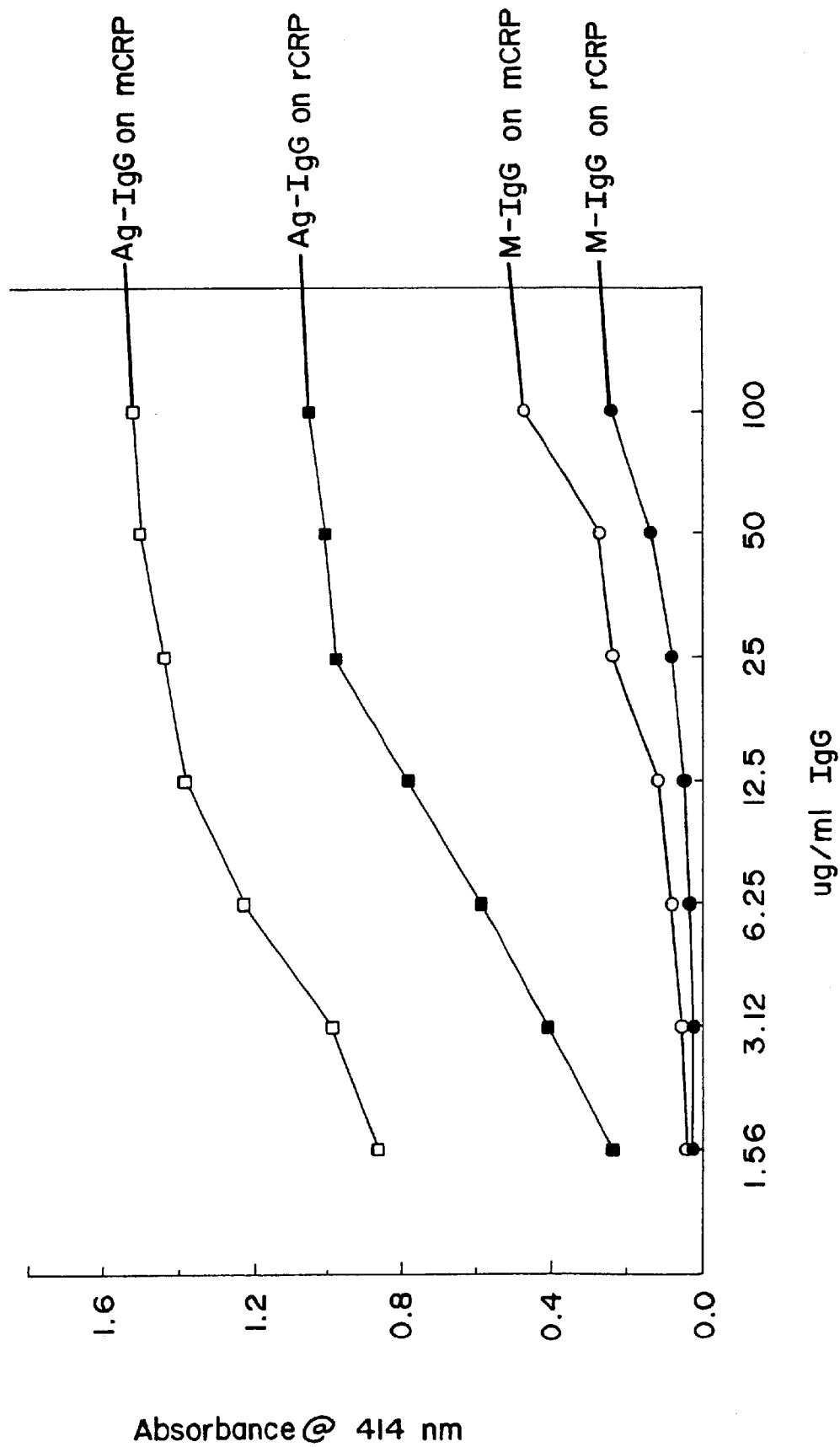

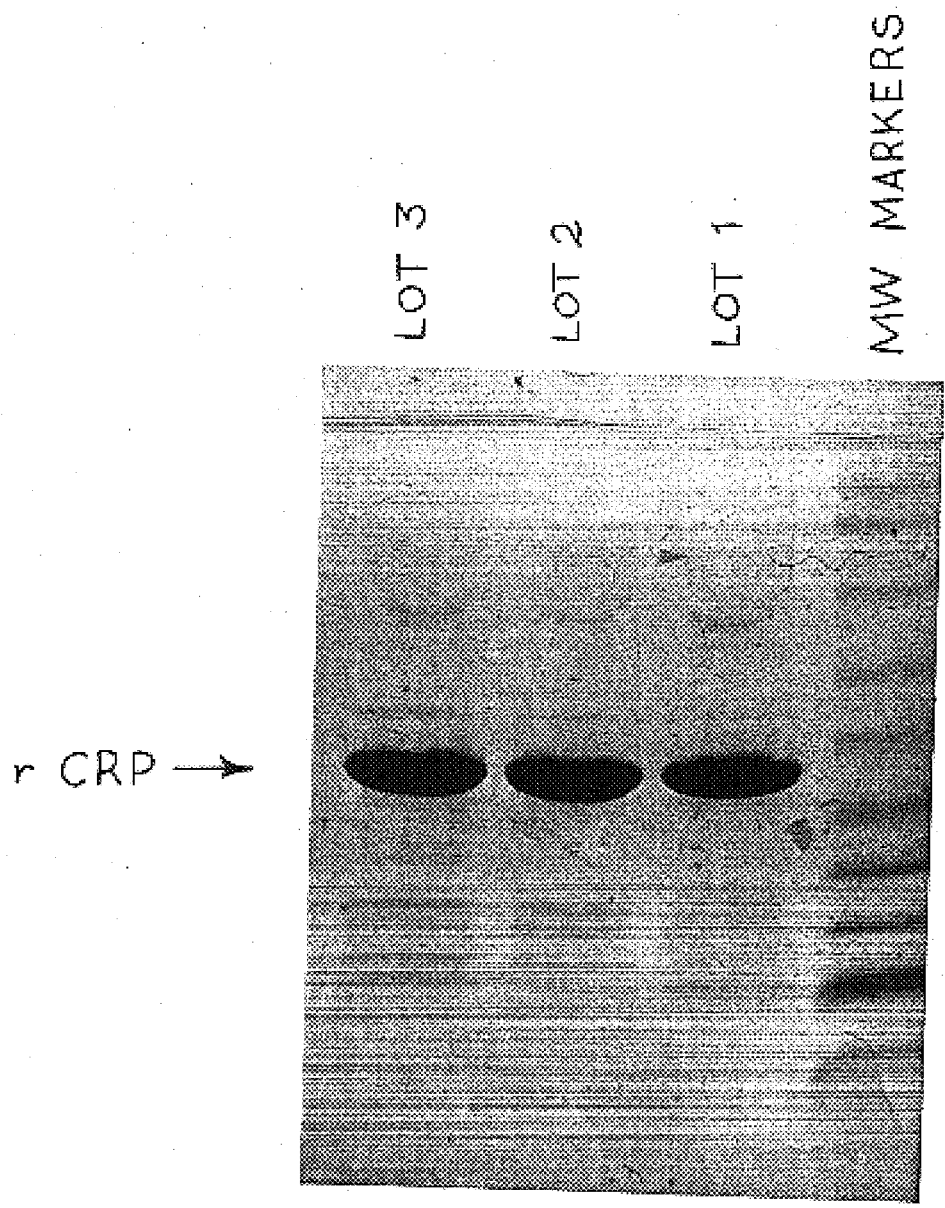

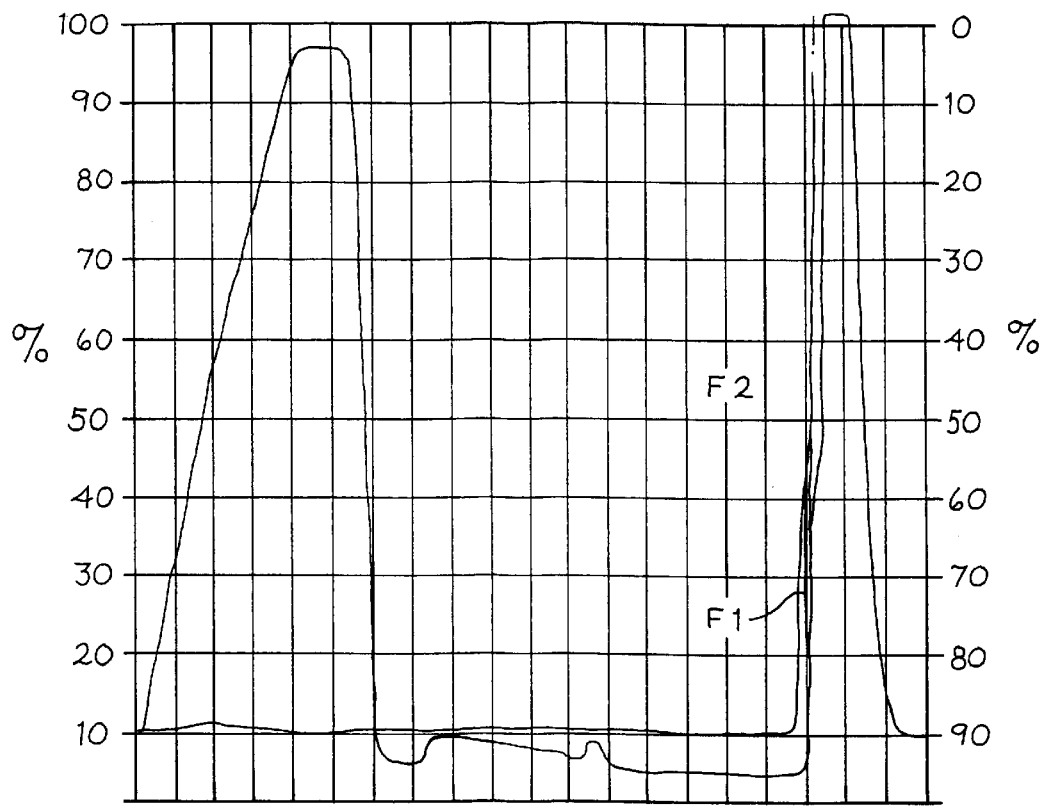
FIGURE 11
FIGURE 12
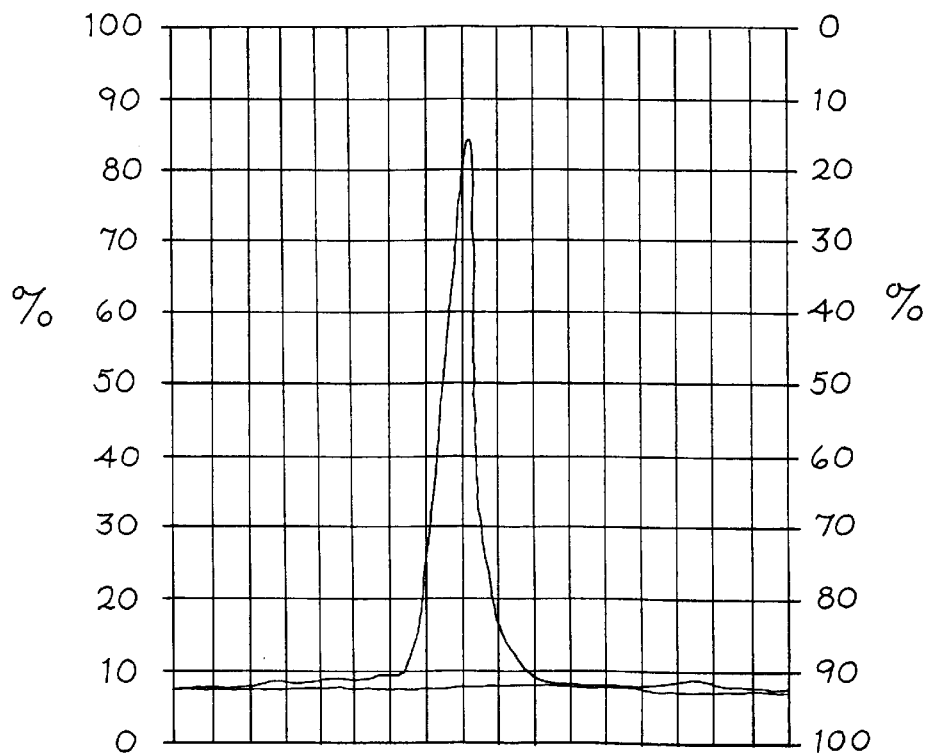

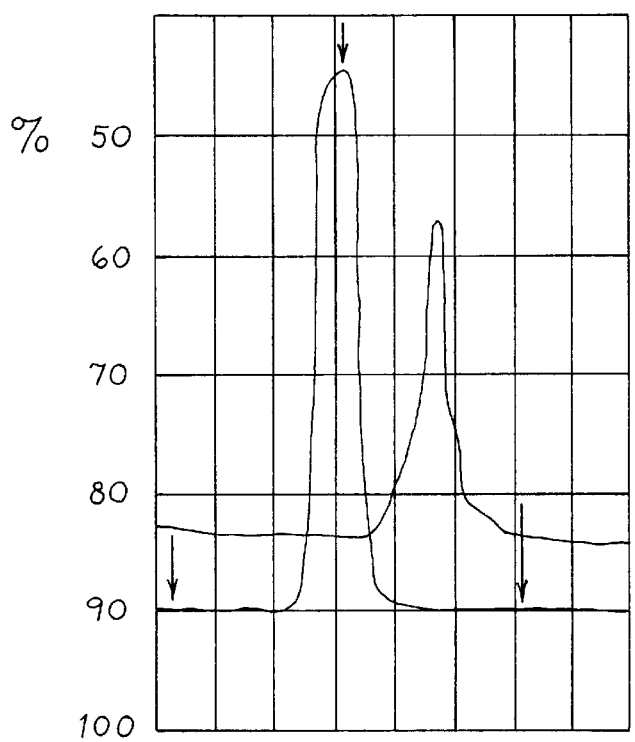
FIGURE 13
FIGURE 16A
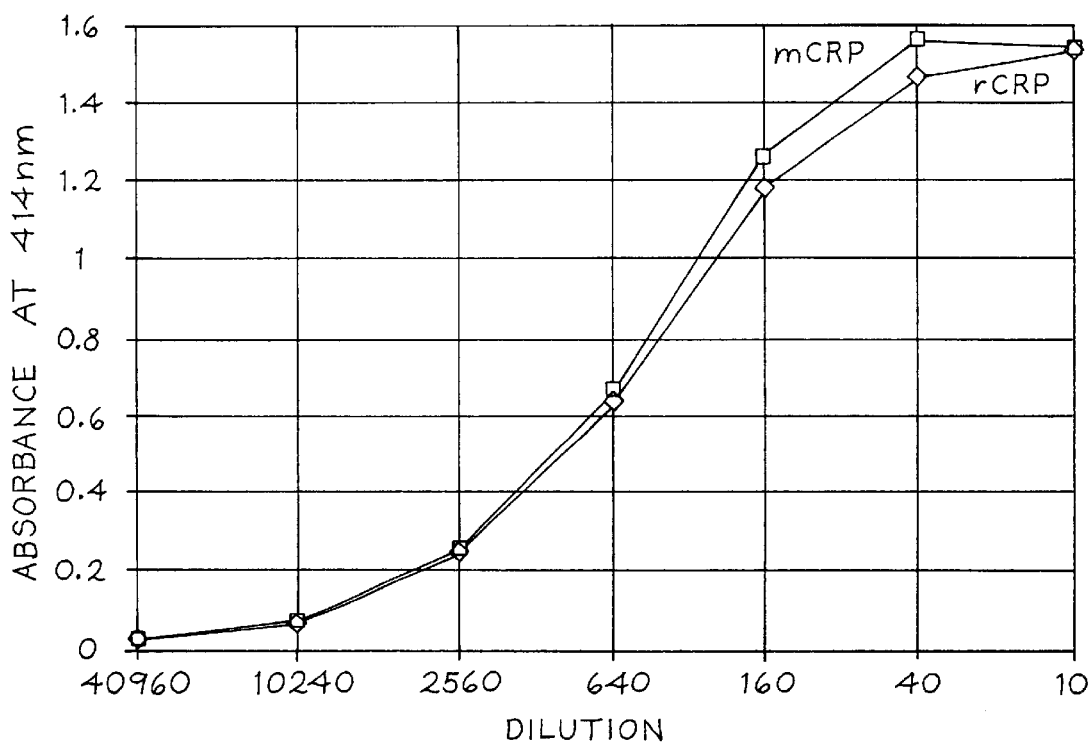

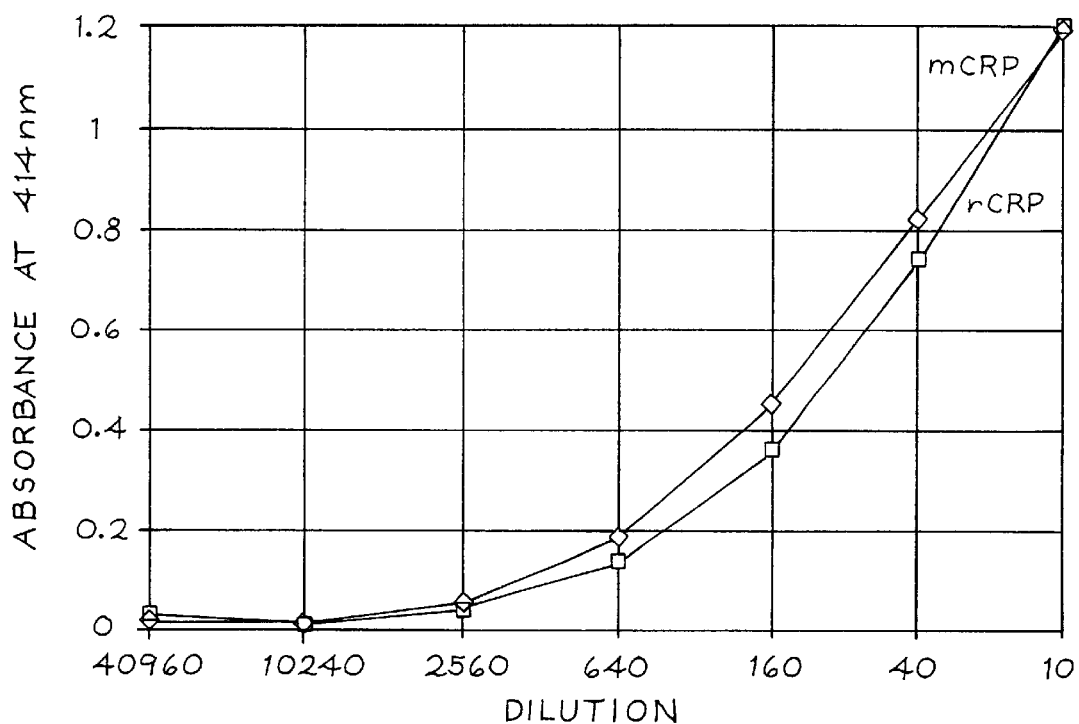
FIGURE 16B
FIGURE 16C
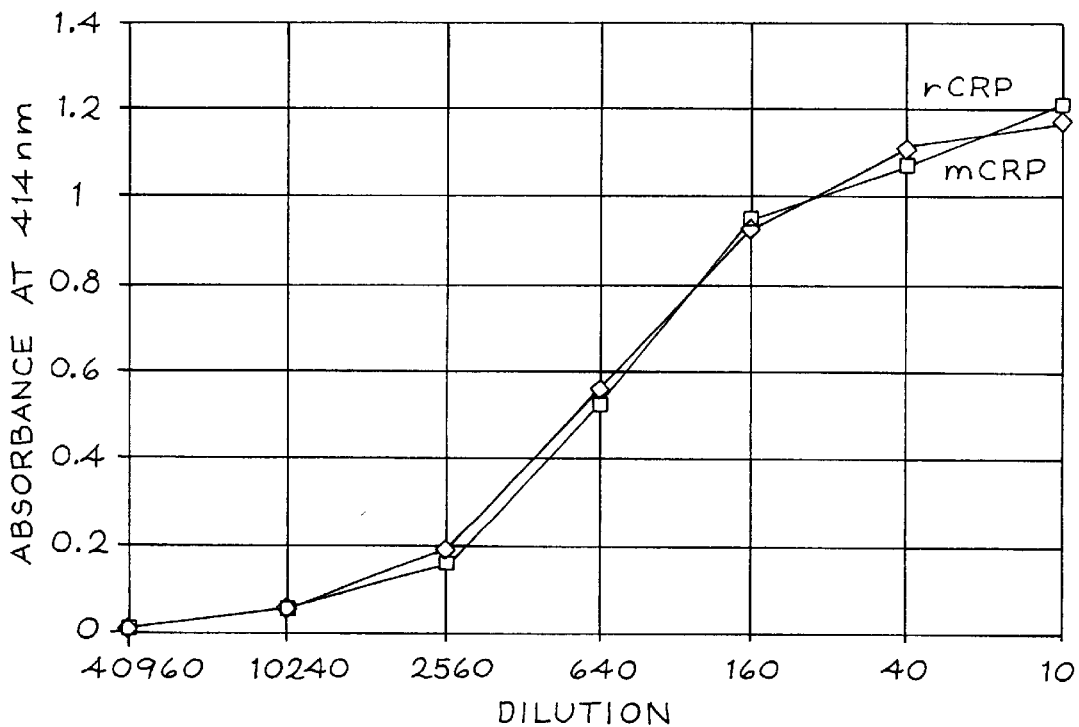

MUTANT PROTEIN AND METHODS AND MATERIALS FOR MAKING AND USING IT

This application is a division of application Ser. No. 09/212,850, filed Dec. 16, 1998, which was a division of application Ser. No. 08/480,270, filed Jun. 7, 1995, now U.S. Pat. No. 5,874,238, which was a division of application Ser. No. 08/296,545, filed Aug. 26, 1994, now abandoned, which was a continuation-in-part of application Ser. No. 08/023,952, filed Feb. 26, 1993, now abandoned.

FIELD OF THE INVENTION

This invention relates to a mutant protein having at least one of the biological activities of modified-C-reactive protein and to methods and materials for making the mutant protein by recombinant DNA techniques. The invention also relates to methods and materials for using the mutant protein.

BACKGROUND OF THE INVENTION

C-reactive protein was first described by Tillett and Francis [*J. Exp. Med.*, 52, 561–71 (1930)] who observed that sera from acutely ill patients precipitated with the C-polysaccharide of the cell wall of *Streptococcus pneumoniae*. Others subsequently identified the reactive serum factor as protein, hence the designation "C-reactive protein."

C-reactive protein (CRP) is synthesized in the liver, and its concentration in serum may increase as much as 1,000-fold during the acute phase response. See Gewurz et al., *Adv. Int. Med.*, 27, 345–372 (1982); Kushner, *Ann. N.Y. Acad. Sci.*, 389, 39–48 (1982); Pepys et al., *Adv. Immunol.*, 34, 141–212 (1983). Although the exact role of CRP in the acute phase response is not known, it is believed to play an important part in host defense. For instance, it has been reported that: (1) CRP binds phosphorylcholine, suggesting a role for CRP as an opsonin for microorganisms and damaged tissue that have exposed phosphorylcholine groups; (2) CRP binds chromatin, suggesting that CRP may act to scavenge chromatin released by cell lysis; (3) CRP neutralizes platelet activating factor, suggesting that CRP may function as a regulator of platelet and neutrophil activities; and (4) CRP complexed to certain other molecules or liposomes activates complement, suggesting that CRP may trigger the complement cascade. See Kaplan et al., *J. Immunol.*, 112, 2135–2147 (1974); Volanakis et al., *J. Immunol.*, 113, 9–17 (1974); Siegel et al., *J. Exp. Med.*, 140, 631–47 (1974); Siegel et al., *J. Exp. Med.*, 142, 709–211 (1975); Mold et al., *J. Exp. Med.*, 154, 1703–1708 (1981); Narkates et al., *Proc. N.Y. Acad. Sci.*, 389, 172–182 (1982); Nakayama et al., *Clin. Exp. Immunol.*, 54, 319–326 (1983); Robey et al., *J. Biol. Chem.*, 259, 7311–7316 (1984); Robey et al., *J. Exp. Med.*, 161, 1344–56 (1985); Vigo, *J. Biol. Chem.*, 260, 3418–3422 (1985); Shephard et al., *Clin. Exp. Immunol.*, 63, 718–27 (1986); Horowitz et al., *J. Immunol.*, 138, 2598–2603 (1987); Tatsumi et al., *Clinica Chimica Acta*, 172, 85–92 (1988); DuClos et al., *J. Immunol.*, 141, 4266–4260 (1988); DuClos et al., *J. Immunol.*, 146, 1220–1225 (1991); Xia et al., *FASEB J.*, 6, 1344a (1992).

CRP is a pentamer which consists of five identical subunits, each having a molecular weight of about 23,500. The pentameric form of CRP is sometimes referred to as "native CRP."

In about 1983, another form of CRP was discovered which is referred to as "modified-CRP" or "mCRP". Modified-CRP has significantly different charge, size, solubility and antigenicity characteristics as compared to native CRP. Potempa et al., *Mol. Immunol.*, 20, 1165–75 (1983). Modified-CRP also differs from native CRP in binding characteristics; for instance, mCRP does not bind phosphorylcholine. Id.; Chudwin et al., *J. Allercy Clin. Immunol.*, 77, 216a (1986). Finally, mCRP differs from native CRP in its biological activity. See Potempa et al., *Protides Biol. Fluids*, 34, 287–290 (1986); Potempa et al., *Inflammation*, 12, 391–405 (1988).

The distinctive antigenicity of mCRP has been referred to as "neo-CRP." Neo-CRP antigenicity is expressed on:

1) denatured CRP prepared using suitable conditions (described below);
2) the primary translation product of DNA coding for CRP (preCRP); and
3) CRP immobilized on solid surfaces.

Potempa et al., *Mol Immunol.*, 20, 1165–75 (1983); Mantzouranis et al., *Ped. Res.*, 18, 260a (1984); Samols et al., *Biochem. J.*, 227, 759–65 (1985); Chudwin et al., *J. Allergy Clin. Immunol.*, 77, 216a (1986); Potempa et al., *Inflammation*, 12, 391–405 (1988).

The neo-CRP antigenicity may be detected with antibodies. For instance, an antiserum made specific for neo-CRP can be used. See Potempa et al., *Mol Immunol.*, 24, 531–41 (1987). Alternatively, the unique antigenic determinants of mCRP can be detected with monoclonal antibodies. Suitable monoclonal antibodies are described in U.S. Pat. No. 5,272,257, published PCT application WO 91/00872 (published Jan. 24, 1991; corresponding to U.S. Pat. No. 5,272,257), Ying et al., *J. Immunol.*, 143, 221–228 (1989), Ying et al., *Immunol.*, 76, 324–330 (1992), and Ying et al., *Molec. Immunol.*, 29, 677–687 (1992).

A molecule reactive with antiserum specific for neo-CRP has been identified on the surface of 10–25% of peripheral blood lymphocytes (predominantly NK and B cells), 80% of monocytes and 60% of neutrophils, and at sites of tissue injury. Potempa et al., *FASEB J.*, 2, 731a (1988); Bray et al., *Clin. Immunol. Newsletter*, 8, 137–140 (1987); Rees et al., *Fed. Proc.*, 45, 263a (1986). In addition, it has been reported that mCRP can influence the development of monocyte cytotoxicity, improve the accessory cell function of monocytes, potentiate aggregated-IgG-ihduced phagocytic cell oxidative metabolism, and increase the production of interleukin-1, prostaglandin E and lipoxygenase products by monocytes. Potempa et al., *Protides Biol. Fluids*, 34, 287–290 (1987); Chu et al., *Proc. Amer. Acad. Cancer Res.*, 28, 344a (1987); Potempa et al., *Proc. Amer. Acad. Cancer Res.*, 28, 344a (1987); Zeller et al., *Fed. Proc.*, 46, 1033a (1987); Potempa et al., *Inflammation*, 12, 391–405 (1988); Chu et al., *Proc. Amer. Acad. Cancer Res.*, 29, 371a (1988). Chudwin et al., *J. Allergy Clin. Immunol.*, 77, 216a (1986) teaches that mCRP can have a protective effect in mice challenged with gram-positive type 7F *Streptococcus pneumoniae*.

Other activities of mCRP have been discovered and are described in certain issued U.S. patents, co-pending U.S. applications and published PCT applications. In particular, it has been discovered that mCRP binds immune complexes and aggregated immunbglobulin and can, therefore, be used to remove immune complexes and aggregated immunoglobulin from fluids and to quantitate immune complexes. See published PCT application WO 89/09628 (published Oct. 19, 1989), which corresponds to co-pending U.S. application Ser. No. 08/271,137, filed Jul. 6, 1994 (which was a continuation of application Ser. No. 07/582,884, filed Oct. 3, 1990, now abandoned, which was a continuation-in-part of application Ser. No. 07/176,923, filed Apr. 4, 1988, now abandoned). Modified-CRP has also been found to be effective in treating viral infections (see co-pending U.S. application Ser. No. 08/117,874, filed Sep. 7, 1993, a continuation of application Ser. No. 07/799,448, filed Nov. 27, 1991, now abandoned), non-Strentococcal bacterial infections and endotoxic shock (see allowed U.S. application Ser. No. 07/800,508, filed Nov. 27, 1991), and cancer (see issued U.S. Pat. No. 5,283,238 and co-pending U.S. application Ser. No. 08/149,663, filed Nov. 9, 1993).

For a brief review of CRP and mCRP, see Gotschlich, *Ann. N.Y. Acad. Sci.*, 557, 9–18 (1989). Kilpatrick and Volanakis, *Immunol. Res.*, 10, 43–53 (1991) provides a recent review of CRP.

Prior to the present invention, mCRP was preferably made using purified CRP as a starting material. Generally, mCRP was prepared from CRP by denaturing the CRP. For instance, CRP could be denatured by: (1) treatment with an effective amount of urea (preferably 8M) in the presence of a conventional chelator (preferably ethylenediamine tetraacetic acid (EDTA) or citric acid); (2) adjusting the pH of the CRP to below about 3 or above about 11–12; or (3) heating CRP above 50° C. for a time sufficient to cause denaturation (preferably at 639° C. for 2 minutes) in the absence of calcium or in the presence of a chelator such as those listed above. Urea treatment has been the preferred method. In addition, mCRP can be prepared from CRP by adsorbing the CRP onto solid surfaces. It is believed that mCRP prepared from CRP is formed by the dissociation of the five CRP subunits, each of which then undergoes a spontaneous conformational change to form mCRP. See Bray et al., *Clin. Immunol. Newsletter*, 8, 137–140 (1987).

Although biological sources of CRP and methods of purifying it from those sources are well known, purified CRP can be obtained from such sources only in limited quantities. Accordingly, mCRP could not be produced from CRP in commercial quantities.

Genomic and cDNA clones coding for human, mouse, and rabbit CRP have been isolated. Tucci et al., *J. Immunol.*, 131, 2416–2419 (1983); Whitehead et al., *Science*, 221, 69–71 (1983); Lei et al., *J. Biol. Chem.*, 260, 13377–83 (1985); Woo et al., *J. Biol. Chem.*, 260, 13384–88 (1985); Hu et al., *Biochem.*, 25, 7834–39 (1986); Samols and Hu, *Protides Biol. Fluids*, 34, 263–66 (1986); Syin et al., *J. Biol. Chem.*, 261, 5473–79 (1986); Ciliberto et al., *Nucleic Acids Res.*, 15, 5895 (1987); Hu et al., *J. Biol. Chem.*, 263, 1500–1504 (1988); Whitehead et al., *Biochem. J.*, 266, 283–90 (1990). To obtain pentameric native CRP, eukaryotic host cells, preferably mammalian host cells, should be used. See Samols and Hu, *Protides Biol. Fluids*, 34, 263–66 (1986); Hu et al., *J. Biol. Chem.*, 263, 1500–1504 (1988). Thus, native CRP could be produced in large quantities by recombinant DNA techniques and then converted into mCRP as described above. However, it would be convenient to have a direct method of making mCRP or a molecule having the biological activities of mCRP by recombinant DNA techniques.

As noted above, the primary translation product of the CRP MRNA (preCRP) has been found to express neo-CRP antigenicity. precRP is a precursor protein consisting of a signal or leader sequence attached to the N-terminus of the CRP subunit. During normal processing, the signal or leader sequence is cleaved from the preCRP molecule to produce mature CRP subunits which assemble into pentameric native CRP. Accordingly, mCRP could be prepared by selecting conditions so that pentameric native CRP is not formed from the preCRP. This can be accomplished by expressing a CRP genomic or cDNA clone in a prokaryotic host. See Samols and Hu, *Prot. Biol. Fluids*, 34, 263–66 (1986).

In attempting to produce mCRP in this manner, Applicants have discovered that the product of a CRP cDNA clone expressed in *Escherichia coli* consists of aggregates of CRP subunits and/or preCRP and CRP fragments, as well as free CRP subunits and/or preCRP. This cDNA product is extremely insoluble, and purification has proved problematical. In particular, Applicants have discovered that a substantial proportion of the aggregates in these preparations are formed by covalent cross-linking, and such cross-linked aggregates must be discarded, thereby significantly reducing yields.

Therefore, being able to produce a mutant CRP subunit or preCRP molecule having the biological activities of mCRP, but which was less likely to form covalently cross-linked aggregates than the unmutated protein, would be highly desirable in order to make processing and purification easier and more efficient. The present invention provides mutant proteins having these characteristics, and these mutant proteins may be produced by site-directed mutagenesis of a CRP cDNA or genomic clone as further described below.

Agrawal et al., *FASEB J.*, 6, 1427a (1992) and Agrawal et al., *J. Biol. Chem.*, 267, 25352–58 (1992) report the use of site-specific mutagenesis of a CRP cDNA clone to investigate the structural determinants of the phosphorylcholine binding site of CRP. Eight mutant recombinant CRP's were prepared: Tyr40→Phe; Glu42→Gln; Tyr40→Phe and Glu42→Gln; Lys57→Gln; Arg58→Gly; Lys57→Gln and Arg58→Gly; Trp67→Lys; and Lys57→Gln, Arg58→Gly and Trp67→Lys. The authors concluded that Trp67 is critical for the structure of the phosphorylcholine binding site of CRP, that Lys57 and Arg58 also participate in the formation of this binding site, and that the tetrapeptide 39-Phe-Tyr-Thr-Glu has only a minimal or no role in the formation of this binding site.

Agrawal et al., *J. Immunol.*, 152, 5404–5410 (1994) reports the use of site-specific mutagenesis of a CRP cDNA clone to investigate the structural determinants of the C1q binding site of CRP. Eleven mutant recombinant CRP's were prepared: Asp112→Asn; Asp112→Ala; Asp112→Lys; Asp112→Glu; Lys114→Thr; Lys114→Ala; Lys114→Glu; Lys114→Arg; Arg116→Leu; Asp112→Asn and Lys114→Thr; and Asp112→Asn and Arg116→Leu. The authors concluded that Asp112 plays a major role in the formation of the C1q binding site of CRP and that Lys114 and, to a lesser extent, Arg116 play important, but indirect, roles in C1q binding and activation of complement by CRP complexes.

SUMMARY OF THE INVENTION

The invention provides a mutant protein which has the same amino acid sequence as an unmutated CRP subunit or an unmutated preCRP, except that at least one amino acid of the unmutated CRP subunit or unmutated preCRP has been deleted, at least one amino acid of the unmutated CRP subunit or unmutated preCRP has been replaced by another amino acid, at least one amino acid has been added to the unmutated CRP subunit or unmutated preCRP, or a combination of such changes has been made. The amino acid(s) added, deleted and/or replaced are chosen so that the mutant protein is less likely to form covalently cross-linked aggregates than the unmutated. CRP subunit or unmutated preCRP. The mutant protein also exhibits at least one of the biological activities of mCRP.

The invention further provides a DNA molecule coding for the mutant protein of the invention and a vector for expression of the mutant protein. The vector comprises a DNA sequence coding for a mutant protein of the invention operatively linked to expression control sequences.

There is also provided a host cell which has been transformed so that it contains DNA coding for a mutantprotein of the invention. The DNA coding for the mutant protein is operatively linked to expression control sequences.

The invention further provides a method of producing the mutant protein of the invention. The method comprises culturing a host cell which has been transformed so that it contains DNA coding for a mutant protein. The DNA coding for the mutant protein is operatively linked to expression control sequences. The culturing takes place under conditions permitting expression of the mutant protein.

The invention also provides methods of using the mutant proteins of the invention. In particular, the mutant proteins of the invention will have at least one of the biological activities of mCRP and can be used as mCRP would be used. For instance, the mutant proteins of the invention bind aggregated immunoglobulin and immune complexes. They can, therefore, like mCRP, be used to remove aggregated immunoglobulin and immune complexes from fluids, to quantitate immune complexes, and to reduce the levels of immune complexes in a mammal in need thereof. The mutant proteins of the invention can also be used to treat viral infections, bacterial infections, endotoxic shock and cancer.

The invention further provides a device for removing aggregated immunoglobulin and immune complexes from fluids. The device comprises a solid surface to which is bound a mutant protein of the invention. The device also comprises a means for encasing the solid surface so that the fluid may be contacted with the solid surface.

The invention also provides a kit for quantitating immune complexes. The kit comprises a container of one of the mutant proteins of the invention.

Finally, the invention provides a therapeutic composition comprising a mutant protein of the invention in combination with a pharmaceutically-acceptable carrier and a mutant protein of the invention which is labeled. The labeled mutant protein may be used to detect or quantitate immune complexes or to detect cancer cells.

BRIEF DESCRIPTION OF THE DRAWINGS

FIG. 1B is a restriction map of plasmid pIT4.

FIG. 3A is native CRP, FIG. 3B is mCRP, FIG. 3C is wild-type recombinant CRP, and FIG. 3D is a mutant protein according to the invention.

FIGS. 6A–B are graphs of the results of ELISA assays to detect binding to aggregated IgG and monomeric IgG.

FIG. 10A is an SDS-PAGE gel obtained by electrophoresing three lots of inclusion body preparations isolated from *E. coli* BLR(DE3) bearing plasmid pIT13.

FIG. 11 is a representative elution profile obtained from Q-Sepharose Fast Flow$^R$ chromatography. performed as a step in the purification of a mutant protein according to the invention from *E. coli* BLR(DE3) bearing plasmid pIT13.

FIG. 12 is a representative elution profile obtained by Superdex 200 chromatography performed as a step in the purification of a mutant protein according to the invention from *E. coli* BLR(DE3) bearing plasmid pIT13.

FIG. 13 is a representative elution profile obtained by Sephadex G-25 chromatography performed as a step in the purification of a mutant protein according to the invention from *E. coli* BLR(DE3) bearing plasmid pIT13.

FIGS. 16A–C are graphs of the results of ELISA assays performed to detect the presence of neo-CRP antigenic determinants on mCRP and a mutant protein according to the invention purified from *E. coli* BLR(DE3) bearing plasmid pIT13. Three different anti-neo-CRP monoclonal antibodies were used: 3H12 (FIG. 17A); 8C10 (FIG. 17B); and 7A8 (FIG. 17C).

DETAILED DESCRIPTION OF THE PRESENTLY PREFERRED EMBODIMENTS

Figure 1A:
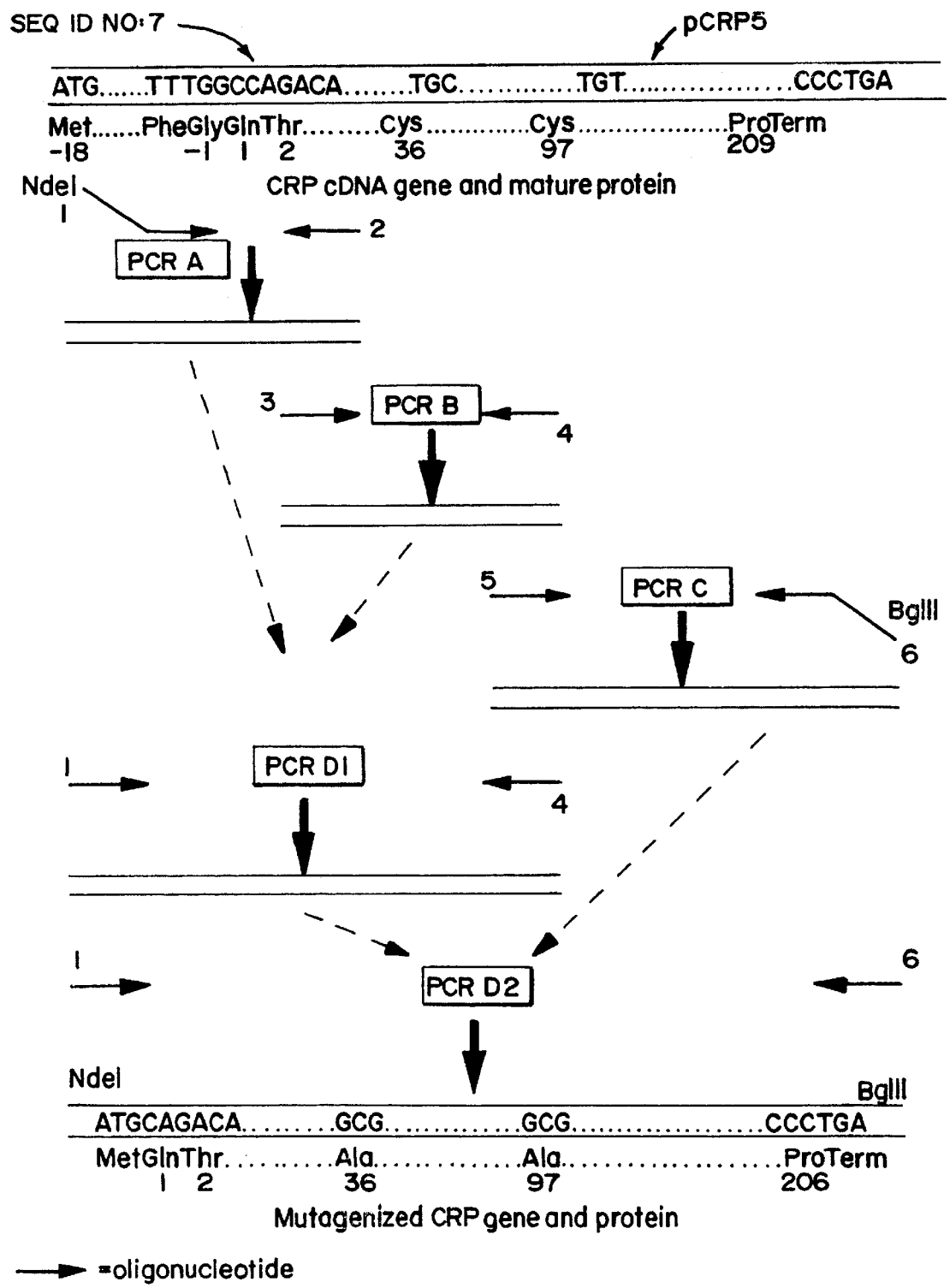
FIG. 1A is a diagram of a series of polymerase chain reactions.

The mutant proteins of the invention have at least one amino acid added, deleted or replaced as compared to an unmutated CRP subunit or unmutated preCRP. However, the mutant proteins may have several amino acid changes as compared to the unmutated CRP subunit or unmutated preCRP. For instance, the mutant proteins may have several added amino acids, several deleted amino acids, several replacement amino acids, or a combination of added, deleted, or replacement amino acids, as compared to the unmutated CRP subunit or preCRP.

The amino acid(s) added, deleted and/or replaced are chosen so that the mutant protein is less likely to form covalently cross-linked aggregates than the unmutated CRP subunit or unmutated preCRP. Suitable amino acid changes include the deletion or replacement of at least one, preferably all, of the cysteines in an unmutated CRP subunit or unmutated preCRP. All CRP subunits and preCRP's contain at least one cysteine. Mammalian CRP subunits contain two cysteines, and mammalian preCRP's contain three cysteines. It is believed that some of these cysteines form intermolecular disulfide bonds, thereby contributing to the formation of covalently cross-linked aggregates. Therefore, one or, preferably, all of the cysteines are desirably deleted or replaced. When the cysteines are replaced with other amino acids, they are preferably replaced with glycine, alanine, valine, leucine, isoleucine, serine, threonine or methionine, but any amino acid can be used. Most preferred is substitution with alanine.

As a result of the amino acid changes in them, the mutant proteins of the invention are easier to purify with much higher yields than unmutated CRP subunits or unmutated preCRP's. Also, the final product is much purer with many fewer aggregates and fragments than that obtained with unmutated CRP subunits or unmutated preCRP's.

Not all of the amino acid additions, deletions and replacements need contribute to the reduced likelihood of forming covalently cross-linked aggregates as long as the combined effect of all the changes is a reduction in intermolecular covalent cross-linking. For instance, the recombinant DNA manipulations used to produce the mutant proteins may result in amino acids being added at the amino or carboxy terminal ends of the CRP subunit or preCRP. This is acceptable as long as these amino acids do not contribute to the production of covalently cross-linked aggregates. In addition, some of the amino acid changes may be made for other purposes.

For instance, it is desirable to make amino acid changes which increase the solubility of the resultant mutant protein in aqueous media, since a more soluble mutant protein is easier to purify and process. It has been found that the solubility of the mutant proteins of the invention is improved if lysine residues are chemically altered by treatment with sulfo-N-hydroxysuccinimide-acetate (sulfo-NHS-acetate; which changes the positive charge of the epsilon amine group of lysine to a neutral charge), sulfosuccinimidyl-3-(4-hydroxyphenyl) propionate (which changes the positive charge of the epsilon amine group of lysine to a neutral charge and adds an aromatic functional group), or succinic anhydride (which changes the positive charge of the epsilon amine group of lysine to a negative charge). Therefore, one or more of the lysine residues of an unmutated CRP subunit or preCRP is preferably deleted or replaced with another amino acid to improve the solubility of theiresultant mutant protein. Other suitable amino acid changes to increase the solubility of the mutant proteins of the invention include deleting one or more hydrophobic amino acids, replacing one or more hydrophobic amino acids with charged amino acids, adding one or more charged amino acids, or combinations of these changes. However, for the reasons stated above, the addition of lysine residues should be avoided.

Aqueous media include water, saline, buffers, culture media, and body fluids.

The mutant proteins of the invention also exhibit at least one of the biological activities of mCRP. As used herein, "biological activity" refers to properties of mCRP other than its physical and chemical properties. The biological activities of mCRP include its ability to bind aggregated immunoglobulin and immune complexes which allows mCRP to be used to removed aggregated immunoglobulin and immune complexes from fluids (such as antibody reagents or body fluids), to quantitate immune complexes, and to reduce the levels of immune complexes in a mammal in need thereof. The biological activities of mCRP also include its effectiveness in treating viral infections, bacterial infections, endotoxic shock and cancer.

For instance, it has been found that the mutant proteins of the present invention can bind aggregated immunoglobulin and immune complexes. The binding of the aggregated immuno lobulin or immune complexes may be accomplished by adding a mutant protein directly to a fluid containing aggregated immunoglobulin or immune complexes, or a mutant protein may first be immobilized on a solid support before being contacted with the fluid containing the aggregated immunoglobulin or immune complexes. When the mutant protein is bound on a solid support, fluids may be incubated statically on the immobilized mutant protein when used for diagnostic assays, or fluids may be passed dynamically across the immobilized mutant protein in an extracorporeal device when used for therapeutic treatment to bind immune complexes in a body fluid.

Suitable solid support materials for use in the present invention may be made of agarose-based resin, polyacrylamide, polymethyl-methacrylate, polycarbonate, polysulfone, polyacrylonitrile, polyethylene, polypropylene, latex, dextran, glass, nylon, polyvinyl alcohol, gels, clay, cellulose derivatives, and any other hydrophobicor hydrophilic polymeric material. The solid support may be in the form of beads for use in a column, may be in the form of the wells of a microtiter plate, may be in the form of a hollow fiber membrane, or may take other forms as discussed below. Column and solid phase materials are commercially available in the United States from Bio Rad Laboratories (Richmond, Calif.); Pierce Chemical Co. (Rockford, Ill.); Pall Biosupport (Glen Cove, N.Y.); Micro Membranes (Newark, N.J.); Pharmacia Fine Chemicals (Uppsala, Sweden); and others.

The mutant protein may be immobilized by covalent or non-covalent binding to the solid support. Methods of immobilizing proteins on solid supports are well known in the art. For instance, mutant proteins may be immobilized on solid supports by simply incubating the mutant protein with the solid support to adsorb the mutant protein.

To ensure maximum binding of aggregated immunoglobulin or immune complexes to the mutant protein, a linking agent may be utilized to secure the attachment of the mutant protein to polymeric materials. The mutant protein may be immobilized non-covalently or covalently on the surface of the polymeric material with the linking agent. For purposes of this invention, linking agents are incorporated as part of, or derivatized onto, the polymeric solid surface before the mutant protein is added. The linking agents are conventional; they include diimidoesters, carbodiimide, periodate, alkylhalides, dimethylpimelimidate and dimaleimides [See Blait, A. H., and Ghose, T. I., *J. Immunol. Methods*, 59:129 (1983); Blair, A. H., and Ghose, T. I., *Cancer Res.*, 41:2700 (1981); Gauthier, et al., *J. Expr. Med.*, 156:766–777 (1982)].

Conjugation of the mutant protein to the linking agent generally requires an initial modification of protein amino acid R groups or cross linking agent or both. Such modifications may serve to selectively activate R groups (e., carbodiimide-O-acyl urea, intermediate formation with aspartic, glutamic, and C-terminal carboxyl residues) to allow for reaction with appropriate available agent functional groups (amino groups in the case of carbodiimide). Modifications can also include the introduction of a new reactive moiety (e.g., N-succinimidyl-3-(2-pyridyldithio)-propionate) which introduces pyridyldithio groups on lysine epsilon-amino residues. This allows for disulfide bond formation between protein and linking agent. In some cases, bifunctional coupling reagents are employed which form bridges between the protein R groups and the linking agent of interest.

The mutant proteins may be used to remove aggregated immunoglobulin or immune complexes from fluids used for research, in therapeutic procedures, or in diagnostic tests, e.g., solutions containing monoclonal antibodies, antisera, derivatized reagents, intravenous gamma globulin, or isolated blood components. The presence of aggregated immunoglobulin in such fluids may be expected because of processing steps used to make these fluids, such as heat treatment of antisera to inactivate complement. The mutant protein may be bound on a solid support for removing aggregated or complexed immunoglobulins from such fluids. Suitable solid supports are those described above, and the mutant protein is bound to them in the ways described above. Alternatively, the mutant protein may be added directly to such fluids in order to remove the aggregated or complexed immunoglobulins.

Mutant proteins of the present invention can also be used to remove immune complexes from body fluids, such as whole blood or plasma, by contacting the fluid with the mutant protein. The mutant protein may be added directly to the body fluid or may be immobilized on a solid support and then contacted with the body fluid. Suitable solid supports are those described above, and the mutant protein is bound to them in the ways described above.

Persistent high levels of immune complexes may be found in diseases such as cancer, autoimmune diseases, arthritis, and infections. The continued presence of immune complexes in the circulation and their deposition in tissues contributes to compromised immune system function and inflammatory pathology. Accordingly, reducing the level of immune complexes should be beneficial. See Theofilopoulos et al., *Adv. Immunol.*, 28. 90–220 (1979), Theofilopoulos et al., *Immunodiagnostics of Cancer*, p. 896 (1979).

For such therapeutic uses, the mutant protein may be contacted with the body fluid by passing the blood, plasma or other fluid through an extracorporeal device having a solid support coated with mutant protein. The device also will have a means for encasing the solid support so that the fluid may contact the mutant protein bound to the solid support. The blood, plasma or other body fluid is circulated dynamically through the device so that the immune complexes contained therein are bound and removed as in, e.g., conventional plasmapheresis or hemodialysis techniques. The fluids can be returned to the body negating the need for blood replacement therapy.

The solid support and encasing means of the extracorporeal device may be made of any biocompatible material. For instance, the solid support may be a membranous surface, agarose-based beads or hollow fibers coated with mutant protein. The extracorporeal device may be a column packed with beads or a cylinder encasing a hollow fiber membrane. The device may also include appropriate tubing for connecting it to a patient and a pump to aid the passage of the fluid through the device and back into the patient and to prevent air from entering the system. In particular, conventional plasmapheresis devices may be used in the practice of the present invention by modifying them so that they contain a solid support on which mutant protein is immobilized. See, e.c., Randerson et al., *Art. Organs*, 6, 43–49 (1982); Smith et al., *Cleve. Clin. Q.*, 51, 135–142 (1984); Nilsson et al., *Plasma Ther. Transfus. Technol.*, 5, 127–134 (1984); Nilsson et al., in *Affinity Adsorption of Inhibitors*, pages 223–241 (Hoyer ed. 1984); Liberti, "Development Of A Universal Immune Specific Filtration Device (Blood Filter)," presented at Opportunities In The Oncology Marketplace; Mittelman et al., *Seminars in Hematology*, 26, 15–18 (1989); U.S. Pat. No. 4,432,871, issued Feb. 21, 1984; U.S. Pat. No. 4,551,435, issued Nov. 5, 1985; U.S. Pat. No. 4,614,513, issued Sep. 30, 1986 which describe conventional plasmapheresis devices.

The device must be sterilized for therapeutic use. Sterilization may be accomplished in conventional ways such as steam, heat, purging with ethylene oxide or irradiation.

The invention also comprises a method of detecting or quantitating immune complexes comprising contacting the immune complexes with a mutant protein of the invention so that the immune complexes bind to the mutant protein. The mutant protein may be added directly to fluids containing the immune complexes to detect or quantitate immune complexes in the fluids. Alternatively, the mutant protein may be immobilized oh a solid support before contacting it with fluids containing immune complexes. The mutant protein may also be added directly to cells or a tissue sample having immune complexes thereon, and labeled mutant protein may be injected into a mammal so that it localizes in areas of the mammal's body where immune complexes are found, such as areas of inflammation.

Suitable solid support materials are those described above, and mutant protein is immobilized on them in the ways described above. For diagnostic assays, suitable solid supports include those conventionally used for immunoassays. For instance, the solid support may be test tubes, the wells of a microtiter plate, latex beads, glass beads, other beads, filter paper, glass fiber filter paper, or dipsticks made of, e.g., polycarbonate, polysulfone or latex.

To detect or quantitate the immune complexes, labeled mutant protein can be used. The labels useful in the invention are those known in the art such as enzyme, fluorescent, bioluminescent, chemiluminescent, and radioactive labels and biotin.

Alternatively, the immune complexes can be detected or quantified using conventional immunoassay techniques by adding a labeled component that binds to the immune complexes or the mutant protein. Suitable labeled components include conventional reagents used in immunoassays. For instance, labeled antibodies to the immunoglobulin or the antigen in the immune complexes could be used or labeled Protein A which binds to the Fc portion of immunoglobulins could be used. The labels used are those described above.

Suitable conventional immunoassay techniques include agglutination, radioimmunoassay, enzyme immunoassays and fluorescence assays. For instance, the mutant protein may be coated onto latex beads for use in agglutination assays or onto dipsticks for use in qualitative or semi-quantitative immunoassays. Enzyme-linked immunosorbent assays (EIA) are preferred since they provide a means for sensitive quantitation of levels of immune complexes. In general, any immunoassay technique can be used which results in an observable change in properties.

The specific concentrations of reagents, the temperatures and times of incubations, as well as other assay conditions can be varied in whatever assay is employed to detect or quantitate immune complexes depending on such factors as the concentration of the immune complexes in the sample, the nature of the sample, and the like. Those skilled in the art will be able to determine operative and optimal assay conditions for each determination while employing routine experimentation. Since body fluids from mammals normally contain immune complexes, comparison of the levels of immune complexes in a test sample from a mammal will have to be made to the levels found in normals to identify levels of immune complexes indicative of a disease state.

A test kit for detecting or quantitating immune complexes is also part of the invention. The kit comprises a container holding a solution of mutant protein or mutant protein attached to a solid support. The solid supports are the types described above, and the mutant protein is attached as described above. Thus, the container could be a bottle holding a solution of mutant protein, a dipstick coated with mutant protein encased in a protective package, a bottle holding latex beads coated with mutant protein, or a microtiter plate, the wells of which are coated with mutant protein.

The mutant protein may be labeled if it is to be used for detecting or quantitating the immune complexes. Alternatively, the kit may further comprise a container holding a labeled component that allows for the detection or quantitation of the immune complexes by binding to the immune complexes or to the mutant protein. Suitable labeled components were described above.

The mutant proteins of the invention can be administered to a mammal to reduce the level of immune complexes in the mammal. It is believed that, upon introduction of the mutant protein into a body fluid of the mammal containing the immune complexes, the soluble immune complexes will grow larger in physical size and precipitate (fall out of solution) or will otherwise be modified to enhance their removal by phagocytes. To reduce the level of immune complexes in a mammal, an effective amount of a mutant protein is administered to the mammal by injection, preferably intravenous injection.

Modified-CRP has been chemically altered with the following reagents and the ability of the resultant chemically-altered mCRP's to bind aggregated IgG ascertained using an ELISA assay like that described in Example 1: sulfo-NHS-acetate (alters lysines); sulfosuccinimidyl-3-(4-hydroxyphenyl) propionate (alters lysines); succinic anhydride (alters lysines); NHS-biotin (alters lysines); p-hydroxy phenylgloxal (alters arginines); [2-(2-nitrophenylsulfeneyl)-3-methyl-3'-bromoindoleine] (alters tryptophans); tetranitromethane (alters tyrosines); iodobeads (alters tyrosines); diazo-norleucine methyl ester (alters aspartic acids and glutamic acids); N-ethyl maleimide (alters cysteines); peroxide (alters methionines); and diethylpyrocarbonate (alters histidines). These experiments indicated that tryptophan residues and amino acids with carboxylic acid groups (e.g., aspartic acid and glutamic acid) were involved in the binding of aggregated IgG by mCRP. Accordingly, in preparing mutant proteins according to the invention for use in binding aggregated immunoglobulin or immune complexes, the tryptophan residues and the amino acids having a carboxylic acid group in the unmutated CRP subunit or preCRP should preferably not be deleted or replaced with other amino acids as any such deletion or replacement may decrease the ability of the resultant mutant protein to bind aggregated immunoglobulin or immune complexes.

The mutant proteins of the invention can also be used to treat viral infections. They can be used to treat any type of viral infection such as Retroviridae infections. The Retroviridae are a family of spherical enveloped RNA viruses comprising three sub-families: Oncovirinae, Spurmavirinae and Lentivirinae. Hull et al, *Virology: Directory & Dictionary of Animal. Bacterial and Plant Viruses*, page 191 (Stockton Press 1989). Replication starts with reverse transcription of virus RNA into DNA which becomes integrated into the chromosomal DNA of the host. Id. Endogenous oncoviruses occur widely among vertebrates and are associated with many diseases. Id. The lentiviruses include HIV-1 and SIV. Fauci, *Science*, 239, 617–622 (1988).

To treat viral infections in a mammal, an effective amount of a mutant protein is administered to the mammal. The mutant protein is preferably administered to the mammal before the infection becomes too serious. Most preferably, the mutant protein is administered at the first indication of a viral infection or prophylactically to those at risk of developing viral infections. For instance, the mutant protein may be administered prophylactically to hemophiliacs or surgical patients who may receive blood contaminated with a virus such as HIV-1 or hepatitis. Of course, a mutant protein can be administered to a mammal already suffering from a viral infection.

The mutant protein will generally be administered to the mammal suffering from a viral infection by injection (e.g., intravenous, intra-peritoneal, subcutaneous, intramuscular). Preferably intravenous injection is used. The mutant protein may be injected in a fluid or may be encapsulated in liposomes. The mutant protein may also be applied topically to, e.g., a wound or other site of infection. Finally, it should be possible to administer the mutant protein by means of a spray to treat respiratory infections.

The mutant proteins of the invention may also be used to treat bacterial infections, especially gram-negative bacterial infections, and endotoxic shock. Endotoxins are the lipopolysaccharide components of the outer membranes of gram-negative bacteria that trigger many of the adverse systemic reactions and serious sequelae in sepsis and gram-negative bacteremia.

To treat a bacterial infection or endotoxic shock in a mammal, an effective amount of a mutant protein is administered to the mammal. The mutant protein is preferably administered to the mammal before the bacterial infection becomes too serious and septic shock or endotoxic shock has developed. Most preferably, the mutant protein is administered at the first indication of a bacterial infection or prophylactically to those at risk of developing bacterial infections. For instance, a mutant protein may be administered prophylactically to surgical patients or patients in intensive care who are at risk of developing bacterial infections. Of course, the mutant protein can be administered to a mammal already suffering from a bacterial infection or already suffering from septic shock or endotoxic shock.

The mutant protein will generally be administered to the mammal suffering from a bacterial infection or endotoxic shock by injection (e.g., intravenous, intraperitoneal, subcutaneous, intramuscular). It is preferably administered by intravenous injection. The mutant protein may be administered in a fluid or may be encapsulated in liposomes. The mutant protein may also be applied topically to, e.g., a wound or other site of infection, and it should be possible to administer the mutant protein by means of a spray to treat respiratory infections.

Finally; the mutant proteins of the invention can be used to treat cancer. It is contemplated that the mutant proteins of the invention can be used to treat a variety of cancers, including but not limited to, adenocarcinoma, lymphoma, fibrosarcoma, and leukemia, and to reduce metastasis. The mutant protein should be administered to the mammal when the presence of cancer cells in the mammal is first detected.

For the treatment of cancer, the mutant protein is preferably administered to the mammal by injection (e.g., intravenous, intraperitoneal, subcutaneous, intramuscular). The mutant protein may be administered in a fluid or encapsulated in liposomes.

It is understood by those skilled in the art that the dose of mutant protein that must be administered to a mammal for therapeutic treatment will vary depending on the mammal which will receive the mutant protein, the reason for administering the mutant protein (e.g., to reduce the level of immune complexes, to treat a viral infection, to treat a bacterial infection, to treat. endotoxic shock, to treat cancer), the severity of the mammal's condition, the route of administration, and the identity of any other drugs being administered to the mammal. It is also understood that it may be necessary to give more than one dose of the mutant protein.

Effective dosages and schedules for administration of the mutant protein may be determined empirically, and making such determinations is within the skill of the art. A dose of from about 5 $\mu$g to about 150 mg of mutant protein per kg of body weight, preferably from about 100 $\mu$g to about 20 mg per kg, will be effective for reducing the level of immune complexes, treating a viral infection, treating a bacterial infection, treating endotoxic shock or treating cancer. For treating cancer, the dose is most preferably from about 2 mg to about 10 mg per kg. Generally, one dose is sufficient for treating a bacterial infection or endotoxic shock. Multiple doses will generally be necessary for reducing the level of immune complexes, treating viral infections and treating cancer. If multiple doses are needed, the interval between doses is preferably from about 1 day to about 7 days. For treating cancer, the multiple doses are most preferably administered from about 1 to about 3 days apart. Administration of mutant protein should be continued until the level of immune complexes has returned to normal or until health has been restored to the mammal.

The mutant protein is administered to the mammal in a pharmaceutically-acceptable carrier. Pharmaceutically-acceptable carriers are well known. For instance, suitable carriers for the administration of the mutant proteins of the invention include fluids such as water, saline and buffers. Except when it is used to reduce the level of immune complexes, the mutant protein may also be administered encapsulated in liposomes [see Debdhar et al., *Cancer Research*, 42, 5084–5088 (1982); Thombre et al., *Cancer Immunol. Immunother.*, 16, 145–150 (1984); Barna et al., *Cancer Research*, 44, 305–310 (1984)]. For treatment of cancer, the mutant proteins are preferably administered encapsulated in liposomes. The term "liposome" refers to any sac-like or hollow vesicle-like structure which is capable of encapsulating a mutant protein and includes multilamellar vesicles, unilamellar vesicles, and red blood cell ghosts. Methods of preparing liposomes and encapsulating molecules in them are well known in the art. Preferably, the liposomes containing mutant protein are unilamellar vesicles formed by extrusion which may be prepared as described by MacDonald et al., *Biochim. Biophys. Acta*, 1061:297–301 (1991). For topical application, when appropriate, the mutant protein may be incorporated into lotions, gels, cremes, etc., as is well known in the art. It is within the skill in the art to determine acceptable and optimum carriers and routes of administration.

The mutant proteins may be administered to the mammal alone or in combination with other drugs. For instance, the mutant proteins may be administered in combination with antibiotics when used to treat a bacterial infection or may be administered with other anti-cancer agents when used for treating cancer. Effective dosages and schedules for administering the mutant proteins and these other drugs together may be determined empirically as set forth above. It is expected that smaller amounts of mutant protein and anti-cancer agent (50% or less) may be employed when they are used in combination as compared to when they are used individually to treat cancer. It is also within the skill in the art to determine acceptable and optimum carriers and routes of administration for the mutant proteins and the other drugs when they are used in combination.

The other cancer agents which can be used in combination with the mutant proteins include cytotoxic chemotherapeutic compounds known in the art such as Thiotepa, Busulfan, Cyclophosphamide, Methotrexate, Cytarabine, Bleomycin, cisplatin, Doxorubicin, Melphalan, Mercaptopurine, Vinblastine, and 5-Fluorouracil. Other suitable chemotherapeutic compounds are listed in Krakoff, *CA-A Cancer Journal For Clinicians*, 41:264–278 (1991). Typically, cytotoxic agents function in destroying cells and/or preventing their multiplication and are thus, useful in treating cancer. The other anti-cancer agent may also be an immunoadjuvant or cytokine. Immunoadjuvants and cytokines, also referred to as "biological response modifiers," are known in the art. Generally, such molecules are useful in stimulating or enhancing host defense mechanisms and are therefore useful in anti-cancer therapy. Examples of immunoadjuvants or cytokines that may be administered include interferon(s), colony stimulating factor (CSF), tumor necrosis factor (TNF), hormones such as steroids, and interleukins such as IL-1, IL-2, and IL-6.

The mutant proteins may also be used as imaging agents for detecting immune complexes or cancer cells in vivo. To do so a labeled mutant protein will be injected into a mammal and will localize in areas where immune complexes have been deposited (such as areas of inflammation) or in areas where cancer cells are located. Alternatively, an unlabeled mutant protein can be injected. Then a labeled material which binds to the mutant protein is injected, and this labeled material binds to the mutant protein in areas where it has localized. Methods of making and using imaging agents and suitable labels for them are well-known in the art.

The mutant proteins of the invention can be prepared by expression of DNA coding for them in transformed host cells. DNA coding for a mutant protein according to the invention can be prepared by in vitro mutagenesis of a CRP genomic or cDNA clone or can be chemically synthesized.

As discussed in the Background section, genomic and cDNA clones coding for human, mouse, and rabbit CRP have been isolated. There is substantial homology between the amino acid sequences of CRP's from different species. For instance, there is from about 50 to about 80% sequence homology between CRP's from various mammalian species. Hu et al., *Biochem.*, 25, 7834–39 (1986); Whitehead et al., Biochem. J., 266, 283–90 (1990); Kilpatrick and Volanakis, Immunol. Res., 10 43–53 (1991). Given the substantial homology between CRP's from different species, probes can readily be prepared so that genomic and cDNA clones can be isolated which code for CRP's from other species. Methods of preparing such probes and isolating genomic and CDNA clones are well known. See, e.q., Lei et al., J. Biol. Chem., 260, 13377–83 (1985); Woo et al., J. Biol. Chem., 260, 13384–88 (1985); Hu et al., Biochem., 25, 7834–39 (1986); Hu et al., J. Biol. Chem., 263, 1500–1504 (1988); Whitehead et al., Biochem. J., 266, 283–90 (1990).

Using one of the known clones or a newly-isolated clone, DNA coding for a mutant protein according to the invention can be prepared using conventional and well known in vitro mutagenesis techniques. Particularly preferred is site-directed mutagenesis using polymerase chain reaction (PCR) amplification. See Example 1. The following references describe other site-directed mutagenesis techniques which can be used to produce DNA coding for a mutant protein of the invention: *Current Protocols In Molecular Bioloay*, Chapter 8, (Ansubel ed. 1987); Smith & Gilliam, *Genetic Engineering Principles And Methods*, 3, 1–32 (1981); Zoller & Smith, *Nucleic Acids Res.*, 10, 6487–6500 (1982); Zoller et al., *Methods Enzymol.*, 100, 468–500 (1983); Zoller & Smith, *DNA*, 3, 479–88 (1984); Brake et al., *Proc. Natl. Acad. Sci. USA*, 81, 4642–46 (1984); *Bio/Technology*, pages 636–39 (July 1984); Botstein et al., *Science*, 229, 1193 (1985); Kunkel et al., *Methods Enzymol.*, 154, 367–82 (1987).

DNA coding for a mutant protein of the invention can also be prepared by chemical synthesis. Methods of chemically synthesizing DNA having a specific sequence are well-known in the art. Such procedures in-clude the phosphoramidite method (see, e.g., Beaucage and Caruthers, *Tetrahedron Letters*, 22, 1859 (1981); Matteucci and Caruthers, *Tetrahedron Letters*, 21, 719 (1980); and Matteucci and Caruthers, *J. Amer. Chem. Soc.*, 103, 3185 (1981)) and the phosphotriester approach (see, e.g., Ito et al., *Nucleic Acids Res.*, 10, 1755–69 (1982)).

The invention also includes a vector which comprises a DNA sequence coding for a mutant protein according to the invention. The DNA coding sequence is operatively linked in the vector to appropriate expression control sequences. Methods of effecting this operative linking, either before or after the DNA coding for the mutant protein is inserted into the vector, are well known. Expression control sequences include pro-moters, activators, enhancers, operators, stop signals, cap signals, polyadenylation signals, and other signals involved with the control of transcription.

The vector must contain a promoter and a trans-cription termination signal, both operatively linked to the DNA sequence, i.e., the promoter is upstream of the DNA sequence and the termination signal is downstream from it. The promoter may be any DNA sequence that shows transcriptional activity in the host cell and may be derived from genes encoding homologous or heterologous proteins and either extracellular or intracellular proteins, such as amylase, glycoamylases, proteases, lipases, cellulases, and glycolytic enzymes. Also, a promoter recognized by T7 RNA polymerase may be used if the host is also engineered to contain the gene coding for T7 RNA polymerase. The promoter may contain upstream or downstream activator and enhancer sequences. An operator sequence may also be included downstream of the promoter, if desired.

However, the promoter need not be identical to any naturally-occurring promoter. It may be composed of portions of various promoters or may be partially or totally synthetic. Guidance for the design of promoters is provided by studies of promoter structure such as that of Harley and Reynolds, *Nucleic Acids Res.*, 15, 2343–61 (1987). Also, the location of the promoter relative to the transcription; start may be optimized. See Roberts, et al., *Proc. Natl Acad. Sci. USA*, 76, 760–4 (1979).

Expression control sequences suitable for use in the invention are well known. They include those of the *E. coli* lac system, the *E. coli* trp system, the TAC system and the TRC system; the major operator and pro-moter regions of bacteriophage lambda; the control region of filamentous single-stranded DNA phages; the expression control sequences of other bacteria; promoters derived from genes coding, for *Saccharomydes cerevisiae* TPI, ADH, PGK and alpha-factor; promoters derived from genes coding for the *Aspergillus oryzae* TAKA amylase and *A. niger* glycoamylase, neutral alpha-amylase and acid stable alpha-amylase; promoters derived from genes coding for *Rhizomucor miehei* aspartic proteinase and lipase; mouse mammary tumor promoter; SV40 promoter; the actin pro-moter; and other sequences known to control the expression of genes of prokaryotic cells, eukaryotic cells, their viruses, or combinations thereof.

The vector may be a self-replicating vector or an integrative vector. If the vector is self-replicating, it must contain one or more replication systems which allow it to replicate in the host cells. In particular, when the host is a yeast, the vector should contain the yeast 2 u replication genes REP1-3 and origin of replication.

When the vector is a self-replicating vector, it is preferably a high copy number plasmid so that high levels of expression are obtained. As used herein, a. "high copy number plasmid" is one which is present at about 100 copies or more per cell. Many suitable high copy number plasmids are known and include bacterial plasmids such as pUC and yeast plasmids such as pC.

Alternatively, an integrating vector may be used which allows the integration into the host cell's chromosome of the DNA coding for the mutant proteins. Although the copy number of the coding sequences in the host cells would be lower than when self-replicating vectors are used, transformants having sequences integrated into their chromosomes are generally quite stable.

The vector should further include one or more restriction enzyme sites for inserting DNA sequences into the vector, and preferably contains a DNA sequence coding for a selectable or identifiable phenotypic trait which is manifested when the vector is present in the host cell ("a selection marker"). Suitable selection markers are well known in the art.

Suitable vectors for use in the invention are well known. They include retroviral vectors, vaccinia vectors, pUC (such as pUC8 and pUC4K), pBR (such as pBR322 and pBR328), pTZ (such as pTZ18R), pUR (such as pUR288), phage lambda, YEp (such as YEP24) plasmids, and derivatives of these vectors.

DNA coding for a signal or signal-leader sequence may be located upstream of the DNA sequences encoding the mutant proteins. A signal or signal-leader sequence is an amino acid sequence at the amino terminus of a protein which allows the protein to which it is attached to be secreted from the cell in which it is produced. Suitable signal and signal-leader sequences are well known and include the CRP presequence (see Background section), yeast 4-factor signal sequence (see U.S. Pat. Nos. 4,546,082 and 4,870, 008), the yeast BAR1 secretion system (see U.S. Pat. No. 4,613,572), *Kluyveromyces lactis* signal-leader sequence, and the yeast invertase signal sequence (Stetler et al., *Bio/Technology*, 7:55–60 (1989), Smith et al., *Science*, 229:1219–1229 (1985)). Although secreted proteins are often easier to purify, expression levels are much lower than those that can be obtained in the absence of secretion.

Chemical synthesis of DNA coding and other sequences is preferable for several reasons. First, chemical synthesis is desirable because codons preferred by the host in which the DNA sequence will be expressed may be used to optimize expression of the mutant proteins. Not all of the codons need to be altered to obtain improved expression, but greater than 50%, most preferably at least about 80%, of the codons should be changed to host-preferred codons.

The codon preferences of many host cells, including *E. coli*, yeast, and other prokaryotes and eukaryotes, are known. See *Maximizing Gene Expression*, pages 225–85. (Reznikoff & Gold, eds., 1986). The codon preferences of other host cells can be deduced by methods known in the art. In particular, the following method is generally used. First, the codon usage in genes coding for about a dozen proteins which are highly expressed in the intended host cell is determined. Then, the codon usage in genes coding for about a dozen proteins expressed at low levels in the host cell is determined. By reviewing the results, codons that are used often and those that are used rarely are identified. The codons that are used most often in highly-expressed genes are preferred. Those used rarely in highly-expressed genes or used in genes expressed at low levels are preferably not used.

The use of chemically synthesized DNA also allows for the selection of codons with a view to providing unique or nearly unique restriction sites at convenient points in the sequence. The use of these sites provides a convenient means of constructing the synthetic coding sequences and facilitates rapid alteration of the sequences by cassette mutagenesis. In addition, if secondary structures formed by the messenger RNA (mRNA) transcript interfere with transcription or translation, they may be eliminated by altering the codon selections.

Chemical synthesis also allows for the use of optimized expression control sequences with the DNA sequences coding for the mutant proteins. In this manner, optimal expression of the mutant proteins can be obtained. For instance, as noted above, promoters can be chemically synthesized and their location relative to the. transcription start optimized. Similarly an optimized ribosome binding site and spacer can be chemically synthesized and used with coding sequences that are to be expressed in prokaryotes.

In prokaryotic mRNA, the site at which the ribosome binds to the messenger includes a sequence of 3–9 purines. The consensus sequence of this stretch is 5'-AGGAGG-3', and it is frequently referred to as the Shine-Dalgarno sequence. The sequence of the ribosome binding site may be modified to alter expression. See Hui and DeBoer, *Proc. Natl. Acad. Sci. USA*, 84, 4762–66 (1987). Comparative studies of ribosomal binding sites, such as the study of Scherer, ez al., *Nucleic Acids Res.*, 8, 3895–3907 (1987), may provide guidance as to suitable base changes.

The ribosome binding site lies 3–12 bases upstream of the start (AUG) codon. The exact distance between the ribosome binding site and the translational start codon, and the base sequence of this "spacer" region, affect the efficiency of translation and may be optimized empirically. To achieve the optimal expression of the mutant proteins of the invention in prokaryotes, a ribosome binding site and spacer that provide for efficient translation in the prokaryotic host cell should be provided. A preferred ribosome binding site and spacer sequence for optimal translation in *E. coli* are described in Springer and Sligar, *Proc. Nat'l Acad. Sci. USA*, 84, 8961–65 (1987) and von Bodman et al., *Proc. Nat'l Acad. Sci. USA*, 83, 9443–47 (1986).

The consensus sequence for the translation start sequence of eukaryotes has been defined by Kozak (*Cell*, 44, 283–292 (1986)) to be: C(A/G)CCAUGG. Deviations from this sequence, particularly at the −3 position (A or G), have a large effect on translation of a particular mRNA. Virtually all highly expressed mammalian genes use this sequence. Highly expressed yeast mRNAs, on the other hand, differ from this sequence and instead use the sequence (A/Y)A (A/U)AAUGUCU (Cigan and Donahue, *Gene*, 59, 1–18 (1987)). These sequences may be altered empirically to determine the optimal sequence for use in a particular host cell.

A host cell capable of expressing a mutant protein according to the invention can be prepared by transforming the cell with a vector comprising a DNA sequence that codes for the mutant protein. Alterna-tively, a DNA molecule coding for a mutant protein may be used to transform the host cell. Methods of transforming cells with vectors or DNA are well known in the art.

Any of a large number of available and well-known host cells may be used in the practice of this invention. The selection of a particular host is de-pendent upon a number of factors recognized by the art. These include, for example, compatibility with the chosen expression vector, toxicity to it of the mutant protein encoded for by the DNA sequence, rate of transformation, expression characteristics, bio-safety and costs. A balance of these factors must be struck with the understanding that not all hosts may be equally effective for the expression of a particular mutant protein.

Within these general guidelines, useful hosts include bacteria (such as *E. coli* sp.), yeast (such as Saccharomyces sp.) and other fungi, insects, plants, animals (including human), or other hosts known in the art.

The mutant proteins of the invention may be produced by culturing the chosen host cell under conditions which permit expression of the mutant protein. Methods of culture and culture media are well known in the art, but the use of enriched media (rather than minimal media) is preferred since much higher yields are obtained.

EXAMPLES

Restriction enzymes used in the following examples were obtained from various commercial sources and used according to the manufacturer's instructions or by employing a standard buffer system (Maniatis et al., *Molecular Cloning: A Laboratory Manual* (1982)).

EXAMPLE 1

Preparation Of Cys36→Ala, Cys97→-Ala Mutant C-Reactive Protein Subunit

This example describes the preparation of a recombinant DNA molecule coding for a mutant human CRP subunit in which the two cysteine residues at positions 36 and 97 (using the numbering system of Woo, et al., *J. Biol. Chem.*, 260, 13384–13388 (1985)) have been replaced with alanine residues. This example also describes the preparation of vectors containing the recombinant DNA molecule operatively linked to expression control sequences and the expression of the mutant CRP subunits in Escherichia coli. Finally, this example describes the properties of the mutant human CRP subunit including, particularly, its ability to bind aggregated immunoglobulin and immune complexes.

A. Replacement Of The Codons For Cysteine-36 And Cysteine-97 In The CRP Coding Sequence Using A Polymerase Chain Reaction Technique To replace codons for cysteine-36 and cysteine-97 in the coding sequence for mature human CRP subunits with codons for alanine, the method of Horton et al., *BioTechniques*, 8, 528–535 (1990) which is based on the polymerase chain reaction (PCR; Saiki et al., *Science*, 239, 487–491 (1988)) was used. Since two independent changes were desired, the process was modified to incorporate a total of five PCR reactions as illustrated in FIG. 1A. Table 1 shows the sequence of the oligonucleotides used as primers in the PCR reactions.

TABLE 1

| Number | Sequence | SEQ ID NO |
|---|---|---|
| 1 | 5'GGGCC*ATA*TGCAGACAGACATGTCGAGG→3'<br>NdeI | 1 |
| 2 | 3'←TCGGAAGTGACAC*CGC*GAAG5' | 2 |
| 3 | 5'CACTGTG*GCG*CTCCAC→3'<br>HhaI | 3 |
| 4 | 3'←GGTCATGTGTA*GCGC*TGTT5' | 4 |
| 5 | 5'CACA*TCGCG*ACAAGCTG→3'<br>NruI | 5 |
| 6 | 3'←GGACTT*CCA*TGGAGTC*TA*GAGCGG5'<br>KpnI    BglII | 6 |

*Italicized* bases indicate restriction enzyme recognition sites.
Bold bases indicate mutagenized codons and the initiator ATG codon.
Underlined bases are complimentary to the CRP cDNA sequence.

As shown in FIG. 1A, the five reactions were: (1) Reaction of cDNA clone coding for preCRP with primers 1 and 2 to produce PCR product A; (2) Reaction of cDNA, coding for preCRP with primers 3 and 4 to produce PCR product B; (3) Reaction of cDNA coding for preCRP with primers 5 and 6 to produce PCR product C; (4) Reaction of products A and B in the presence of primers 1 and 4 to produce PCR product D1; and (5) Reaction of products D1 and C in the presence of primers 1 and 6 to produce the final product D2. D2 was thought to code for the mature sequence of human CRP subunit (the presequence has been eliminated), except that there was an additional methionine at the N-terminus and cysteines 36 and 97 had been replaced by alanines. This was subsequently found not to be the case (see section F below).

The DNA coding for human preCRP used as the starting material for these PCR reactions was obtained by digestion of pCRP5 with EcoRI to yield linear (noncircular) DNA. A sample of plasmid pCRP5 was obtained from Drs. Bruce Dowton and Harvey Colten of Washington University School of Medicine, St. Louis, Mo. pCRP5 was isolated from a human liver cDNA library as described in Tucci et al., *J. Immunol.*, 131, 2416–19 (1983). The nucleotide sequence of the cDNA of pCRP5 and the amino acid sequence of the preCRP coded for by it are given in Woo, et al., *J. Biol. Chem.*, 260, 13384–13388 (1985). However, as described in detail in section F below, the cDNA of the pCRP5 sample obtained from Drs. Dowton and Colten was found to have a deletion in codon 48.

The PCR reactions were carried out using VENT polymerase (New England Biolabs) to minimize unwanted mutations due to misincorporation of bases, and the PCR reactions were done using 20 cycles, each cycle consisting of: 94° C. for 1 minute; 37° C. ., 42° C. or 60° C. for 1 minute (the annealing temperature depending on the sequence of the primers); and 74° C. for 3 minutes. Following the amplification steps, the reactants were further incubated at 74° C. for 5 minutes to complete the synthesis of double-stranded DNA. Each of the products was purified by agarose gel electrophoresis as described in Horton et al., supra. For the PCR reactions where the template consisted of two overlapping sequences (PCR D1 and PCR D2 in FIG. 1A), the reactants were incubated without primers for 4 cycles to allow the formation of full-length template before normal amplification was carried out.

PCR products were digested with restriction endonucleases HhaI and NruI (see Table 1) to confirm that the products incorporated the desired mutations.

B. Construction Of A Plasmid For The Overexpression Of The Mutant CRP Subunit

The final PCR product D2 was concentrated by filtration through a Centricon 30 apparatus (Amicon, Beverly, MA), and then treated with T4 polynucleotide kinase (Pharmacia, Piscataway, N.J.) and T4 DNA ligase (New England Biolabs, Inc.) as described in Denney et al., *Amplifications*, 4, 25–26 (1990). The resultant material was digested with NdeI and BglII to release the mutant CRP coding sequence, and the released coding sequence was ligated to the expression vector pETV which had been digested with NdeI and BamHI and treated with calf intestinal alkaline phosphatase (Promega, Madison, Wis.). The ligation mixture was used to transform *E. coli* DH5α (Gibco BRL Life Technologies, Inc.), and transformants were screened by minipreps performed as described in Birnboim et al., *Nucleic Acids Res.*, 7, 1513–1523 (1979) to identify the correct plasmid pIT4. A restriction map of pIT4 is provided in FIG. 1B. As shown in FIG. 1B, the mutant CRP coding sequence is under the control of the T7 promoter.

Plasmid pETV is a derivative of pET3a. The preparation of pET3a is described in Rosenberg et al., *Gene*, 56, 125–135 (1987). Plasmid pET3a was obtained from Dr. W. Studier, Brookhaven National Laboratory, Upton N.Y. Plasmid pET3a has two NheI restriction enzyme sites. One is located at the T7 gene 10 translation start site in which it was desired to insert the mutant CRP coding sequence. The second NheI site is located within a 190-bp fragment bounded by EcoRV sites. This second NheI site was eliminated by digestion with EcoRV and recircularizing the plasmid to yield pETV.

The predicted sequence of the junction between the expression system of pETV and the coding region for mutant CRP subunit, in pIT4 was confirmed by DNA sequencing as follows. Plasmid pIT4 was digested with XbaI and KpnI, and the relevant fragment subcloned into M13mp18RF (Yanisch-Perron et al., *Gene*, 33, 103–119 (1985)). Single-stranded DNA was obtained from cultures carrying M13 mp18RF and sequenced as described by Sanger et al., *J. Mol. Biol.*, 94, 441–558 (1975) using Ian Applied Biosystems Model 370A Automated DNA Sequencer.

C. Expression And Purification Of The Mutant CRP Subunit

Plasmid pIT4 was used to transform *E. coli* BL21(DE3) (preparation described in Studier et al., *J. Mol. Biol.*, 189, 113–130 (1986)) which carries the phage T7 RNA. polymerase gene under expression control of the lacUV5 operator and promoter. Competent *E. coli* BL21 (DE3) was obtained from Novogen, Madison, Wis. Transformants were selected on LB medium (Miller, *Experiments In Molecular Genetics* (1972)) containing 50 µg/ml ampicillin.

Transformed cells were grown in M9ZB medium (Studier et al., *J. Mol. Biol.*, 189, 113–130 (1986)) containing 100 µg/ml ampicillin at 37° C. for small-scale experiments. Ten-liter cultures were grown in a New Brunswick Microgen SF-116 fermentor in 2YT medium (Miller, *Experiments In Molecular Genetics* (1972)) plus 0.4% (w/v) glucose and 100 µ/ml ampicillin at 37° C. with aeration using compressed air at a rate of 10 liters per minute.

Synthesis of the T7 RNA polymerase, and consequently of the, mutant CRP subunit, was induced with 1 mM (final concentration) isopropyl-beta-D-thio-galactoside (IPTG; Boehringer Mannheim) when the cell density reached $OD_{600}=4$. The cells were harvested 3 hours after induction by rapidly mixing the culture with an equal volume of, ice, concentrating the cells by filtration using a, Millipore Pellicon apparatus equipped with a Durapore 0.5 µM membrane, and centrifuging the cells in a Beckman JA10 rotor at 10,000 rpm for 20 min.

The harvested cells were suspended in 2 mM Tris-HCl, pH 7.5, containing 5 mM EDTA (40 g in 500 ml) and disrupted by three passages through a Manton-Gaulin homogenizer at 10,000 psi. The extract was centrifuged in a Beckman JA10 rotor at 8,000 rpm for 20 min. at 2° C. The pellet containing the insoluble mutant CRP subunits was washed twice with 20 ml of the same buffer containing 0.5% (v/v) Triton X-100 (Bio-Rad), followed by centrifugation in a JA18 rotor at 9,000 rpm for 20 min. to remove the soluble material.

About 5–6 mg of the final pellet were resuspended in 50–70 ml of 8M ultra-pure urea (Boehringer Mannheim, Indianapolis, Ind.) in 10 mM Tris-HCl, pH 7.5–8.0, and incubated at 4° C. overnight with mixing to solubilize the mutant CRP subunits (this material is referred to hereinafter as "mutant rCRP inclusion body preparation"). Next, this material was diluted with 10 mM Tris-HCl, pH 7.5–8.0, to a final concentration of 6M urea and then loaded onto a column containing 40 cc of Q-Sepharose Fast Flow$^R$ anion exchange resin (Pharmacia) at 6 ml per minute. Bound materials were eluted with a linear NaCl gradient using 10 mM Tris-HCl, pH 7.5–8.0, containing 6M urea and 1 M NaCl. Absorbance at 280 nm was measured using a BioPilot$^R$ automated chromatography system (Pharmacia), and an elution profile was obtained.

For comparison, native CRP, mCRP and the primary translation product of a CRP cDNA clone (hereinafter "wild-type rCRP") were also chromatographed on Q-Sepharose Fast Flow$^R$. Native CRP, mCRP and wild-type rCRP were prepared and chromatographed as follows.

Native CRP was isolated from pleural or ascites fluid by calcium-dependent affinity chromatography using phosphorylcholine-substituted BioGelA 0.5 m (an agarose-based resin obtained from BioRad Laboratories) as described by Volanakis, et al. [*J. Immunol.*, 113, 9–17 (1978)] and modified by Potempa, et al. [*Mol Immunol.*, 24, 531–41 (1987)]. Briefly, the pleural or ascites fluid was passed over the phosphorylcholine-substituted column, and the CRP was allowed to bind. Then, the column was exhaustively washed with 75 mM Tris-HCl-buffered saline (pH 7.2) containing 2 mM CaCl$_2$ until the absorbance at 280 nm was less than 0.02. The CRP was eluted with 75 mM Tris, 7.5 mM citrate-buffered saline (pH 7.2). This high concentration of Tris significantly reduces non-specifically adsorbed proteins which often contaminate affinity-purified CRP preparations. CRP-containing fractions were pooled, diluted three-to-five fold with deionized water, adsorbed to Q-Sepharose Fast Flow$^R$ ion exchange resin, and then eluted with a linear salt gradient of from 0–1 M NaCl in 10 mM Tris-HCl, pH 7.4. CRP-containing fractions were pooled and re-calcified to 2–5 mM CaCl$_2$ (by adding a suitable amount of a 1M solution) and applied to unsubstituted Biogel$^R$ A 0.5 m column to remove residual serum amyloid P component (SAP). Then, the CRP was concentrated to 1 mg/ml using ultrafiltration (Amicon; PM30 membrane) under 10–20 psi nitrogen. A CRP extinction coefficient (mg/ml) of 1.98 was used to determine concentration. Next, the concentrated CRP was exhaustively dialyzed against 10 mM Tris-HCl-buffered saline, pH 7.2, containing 2 mM CaCl$_2$. This preparation produced a single Mr 23,000 band on SDS-PAGE electrophoresis and was more than 99% free of SAP, IgG and all other proteins tested for antigenically.

For the Q-Sepharose Fast Flow$^R$ column, 5 ml of the final concentrated CRP solution containing 5 mg of purified native CRP was diluted in about 30 ml of 10 mM Tris-HCl, pH 7.4, and the resulting solution loaded on the Q-Sepharose Fast Flow column at 6 ml per minute. Bound material was eluted with a linear NaCl gradient using 10 mM Tris-HCl, pH 7.4, containing 1 M NaCl. $A_{280}$ was measured using the BioPilot$^R$ automated chromatography system.

To make mCRP, purified native CRP, prepared as described above, at 1 mg/ml was incubated in 8M ultra-pure urea in the presence of 10 mM EDTA for one hour at 37° C. For the Q-Sepharose Fast Flow$^R$ column, 6 ml of this material containing 6 mg of the mCRP was diluted in about 30 ml of 10 mM Tris-HCl, pH 7.5–8.0, containing 6M ultra pure urea, and the resulting solution was loaded on the Q-Sepharose Fast Flow$^R$ column at 6 ml per minute. Bound material was eluted with a linear NaCl gradient using 10 mM Tris-HCl, pH. 7.5–8.0, containing 6M urea and 1 M NaCl. $A_{280}$ was measured using the BioPilot$^R$ automated chromatography system.

Figure 2A:
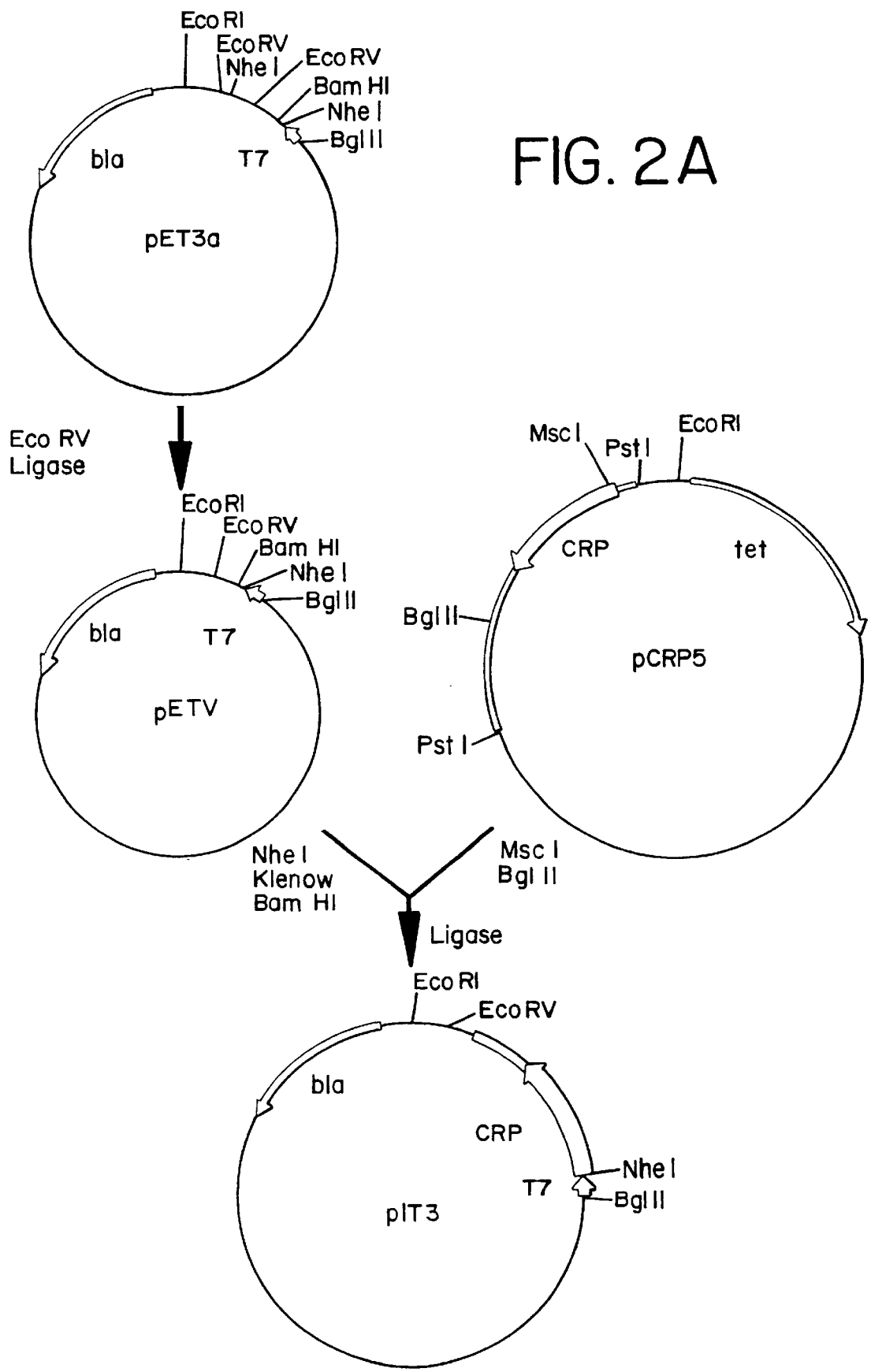
FIGS. 2A and 2B illustrate the preparation of plasmid pIT3.
Figure 2B:
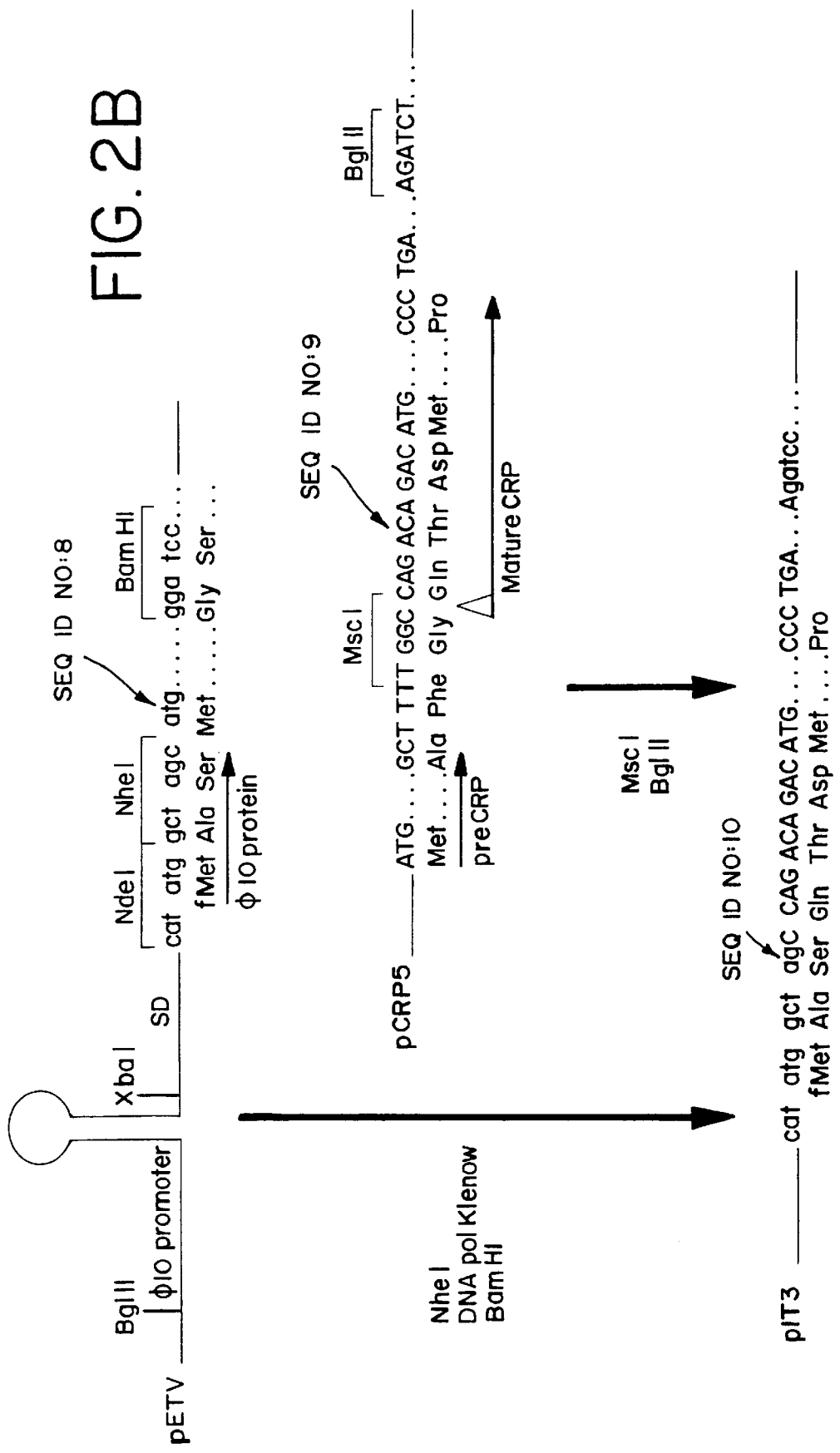

The wild-type rCRP was prepared by expression of pIT3 in *E. coli* BL21(DE3). Plasmid pIT3 was prepared by cleaving pCRP5 with MscI and BglII (see FIG. 2A). Next, pETV was cleaved with NheI and BamHI, and the digested pETV and pCRP5 were mixed and ligated (see FIG. 2A). This, ligation mixture was used to transform *E. coli* strain DH5α and colonies carrying the desired expression plasmid pIT3 were identified, all as described above for pIT4. Plasmid pIT3 was thought to code for a CRP subunit having the sequence of the unmutated human CRP subunit, except that it has the peptide Met Ala Ser at the N-terminus (see FIG. 2B). However, this was subsequently found not to be the case (see section F below). *E. coli* BL21(DE3) were transformed with pIT3 and cultured as described above for pIT4. The cultures were induced, the cells were harvested, and a pellet containing the wild-type rCRP was obtained, all as described above. About 7.4 mg of the pellet were resuspended in 50–70 ml of 8M urea in 10 mM Tris-HCl, pH 7.5–8.0, and incubated at 4° C. overnight with mixing (this material is referred to hereinafter as "wild-type rCRP inclusion body preparation"). The solubilized inclusion body preparation was passed through filter paper to remove non-solubilized debris. Next, this material was diluted with 10 mM Tris-HCl, pH 7.5–8.0, to a final concentration of 6M ultra pure urea and then loaded onto the Q-Sepharose Fast Flow$^R$ column at 6 ml per minute. Bound materials were eluted with a linear NaCl gradient using 10 mM Tris-HCl, pH 8.0, containing 6M urea and 1 M NaCl. $A_{280}$ was measured using the Biopilot$^R$ system.

The elution profiles generated by the BioPilot$^R$ system for native CRP, mCRP, wild-type rCRP and the mutant CRP subunits are shown in FIGS. 3A–D. The BioPilot$^R$ system was programmed so that the salt gradient used in each case could be directly compared.

Figure 3C:
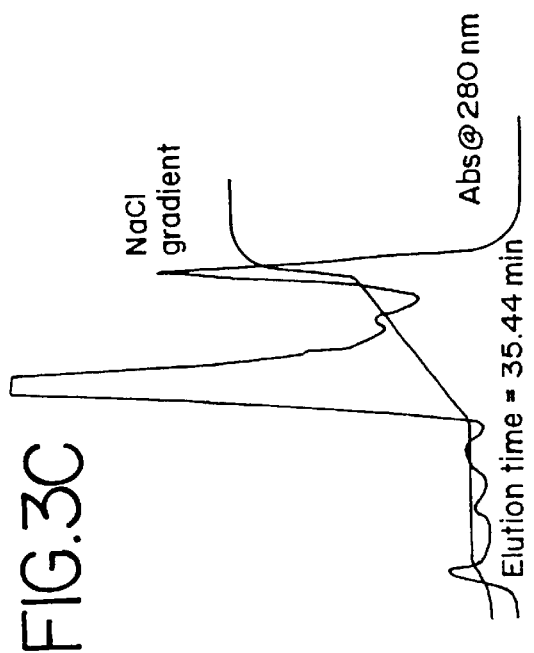
FIGS. 3A–D are elution profiles of materials chromatographed on a Q-Sepharose Fast Flow$^R$ (Pharmacia) column.
Figure 3D:
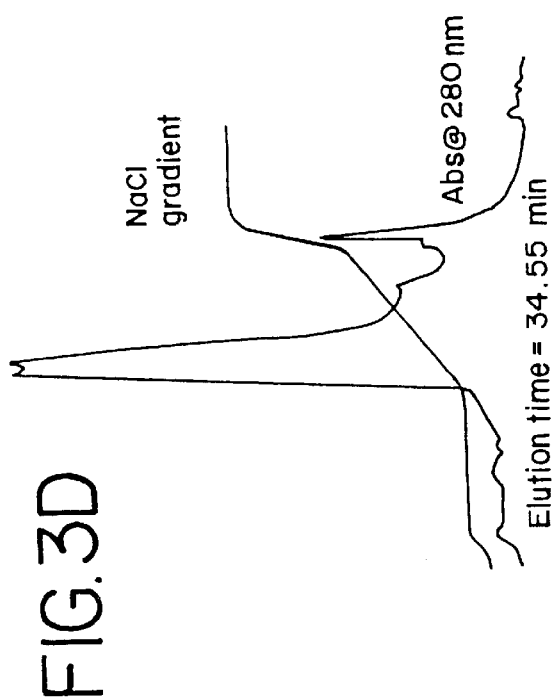
Figure 3A:
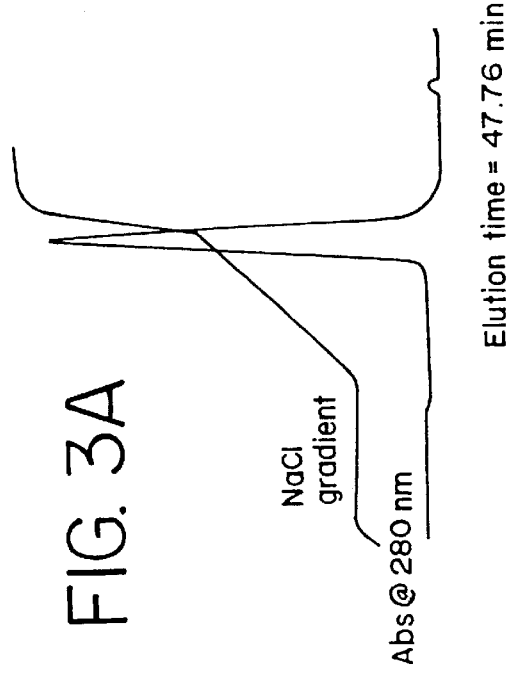

As shown in FIG. 3A, native CRP gave only one significant elution peak. It had an elution time of 47.76 minutes. This peak was dialyzed against 25 mM Tris-HCl, 0.15M NaCl, 2 mM CaCl$_2$ pH 7.4, and then concentrated to about 1 mg/ml using Amicon filtration for testing as described in the next section. The concentrated peak material is referred to hereinafter as "native-CRP$_Q$".

Figure 3B:
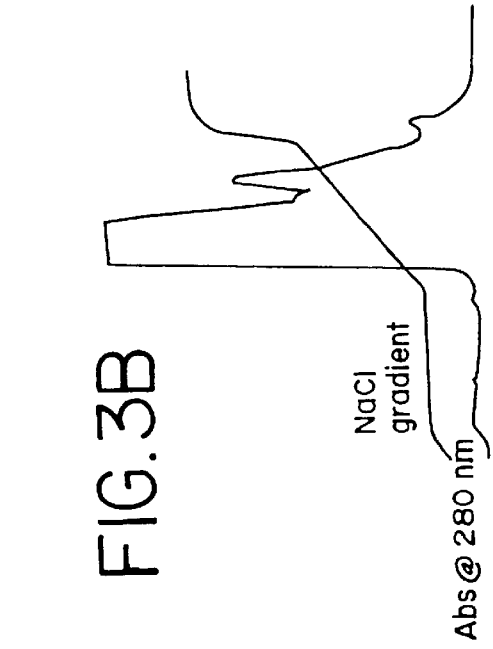

FIG. 3B shows the elution profile for mCRP. The predominant peak has an elution time of 36.18 minutes. This peak was dialyzed against low ionic strength buffer (25 mM Tris-HCl, 0.015 M NaCl, pH 7.4) and then concentrated using Amicon filtration and was tested as described in the next section. The concentrated peak material is referred to hereinafter as "mCRP$_Q$". The testing described in the next section verified that the material in the peak was mCRP. Hence, mCRP elutes from Q-Sepharose$^R$ much earlier (approximately 11.5 minutes earlier) than native CRP.

FIG. 3C shows the elution profile for wild-type rCRP. The predominant peak eluted at 34.55 minutes, an elution time almost identical to that of mCRP and very distinct from the elution time of native CRP. The protein in the predominant peak was dialyzed against low ionic strength buffer and then concentrated using Amicon filtration for further testing as described in the next section. The concentrated peak material is referred to hereinafter as "wild-type rCRP$_Q$".

Finally, FIG. 3D shows the elution profile for the mutant CRP subunits. The main peak eluted at 34.55 minutes, an elution time essentially identical to that of wild-type rCRP and mCRP, and distinct from that of native CRP. The main peak was dialyzed against low ionic strength buffer and then concentrated using Amicon filtration for further testing as described in the next section. The concentrated peak material is referred to hereinafter as "mutant rCRP$_Q$".

Proteins may also be eluted from the Q-Sepharose Fast Flow$^R$ column with an NaCl step gradient (from 0.1 to 1.0 M NaCl). When the recombinant mutant CRP protein was run on the column and eluted with a step gradient, the $A_{280}$ readings showed that most of the protein was eluted from the column with 0.1–0.2 M NaCl. When native CRP was run on the column and eluted with a step gradient, the $A_{280}$ readings showed that most of the protein eluted with 0.4 M NaCl.

D. Characterization Of The Fractions Eluted From The O-Sepharose Fast Flow$^R$ Column The peaks from the Q-Sepharose Fast Flow$^R$ column were analyzed by dot blot, Western blot, SDS-PAGE and ELISA. Wild-type rCRP and mutant rCRP inclusion body preparations were sometimes also tested. Native CRP and mCRP were sometimes used as controls. The preparation of all of these materials is described in the previous section.

1. Dot Blot Assays

Following a modification of the procedure of Zhang, J. Immunol., 138, 575 (1987), nitrocellulose membranes (Schleicher & Schuell, Keene, NH) were pre-soaked in TBS (25 mM Tris-HCl, 0.15M NaCl, pH 7.4) for 30 min., and excess buffer was removed with filter paper. The membranes were then fitted into a Bio-Dot™ microfiltration apparatus (Bio-Rad). Aliquots (50 $\mu$) of the various test proteins at 5 $\mu$g/ml were dotted onto the membrane, incubated overnight at 4° C., and then vacuum-filtered to remove all of the liquid from the wells. Blocking solution. (100 $\mu$l of 1% BSA in TBS) was added to the wells and incubated for 30 min. at room temperature (RT), and vacuum-filtered through the membrane. The wells were washed: three times with TBS containing 1% BSA and 0.05% Tween 20 (TBS washing buffer). Mouse monoclonal antibody (mAb) 3H12 and antiserum LP3-HRP were added and incubated for 30 min. at RT followed by washing. Monoclonal antibody 3H12 was used unlabeled, and the blots were developed by adding rabbit anti-mouse IgG F(ab')$_2$ labeled with horseradish peroxidase (Southern Biotechnology Associates, Birmingham, Ala.), incubating for 30 min. at RT, adding peroxidase substrate 4-chloro-2-naphthol (Bio-Rad) in 10 mM Tris-HCl, 0.15 M NaCl, containing methanol and $H_2O_2$ prepared as directed (Bio-Rad), and incubating for 30 min. at; RT to allow for color development. LP3-HRP was labeled with horseradish peroxidase, and the blots were developed by adding 4-chloro-2-naphthol followed by an incubation for 30 min. at RT for color development.

Monoclonal antibody 3H12 is an IgG antibody specific for an antigenic determinant found on mCRP but not on native CRP. Its preparation and properties are described in U.S. Pat. No. 5,272,257, PCT application WO 91/00872, Ying et al., J. Immunol., 143, 221–228 (1989) and Ying et al., Mol. Immunol., 29, 677–87 (1992). Antiserum LP3 is an antiserum prepared by immunizing a goat with mCRP in complete Freund's adjuvant and then affinity-purifying the harvested antiserum by passing it over a column of cyanogen bromide-activated BioGel$^R$ substituted with mCRP. The resulting affinity-purified anti-neoCRP antiserum LP3 was monospecific for the neo-CRP antigenicity expressed by mCRP but not by native CRP. LP3 was labelled with horseradish peroxidase as described in Potempa et al., Molec. Immunol., 24, 531–541 (1987).

The dot blots showed that mCRP, MCRP$_Q$, wild-type rCRP$_Q$ and mutant rCRP$_Q$ reacted with monoclonal antibody 3H12 and monospecific anti-neoCRP LP3-HRP, indicating that all of these materials express antigenic determinants found on mCRP but not on native CRP. Native CRP and native-CRP$_Q$ did not react with antibodies 3H12 and LP3-HRP as expected.

2. Western Blot

The peaks were also analyzed by Western blot. To perform the Western blot, 5–10 $\mu$l of the peak concentrates were electrophoresed on 12% SDS-PAGE gels under reducing and non-reducing conditions. After electrophoresis, protein was transferred to a nitrocellulose membrane using the JKA Biotech (Denmark) Semidry Electroblotter. The remainder of the procedure was the same as described above for the dot blot, except that three mouse mAbs (3H12, 2C10 and 8C10) were used. The color was developed as described in the previous section for 3H12.

Monoclonal antibody 3H12 is described above. Monoclonal antibody 8C10 reacts with a determinant found only on mCRP, whereas 2C10 reacts with a determinant found on both native CRP and mCRP. The preparation and properties of 2C10 and 8C10 are described in U.S. Pat. No. 5,272,257, PCT application WO 91/00872, Ying et al., J. Immunol., 143, 221–228 (1989) and Ying et al., Mol. Immunol., 29, 677–87 (1992).

The Western blot results showed that mCRP, mCRP$_Q$, wild-type rCRP$_Q$ and mutant rCRP$_Q$ reacted with all three mAbs, indicating that all of these materials express antigenic determinants found on mCRP. Native CRP and native-CRP$_Q$ reacted with mAb 2C10, but not with mAb 3H12 and 8C10, confirming that these materials were native CRP and the antibodies were reacting as expected.

The Western blot results also indicated that the predominant material present in mutant rCRP$_Q$ (the major peak obtained when the mutant CRP subunits were chromatographed on Q-Sepharose Fast Flow$^R$) was free, monomeric subunits. Some multimers and fragments reactive with the antibodies specific for mCRP determinants were present, but the number of such undesired bands was much fewer than was observed with wild-type rCRP$_Q$. This indicates that by replacing the cysteine residues in a CRP subunit, the resultant recombinant product can be more efficiently processed to give a purer, more well-defined product.

3. SDS-PAGE

The peak concentrates were run on PhastGel$^R$ SDS-PAGE gels. (Pharmacia). A gradient of 8–25% acrylamide was used. After the electrophoresis was complete, the gels were stained with Coomassie blue.

Figure 4:
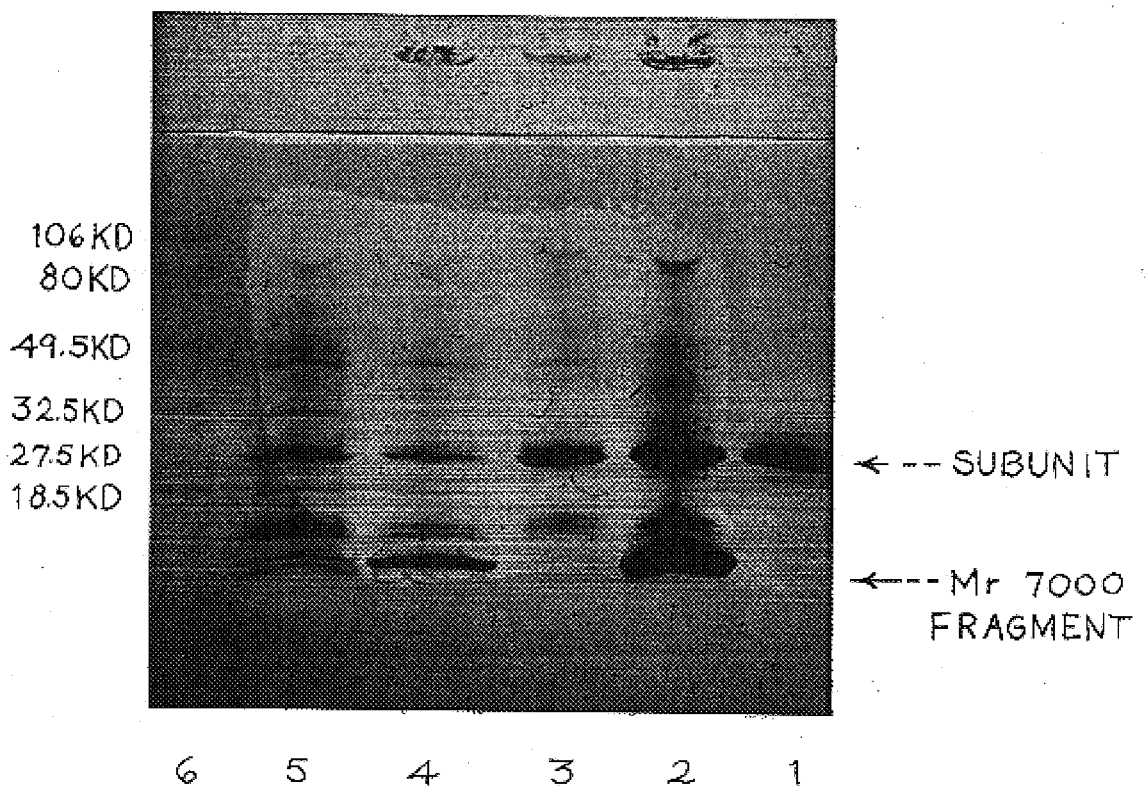
FIG. 4 is a PhastGel$^R$ SDS-PAGE gel (Pharmacia) which has been stained with Coomassie blue.

The results are shown in FIG. 4. In FIG. 4, lane 1 contains mCRP. A single band at approximately 27,000 molecular weight was obtained.

Lane 2 contains the mutant rCRP inclusion body preparation. Note: that there are two predominant bands, including one at approximately the same position as the single mCRP band (Mr of about 27,000). This band was verified by Western blot analysis to be antigenically reactive with antibodies specific for mCRP determinants.

Lane 3 contains mutant rCRP$_Q$ (the mutant rCRP inclusion body preparation which had been chromatographed on Q-Sepharose Fast Flow$^R$). Note that only one major band was obtained having a molecular weight of approximately 27,000, the molecular weight of the desired free mutant CRP subunits. As can be seen, there are many fewer bands as compared to the mutant rCRP inclusion body preparation (lane 2), and the amounts of remaining contaminants, especially the one predominant contaminant having Mr less than 18,000, have been substantially reduced. Thus, the purity of the mutant CRP subunit was greatly improved by the single-step Q-Sepharose Fast Flow$^R$ chromatography procedure.

Lane 4 contains wild-type rCRP inclusion body preparation. As can be seen, multiple protein bands are present. The band approximately 80% down the lane is believed to :be the free subunit (Mr of about 21,000). Note that it is not the predominant band, with the band at the bottom of the lane being of greater intensity.

Lane 5 contains wild-type rCRP$_Q$ (the wild-type rCRP inclusion body preparation which had been chromatographed on Q-Sepharose Fast Flow$^R$). As can be seen, multiple bands are still present as compared to the unchromatographed inclusion body preparation (lane 4). Indeed, some new bands have appeared (at approximate molecular weights of 45,000 and 14,000), the identity of which is unknown, and the intensity of some bands has increased. Thus, no improvement in purification of wild-type rCRP was achieved using the Q-Sepharose Fast Flow$^R$ column. The band about 80% down the lane is believed to be the free subunit. This band and many of the other bands were reactive with the antibodies specific for mCRP determinants by Western blot analysis. This indicates that most of the protein recovered after chromatography of wild-type rCRP preparations on the Q-Sepharose Fast Flow$^R$ column is wild-type rCRP, but that there are problems of multimerization and fragmentation.

Lane 6. contains Prestained BioGel$^R$ molecular weight standards; (BioRad). From top to bottom, these bands are of approximate molecular weight 106,000, 80,000, 49,500, 32,500, 27,500 and 18,500.

4. ELISA

Finally, an ELISA was performed to detect binding of antibodies specific for native CRP and mCRP to the materials in the peaks eluted from the Q-Sepharose Fast Flow$^R$ columns. A direct binding ELISA was used for mCRP and recombinant CRP preparations. A ligand capture ELISA was used for native CRP preparations.

In the direct ELISA, 100 μl of each test protein (5 μg/ml): in 50 mM sodium bicarbonate buffer (pH 9.5) were placed in the wells of Nunc polystyrene plates (Scientific Supply, Shiller Park, Ill.) and incubated for 2 hr at 37° C. or 4° C. overnight. The wells were blocked with TBS (25 mM Tris-HCl, 0.15M NaCl, pH 7.4) containing 1% bovine serum albumin (BSA) (TBS-A) for 60–120 min. at 37° C. The wells were washed with TBS containing 0.05% Tween 20 (TBS-wash buffer). Antibodies were serially diluted with TBS-A, and 100 μl aliquots were added to the wells and incubated for 60 min. at 37° C., followed by washing. Peroxidase-conjugated rabbit anti-mouse IgG (Southern Biotech) in TBS-A was added to the wells for 60 min. at 37° C. After washing, 100 μl ABTS substrate (2–2' azino-bis (3-ethylbenzylthiazoline-6-sulfonic acid, Sigma Chemical Co.) were added per well and incubated for about 5–15 min. at RT. Plates were read at an absorbance of 414 nm on a Titertek$^R$ multiskan plate reader (Flow Laboratories, Helsinki, Finland).

For the ligand capture ELISA, plates were incubated with 100 μl/well of PC-KLH (5 μg/ml) in bicarbonate buffer for 2 hr. at 37° C. or overnight at 4° C. Wells were blocked with TBS-A containing 2 mM CaCl$_2$ as described above. After blocking, 100 μl/well of native CRP (5 μg/ml) in TBS-A containing 2 mM CaCl$_2$ were added and incubated for 60 min. at 37° C. After washing, the rest of the assay was performed as described above, except that 2 mM CaCl$_2$ was included in all buffers. PC-KLH is phosphorylcholine (PC) substituted Keyhole Limpet hemocyanin (KLH). It was prepared by incubating KLH (Sigma Chemical Co.) with paranitrophenyl phophorylcholine (Sigma Chemical Co.) diazotized as described by Chesebro and Metzger, *Biochemistry*, 11, 766 (1972). The final derivatization resulted in 28–52 moles PC per Mr of $1 \times 10^{31\ 5}$ KLH.

Figure 5A:
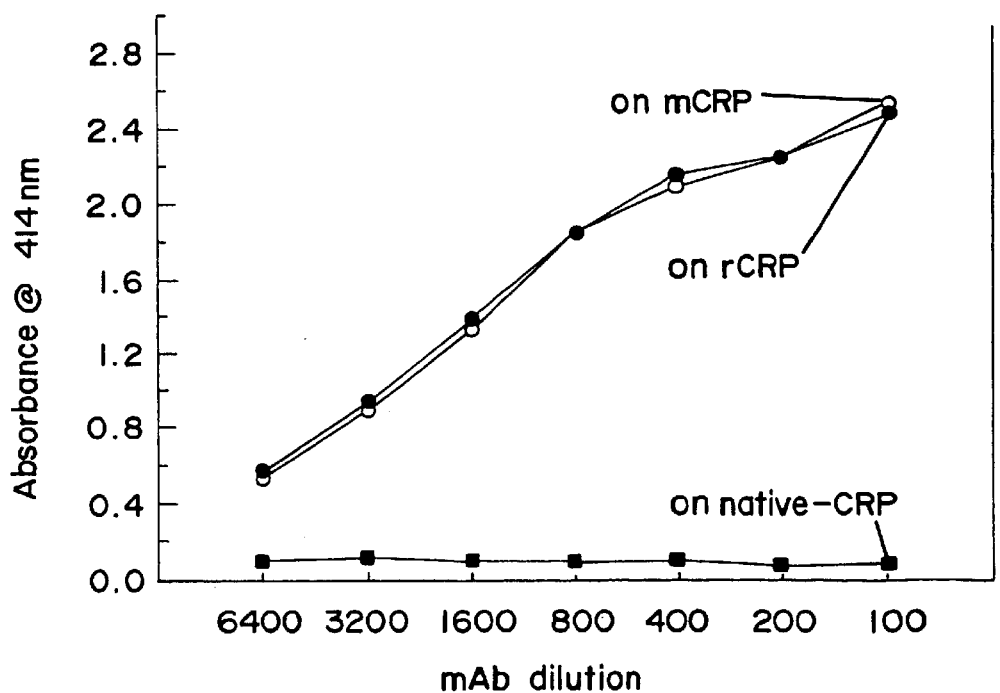
FIGS. 5A–B are graphs of the results of ELISA assays to detect the presence of native CRP and mCRP antigenic determinants on wild-type recombinant CRP.

The results of these ELISAs are shown in FIGS. 5A–D. FIG. 5A shows the reactivity of mCRP, wild-type rCRP inclusion body preparation and native CRP with mAb 3H12. As expected mAb 3H12 reacted with mCRP but not with native CRP. Also, wild-type rCRP inclusion body preparation reacted like mCRP and unlike native CRP, indicating that the mCRP epitope recognized by mAb 3H12 (the carboxy-terminal octapeptide of the CRP subunit) is expressed on wild-type rCRP.

Figure 5B:
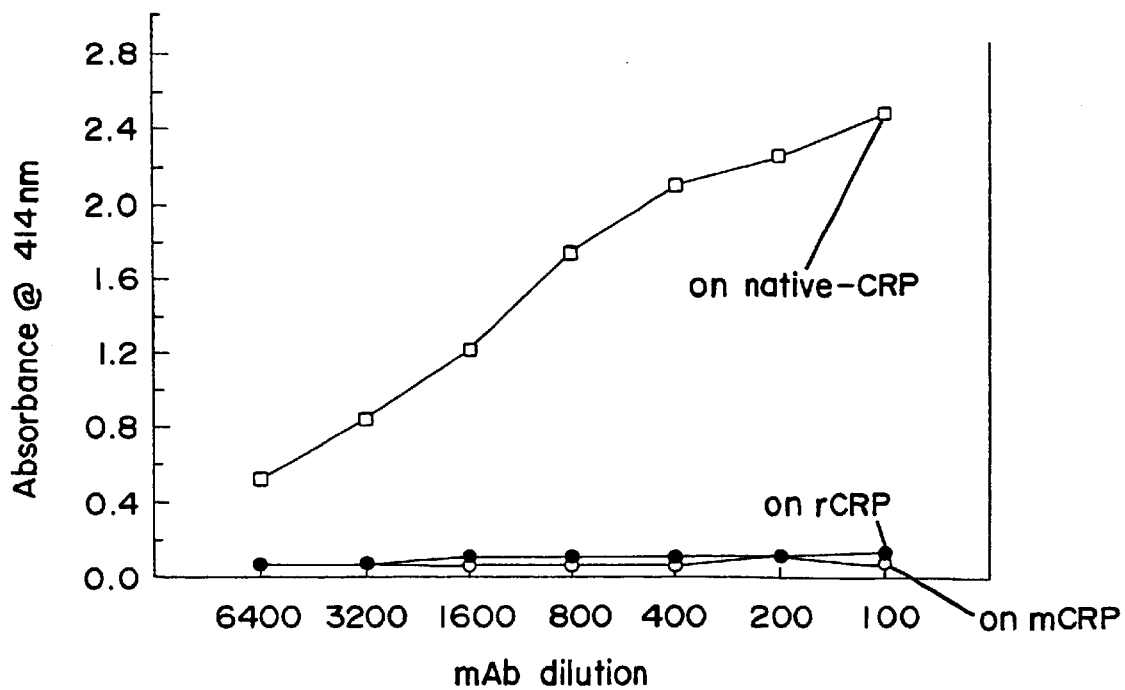

FIG. 5B shows the reactivity of mCRP, wild-type rCRP inclusion body preparation and native CRP with mAb 1D6. Monoclonal antibody 1D6 is specific for an antigenic determinant found only on native CRP. Its preparation and properties are described in U.S. Pat. No. 5,272,257, PCT application WO 91/00872, Ying et al., *J. Immunol.*, 143, 221–228 (1989) and Ying et al., *Mol. Immunol.*, 29, 677–87 (1992). As expected mAb 1D6 reacted with native CRP but not with mCRP. As shown, wild-type rCRP inclusion body preparation, like mCRP, did not react with mAb 1D6, indicating that the native CRP epitope recognized by mAb1D6 is not expressed on wild-type rCRP.

Figure 5C:
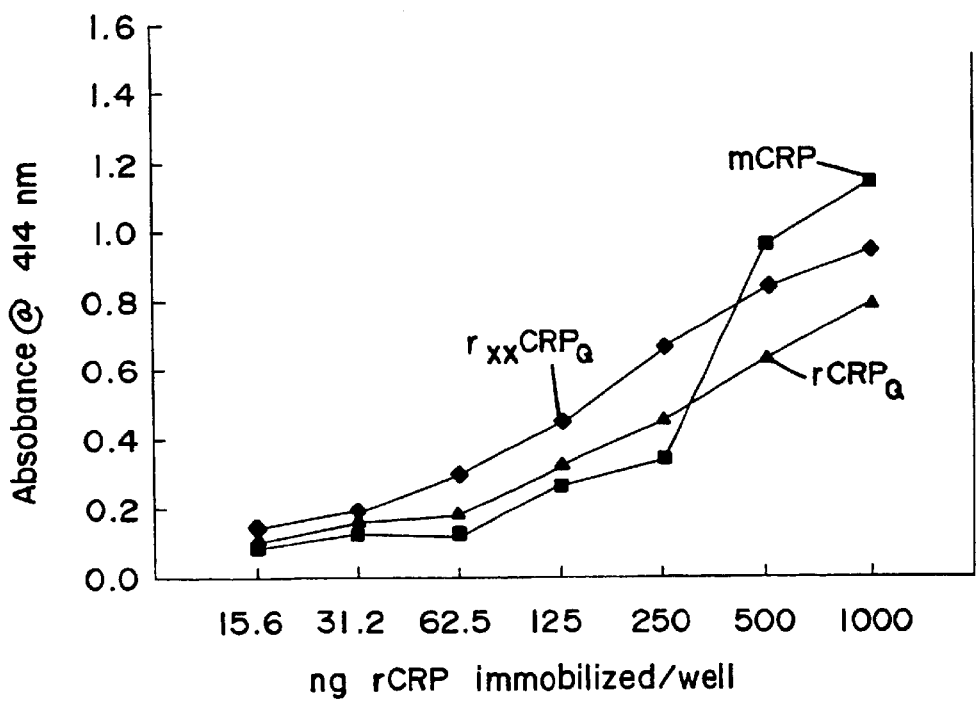
FIGS. 5C–D are graphs of the results of ELISA assays to detect the presence of mCRP antigenic determinants on wild-type recombinant CRP and a mutant protein according to the invention, both of which have been purified by passage over a Q-Sepharose Fast Flow$^R$ column.

FIG. 5C shows the reactivity of mCRP, wild-type rCRP$_Q$ and mutant rCRP$_Q$ with mAb 8C10. Monoclonal antibody 8C10 reacts with an epitope found only on mCRP, but reacts with a different epitope on mCRP than does mAb 3H12. For this ELISA, each test protein was adjusted so that 1000 ng of protein was immobilized on the first well of the polystyrene ELISA plate. The test proteins were then serially diluted so that less and less protein was immobilized per well. The amount of protein that was immobilized per well is indicated on the abscissa of the graph in FIG. 5C. As shown, both wild-type rCRP$_Q$ and mutant rCRP$_Q$ reacted with mAb 8C10 in a manner similar to mCRP. This suggests that the recombinant proteins express an 8C10-specific epitope similar to the one found on mCRP.

Figure 5D:
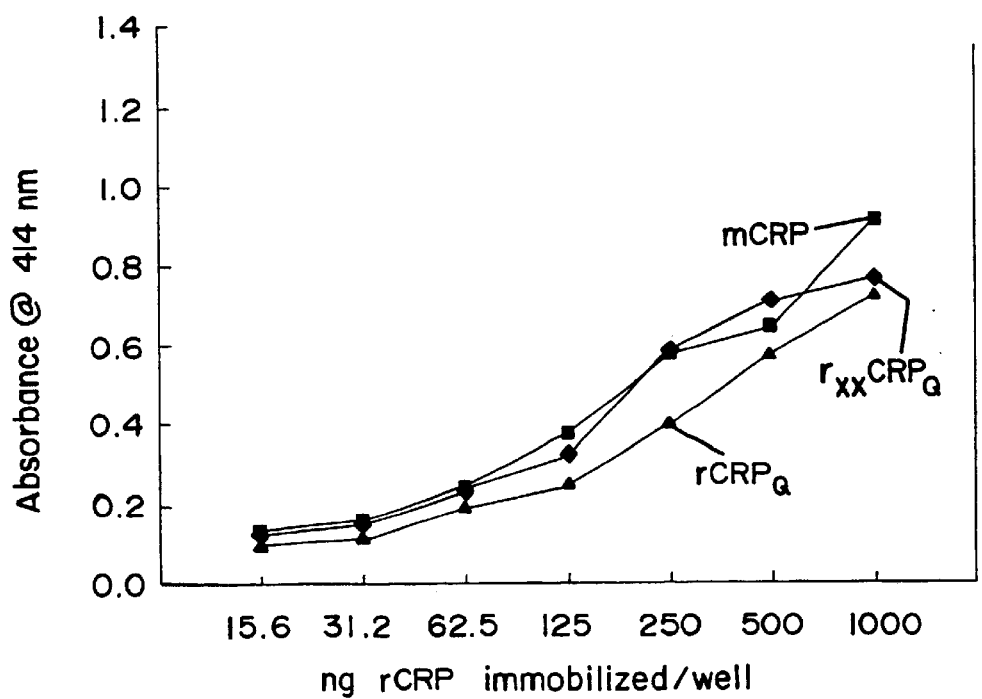

FIG. 5D shows the reactivity of mCRP, wild-type rCRP$_Q$ and mutant rCRP$_Q$ with affinity-purified antiserum LP3-HRP specific for neo-CRP antigenicity. For this ELISA, each test protein was adjusted so that 1000 ng of protein was immobilized on the first well of the polystyrene ELISA plate. The test proteins were then serially diluted so that less and less protein was immobilized per well. The amount of protein that was immobilized per well is indicated on the abscissa of the graph in FIG. 5D. As shown, both wild-type rCRP$_Q$ and mutant rCRP$_Q$ reacted with goat anti-neoCRP LP3-HRP in a manner similar to mCRP. This suggests that the recombinant proteins are antigenicly very similar to mCRP.

E. Evaluation Of The Biological Activity Of The Mutant CRP Subunits

Finally, an ELISA was performed to detect binding to aggregated IgG of the material in the peaks from the Q-Sepharose Fast Flow$^R$ columns. Binding to aggregated immunoglobulins and immune complexes is an important activity of mCRP which permits it to be used to removed aggregated immunoglobulins and immune complexes from fluids and to quantitate immune complexes. This ELISA was performed as follows.

One hundred microliters of each test protein (10 μg/ml) in 10 mM sodium bicarbonate buffer (pH 9.5) were placed in the wells of polystyrene microtiter plates and incubated for B2 hr. at 37° or overnight at 4° C. The wells were blocked with TBS-A for 60–120 min. at 37° C. The wells were washed with TBS wash buffer. Then, 100 41 of aggregated human IgG or monomeric IgG at varying concentrations in TBS-A were added and incubated for 60 min. at 37° C. Human immune globulin (U.S.P. No.-Gammar$^R$, Armour Pharmaceutical Co.) was diluted to 20 mg/ml in buffer at pH 9.0 and was aggregated by heating to 63° C. for about 30 minutes. Non-aggregated monomeric IgG was separated from the aggregated IgG by molecular sieve chromatography using BioGel$^R$ A 1.5 m in 25 mM Tris-HCl, 0.3M NaCl, pH 7.4 at 4° C. After monomeric or aggregated IgG was incubated on test-protein-coated wells, the wells were washed with TBS wash buffer, and 100 μl of peroxidase-conjugated goat anti-human IgG F(ab')$_2$ (Cappel, Durham, N.C.) in TBS-A were added to the wells and incubated for 60 min. at 37° C. After washing, 100 μl ABTS substrate were added per well and incubated for 5–15 min. at RT. Plates were read at an absorbance of 414 nm on a Titertek$^R$ multiskan plate reader.

Figure 6B:
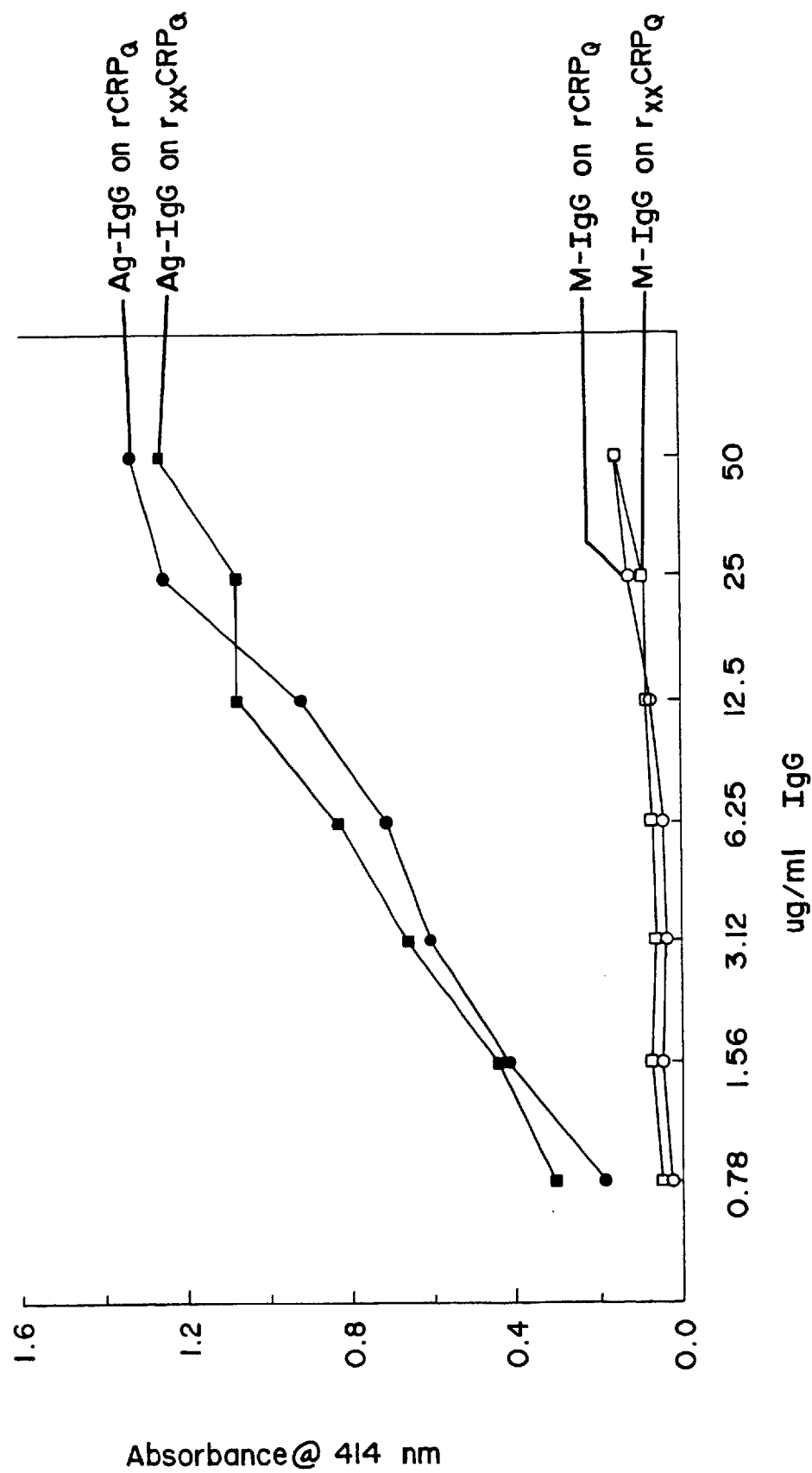

The results are shown in FIGS. 6A–B. As shown in FIG. 6A, wild-type rCRP inclusion body preparation bound aggregated IgG, but not monomeric IgG. Its reactivity was similar to that of mCRP. FIG. 6B shows that both Q-Sepharose-fractionated wild-type rCRP$_Q$ and mutant rCRP$_Q$ bound aggregated IgG, but not monomeric IgG. Hence, both wild-type and mutant recombinant CRPs reacted functionally like mCRP in their capacity to selectively bind aggregated immunoglobulin. Since aggregated immunoglobulin is a standard model for immune complexes, these results also indicate that the mutant proteins of the invention will bind immune complexes and will bind them selectively in the presence of monomeric immunoglobulin.

F. Discovery Of A Deletion In Codon 48 And Preparation Of A Clone Having The Correct Sequence Although rCRP (wild type and mutant) expression was obtained using E. coli BL21(DE3), the level of rCRP produced was considerably lower than has been reported in the literature for other proteins using the T7 RNA polymerase system employed in E. coli. BL21(DE3). Possible reasons for this low level of expression were explored, and it was noted that a fragment of ~7000 Mr was consistently observed as a product (see FIG. 4). Western Blot analysis (performed as described in section G below) using mono-specific goat anti-neo-CRP antiserum labeled with horseradish peroxidase (LP4-HRP) showed that this fragment was related to mCRP antigenically. LP4-HRP was prepared as described in section D above for LP3-HRP, but using a different goat than used to prepare LP3-HRP. N-terminal sequence analysis of the purified fragment confirmed that the fragment contained the expected CRP sequence from residues 1 to 6. The N-terminal sequence analysis was performed by Analytical Biotechnology Services (Boston, MA) using automated Edman degradation on an Applied Biosystems Model 477A protein sequencer. The Mr 7000 fragment used for the N-terminal sequencing was purified as follows. The concentration of protein in an inclusion body suspension (prepared as described in section H below) was estimated using the Bicinchoninic Acid protein assay (Pierce Biochemicals). Inclusion body protein was then solubilized in 6 M guanidine HCl (GuHCl; J. T. Baker Inc.), 15 mM Tris-Cl, pH 7.2, 10 mM EDTA at a concentration of 4: mg protein/ ml. Ammonium sulfate was added to 28% saturation, and the precipitated protein collected by centrifugation (10 minutes at 12,000 rpm in a Sorvall GSA rotor). The resulting pellet was washed with TBS (10 mM Tris-Cl, pH 7.4, containing 0.15 M NaCl) and subsequently dissolved in 8M urea, 25 mM sodium acetate, pH 4.0, at a concentration of approximately 1 mg protein/ml as judged by absorbance at 280 nm. This material was passed over an S-Sepharose Fast Flow column (Pharmacia) equilibrated with 6M urea, 25 mM sodium acetate, pH 4.0. The column was then developed with a four-column volume gradient of 0–0.25 M NaCl in the equilibration buffer (6M urea, 25 mM sodium acetate, pH 4.0). The fragment eluted at approximately 0.24 M NaCl. Fractions containing the fragment were pooled and concentrated by precipitation with 50% saturated ammonium sulfate. The precipitate was collected by centrifugation as described above and dissolved in equilibration buffer. The dissolved precipitate was again passed over an S-Sepharose Fast Flow column as described above, except that elution was performed with a 0–0.8 M NaCl gradient.

The size of the fragment and the quantity produced were very consistent from batch to batch. Furthermore, there was little evidence of other fragments, suggesting that the 7000 Mr fragment resulted from incomplete mRNA or protein synthesis rather than from proteolytic degradation.

Accordingly, the DNA coding for the mutant rCRP was sequenced. To do so, the coding sequence was excised from pIT4 using XbaI and KpnI and ligated into pBluescript KS (Stratagene Inc.) previously digested with the same enzymes. The subcloned DNA was sequenced on an Applied Biosystems Sequenator by the dideoxy chain termination method using standard M13-based primers. The DNA sequences of two independent isolates revealed two differences with respect to the published Woo et al. sequence (Woo et al., J. Biol. Chem., 260, 13384–13388 (1985)). First, there was a synonymous substitution (G to A) in the wobble position of codon 152 (as noted above, the numbering system of Woo et al., J. Biol. Chem., 260, 13384–13388 (1985) is being used; this would actually be the 153rd codon of the CRP coding sequence of pIT4 since an ATG start codon was added at the 3' end of the coding sequence (see section A above)). Second, there was a missing T at codon 47. The missing base in is in a GC-rich region, and it was initially thought that the absence of this T from the sequence was due to compression, a common sequencing artifact.

However, the results obtained from C-terminal sequence analysis of the 7000 Mr fragment were consistent with the DNA sequence data. C-terminal sequencing of the purified fragment (prepared as described above) was performed by Analytical Biotechnology Services. Briefly, the fragment was digested with carboxypeptidase Y at a ratio of 5 μg enzyme per 10 nmol protein (based on an estimated molecular weight of 7000). The mixture was incubated at 37° C., and 0.5 nmol aliquots were removed at 0, 30, 60 and 180 minutes and frozen at −20° C. Each aliquot was then subjected to amino acid analysis using the Waters PICO-TAG system. The following residues were released in roughly equal amounts after digestion of the fragment with carboxypeptidase Y: Ser, Tyr, Phe, Gly, Leu, Arg, and Ile. While these amino acids could possibly be assigned to the CRP sequence ending at Phe 52:

```
Leu Ser Ser Thr Arg Gly Tyr Ser Ile Phe
             5                        10
                                  SEQ ID NO:11,
``` the fit is ambiguous because Thr was not detected after the carboxypeptidase Y digestion. In contrast, a missing base at codon 47 would introduce a frameshift resulting in a termi nation codon at position 71. The predicted sequence of the C terminus of this polypeptide would be

```
    Ser Tyr Phe Gly Leu Arg Ile         SEQ ID NO:12,
                  5
``` which is a precise fit to the C-terminal sequence data for the fragment.

Deletion of T at codon 47 would also fortuitously introduce a novel restriction site into the DNA by changing the base sequence from CCCGTGG to CCCGGG, the latter being the recognition sequence for the enzyme SmaI. Analytical digests were therefore performed on pIT3, pIT4 and pCRP5 by digesting 50–100 ng of each plasmid for 2–4 hours at 37° C. with EcoRI, SmaI, KpnI or SmaI and KpnI. The digestion products were separated on 1% agarose gels and visualized with ethidium bromide. All three plasmids were digested with SmaI yielding fragments of the sizes expected if the T in codon 47 were missing. These results further confirm the results of the DNA sequence analysis. These results also demonstrate that the deletion had occurred in the original plasmid pCRP5 and was not a result of the subcloning process described in section A above. No undigested DNA was detectable in any of the plasmid digests.

Finally, a sample of the purified 7000 Mr fragment (purified as described above) was submitted to Analytical Biotechnology Services for complete amino acid composition analysis. Briefly, the protein sample was hydrolyzed in 6 N HCl and derivatized with phenylisothiocyanate. The phenylthiohydantoin-amino acids were detected by high performance liquid chromatography (HPLC). The results are presented in Table 2 below. Once again, the results confirmed that there was a base deletion in codon 47 which introduced a frameshift leading to premature termination of protein synthesis at codon 71.

The analysis of both the plasmid DNA and the Mr 7000 fragment, thus, provided convincing evidence that a base deletion in codon 47 was causing premature termination of translation, and that the deletion had originated in plasmid pCRP5. However, full-length rCRP subunits (wild type and mutant) were being made (see FIG. 4).

A possible explanation for the synthesis of the full-length subunits was suggested by a report in the literature [Tenchini et al., *Inflammation*, 16, 93 (1992)]. Tenchini et al. describe a human CRP CDNA clone which had been isolated and sequenced. It had the base deletion in question in codon 47, but also contained a single base insertion at codon 64 (see Table 3 below). Since the insertion occurs before the termination codon introduced by the deletion, the proper reading frame is restored before protein synthesis is terminated. The net result is a sixteen-amino acid segment of out-of-frame sequence in the middle of the protein.

This segment differs greatly in amino acid composition from the known CRP sequence, so amino acid analyses were performed on the purified wild-type and mutant rCRP produced by pIT3 and pIT4. These proteins were purified as follows. Mutant rCRP was purified using a two-step column procedure. Inclusion body protein was solubilized, fractionated with ammonium sulfate and dissolved in urea as described above for the Mr 7000 fragment. This material was then applied to an S-Sepharose Fast Flow cation exchange column. The column was developed with a 0–0.25 M NaCl gradient in 6M urea, 25 mM sodium acetate, pH 4.0, to removed impurities. After the NaCl concentration was decreased to 0, the mutant rCRP was eluted with 8M GuHCl, 25 mM sodium acetate, pH 4.0. The GuHCl eluate was then applied to a Superdex 200 gel filtration column (Pharmacia) which had been equilibrated with 3 M GuHCl, 4 M urea in 25 mM sodium acetate, pH 4.0. The wild-type rCRP was purified using a similar procedure, except that the S-Sepharose Fast Flow column was omitted and the mobile phase for the Superdex-200 gel filtration chromatography was 25 mM Tris-Cl, pH 8.0, containing 6 M GuHCl and 2 mM dithiothreitol (Pierce Biochemicals). The purified proteins were submitted to Analytical Biotechnology Services for complete amino acid composition analysis. The results (presented in Tables 4a and 4b below) were inconclusive.

Several additional experiments designed to detect the presence of an inserted base in codon 64 were negative. Moreover, the initial DNA sequence analysis of plasmid pIT4 had not detected the insertion of a base in codon 64 (see above). The combined experimental results, therefore, support the conclusion that there is a base deletion in codon 47 and no base insertion prior to stop codon 71.

It is highly unlikely that the full-length rCRP subunits result from occasional read-through of the stop codon 71, since the frameshift due to the deletion in codon 47 introduces a total of nine termination codons into the MRNA. Even if it were possible for the ribosomes to read through all nine stop codons, the frequency of the event should decrease as the number of missed codons increases. This would generate a predictable ladder of products, with the largest being present in the lowest abundance. In contrast, only two predominant species have been observed, the 7000 Mr fragment encoded by the plasmid and the full-length subunit (see FIG. 4).

Many explanations as to the source of the full-length rCRP have been eliminated, and it is now believed that it results from a ribosomal frameshift whereby the ribosome shifts one or two bases during translation of the mRNA so that the proper reading frame is restored. There are many documented examples of such events occurring in *E. coli*, both as natural mechanisms for protein synthesis and as mutations occurring, for example, when an aminoacyl-tRNA is limiting. See, e.g., Weiss et al., *EMBO J.*, 7, 1503–1507 (1988); Tsuchihashi et al., *Proc. Natl. Acad. Sci.*, 87, 2516–20 (1990); Gallant et al., *J. Mol. Biol.*, 223, 31–40 (1992); Sipley et al., *Proc. Natl. Acad. Sci.*, 90, 2315–19 (1993); and Lindsley et al., *Proc. Natl. Acad. Sci.*, 90, 5469–73 (1993). In the present case, the ribosomal frameshift must occur between the T deletion in codon 47 and the stop codon 71 to restore the reading frame and obtain a full-length product. The amino acid sequence of the full-length RCRP coded for by codons 47–71 has been deduced (see section J below).

TABLE 2

| | Mol/mol protein | | | Mole percent | | |
|---|---|---|---|---|---|---|
| | Expected | | | Expected | | |
| | CRP through Phe52 | Mr 7000 Fragment | Obtained | CRP through Phe52 | Mr 7000 Fragment | Obtained |
| Lys | 5 | 5 | 5.6 | 9.4 | 7.0 | 8.68 |
| His | 1 | 1 | 1.0 | 1.9 | 1.4 | 1.54 |
| Arg | 2 | 7 | 5.3 | 3.8 | 9.9 | 8.17 |
| Asx | 3 | 4 | 2.7 | 5.7 | 5.6 | 4.20 |
| Thr | 5 | 7 | 7.6 | 9.4 | 9.9 | 11.76 |
| Ser | 7 | 8 | 7.1 | 13.2 | 11.3 | 10.98 |
| Glx | 3 | 3 | 2.9 | 5.7 | 4.2 | 4.46 |
| Pro | 3 | 5 | 4.6 | 5.7 | 7.0 | 7.05 |
| Gly | 1 | 2 | 2.0 | 1.9 | 2.8 | 3.04 |
| Ala | 4 | 4 | 3.9 | 7.5 | 5.6 | 5.00 |
| Cys | 0 | 0 | 0.1 | 0 | 0 | 0.07 |
| Val | 3 | 4 | 3.5 | 5.7 | 5.6 | 5.43 |
| Met | 2 | 4 | 3.5 | 3.8 | 5.6 | 5.40 |
| Ile | 1 | 1 | 0.9 | 1.9 | 1.4 | 1.38 |
| Leu | 5 | 6 | 5.5 | 9.4 | 8.5 | 8.45 |
| Tyr | 3 | 3 | 2.5 | 5.7 | 4.2 | 3.94 |
| Phe | 5 | 7 | 6.1 | 9.4 | 9.9 | 9.46 |
| Trp | 0 | 0 | | | | |
| Total | 53 | 71 | | | | |

TABLE 3

Amino acid sequence of CRP between residues 46-72 and corresponding DNA sequence:

```
Thr Arg Gly Tyr Ser Ile Phe Ser Tyr Ala Thr Lys Arg Gln Asp Asn Glu Ile Leu Ile Phe Trp Ser Lys Asp Ile Gly       SEQ ID NO:13
              5                        10                       15                       20                    25
ACC CGT GGG TAC AGT ATT TTC TCG TAT GCC ACC AAG AGA CAA GAC AAT GAG ATT CTC ATA TTT TGG TCT AAG GAT ATA GGA    81 SEQ ID NO:14
```

Possible amino acid sequence of Mr 7000 fragment between residues 46-72 assuming deletion only and corresponding DNA sequence:

```
Thr Arg Gly Thr Val Phe Ser Arg Met Pro Arg Asp Lys Thr Met Arg Phe Ser Tyr Phe Gly Leu Arg Ile STOP           SEQ ID NO:15
              5                        10                       15                       20                    25
ACC CGG GGT ACA GTA TTT TCT CGT ATG CCA CCA AGA GAC AAG ACA ATG AGA TTC TCA TAT TTT GGT CTA AGG ATA TAG GA  80 SEQ ID NO:16
```

Tenchini et al. amino acid sequence between residues 46-72 and corresponding DNA sequence:

```
Thr Arg Gly Thr Val Phe Ser Arg Met Pro Arg Asp Lys Thr Met Arg Phe Phe Ile Phe Trp Ser Lys Asp Ile Gly       SEQ ID NO:17
              5                        10                       15                       20                    25
ACC CGG GGT ACA GTA TTT TCT CGT ATG CCA CCA AGA GAC AAG ACA ATG AGA TTC TTC ATA TTT TGG TCT AAG GAT ATA GGA  81 SEQ ID NO:18
```

The nucleotides deleted or inserted are underlined when present.
Amino acids in boldface type are those differing from the sequence of CRP.

TABLE 4a

Amino acid composition of wild type rCRP (pIT3 product)

| | Mol/mol protein | | | Mole percent | | |
|---|---|---|---|---|---|---|
| | Expected | | | Expected | | |
| | Woo + Lei* | Tenchini | Obtained | Woo + Lei | Tenchini | Obtained |
| Lys | 13 | 12 | 11.2 | 6.4 | 5.9 | 5.85 |
| His | 2 | 2 | 2.4 | 0.99 | 0.99 | 1.25 |
| Arg | 6 | 9 | 8.2 | 3.0 | 4.4 | 4.25 |
| Asx | 16 | 15 | 13.8 | 7.9 | 7.4 | 7.21 |
| Thr | 13 | 14 | 14.1 | 6.4 | 6.9 | 7.37 |
| Ser | 22 | 21 | 20.5 | 10.8 | 10.3 | 10.67 |
| Glx | 21 | 19 | 19.7 | 10.3 | 9.4 | 10.20 |
| Pro | 11 | 13 | 13.4 | 5.4 | 6.4 | 7.00 |
| Gly | 17 | 17 | 16.9 | 8.4 | 8.4 | 8.82 |
| Ala | 10 | 9 | 10.6 | 4.9 | 4.4 | 5.55 |
| Cys | 2 | 2 | 5.4 | 0.99 | 0.99 | 1.40 |
| Val | 18 | 19 | 15.8 | 8.9 | 9.4 | 8.25 |
| Met | 3 | 5 | 3.6 | 1.5 | 2.5 | 1.89 |
| Ile | 12 | 10 | 6.4 | 5.9 | 4.9 | 3.32 |
| Leu | 15 | 14 | 15.1 | 7.4 | 6.9 | 7.86 |
| Tyr | 8 | 6 | 5.4 | 3.9 | 3.0 | 2.80 |
| Phe | 14 | 16 | 12.1 | 6.9 | 7.9 | 6.31 |
| Trp | 6 | 6 | | | | |
| Total | 209 | 209 | | | | |

*Sequence reported in Woo et al., J. Biol. Chem. 260, 13384–88 (1985) and Lei et al., J. Biol. Chem., 260, 13377–83 (1985).

TABLE 4b

Amino acid composition of mutant rCRP (pIT4 product)

| | Mol/mol protein | | | Mole percent | | |
|---|---|---|---|---|---|---|
| | Expected | | | Expected | | |
| | Woo + Lei* | Tenchini | Obtained | Woo + Lei | Tenchini | Obtained |
| Lys | 13 | 12 | 11.9 | 6.5 | 6.0 | 6.22 |
| His | 2 | 2 | 2 | 1.0 | 1.0 | 1.05 |
| Arg | 6 | 9 | 7.5 | 3.0 | 4.5 | 3.92 |
| Asx | 16 | 15 | 13.5 | 8.0 | 7.5 | 7.04 |
| Thr | 13 | 14 | 14.2 | 6.5 | 7.0 | 7.45 |
| Ser | 21 | 20 | 19.2 | 10.4 | 10.0 | 10.03 |
| Glx | 21 | 19 | 18.8 | 10.4 | 9.5 | 9.83 |
| Pro | 11 | 13 | 12.9 | 5.5 | 6.5 | 6.77 |
| Gly | 17 | 17 | 16.7 | 8.5 | 8.5 | 8.73 |
| Ala | 11 | 10 | 10.5 | 5.5 | 5.0 | 5.5 |
| Cys | 0 | 0 | 0.2 | 0 | 0 | 0.04 |
| Val | 18 | 19 | 17.3 | 9.0 | 9.5 | 9.04 |
| Met | 3 | 5 | 4.8 | 1.5 | 2.5 | 2.52 |
| Ile | 12 | 10 | 6.5 | 6.0 | 5.0 | 3.38 |
| Leu | 15 | 14 | 14.8 | 7.5 | 7.0 | 7.72 |
| Tyr | 8 | 6 | 6.3 | 4.0 | 3.0 | 3.29 |
| Phe | 14 | 16 | 14.3 | 7.0 | 8.0 | 7.49 |
| Trp | 6 | 6 | | | | |
| Total | 207 | 207 | | | | |

Clearly, the base deletion in codon 47 of the CRP coding sequence of pIT4 was preventing efficient expression of rCRP, and mutagenesis was necessary to correct the sequence. In addition, some other features of the CRP coding sequence were identified which could hinder rCRP expression. One of these is a potential stem-loop structure surrounding the site of the deletion. A second is poor codon usage. The mutagenesis, therefore, had three goals: 1) to re-introduce the missing base into codon 47; 2) to reduce the possibility of MRNA secondary structure; and 3) to replace codons infrequently used in E. coli.

The mutagenic primer was designed with those goals in mind. The target sequence for mutagenesis and the changes to be introduced are shown below. The bold letter indicates the base that was inserted into the site of the deletion (codon 47). The underlined codons (48 and 50) are others that were changed for purposes of increasing expression.

```
TARGET SEQUENCE:
     CC TCG ACC CGG GGT ACA GTA TTT TCT CG      28
               (SEQ ID NO:19)

DESIRED CHANGES:
     CC TCG ACC CGT GGT TAC AGC ATT TTC TCG     29
               (SEQ ID NO:20)
               Gly 48:           Ser 50:
               change codon      change codon
               usage, weaken     usage
               2° structure
```

Figure 7:
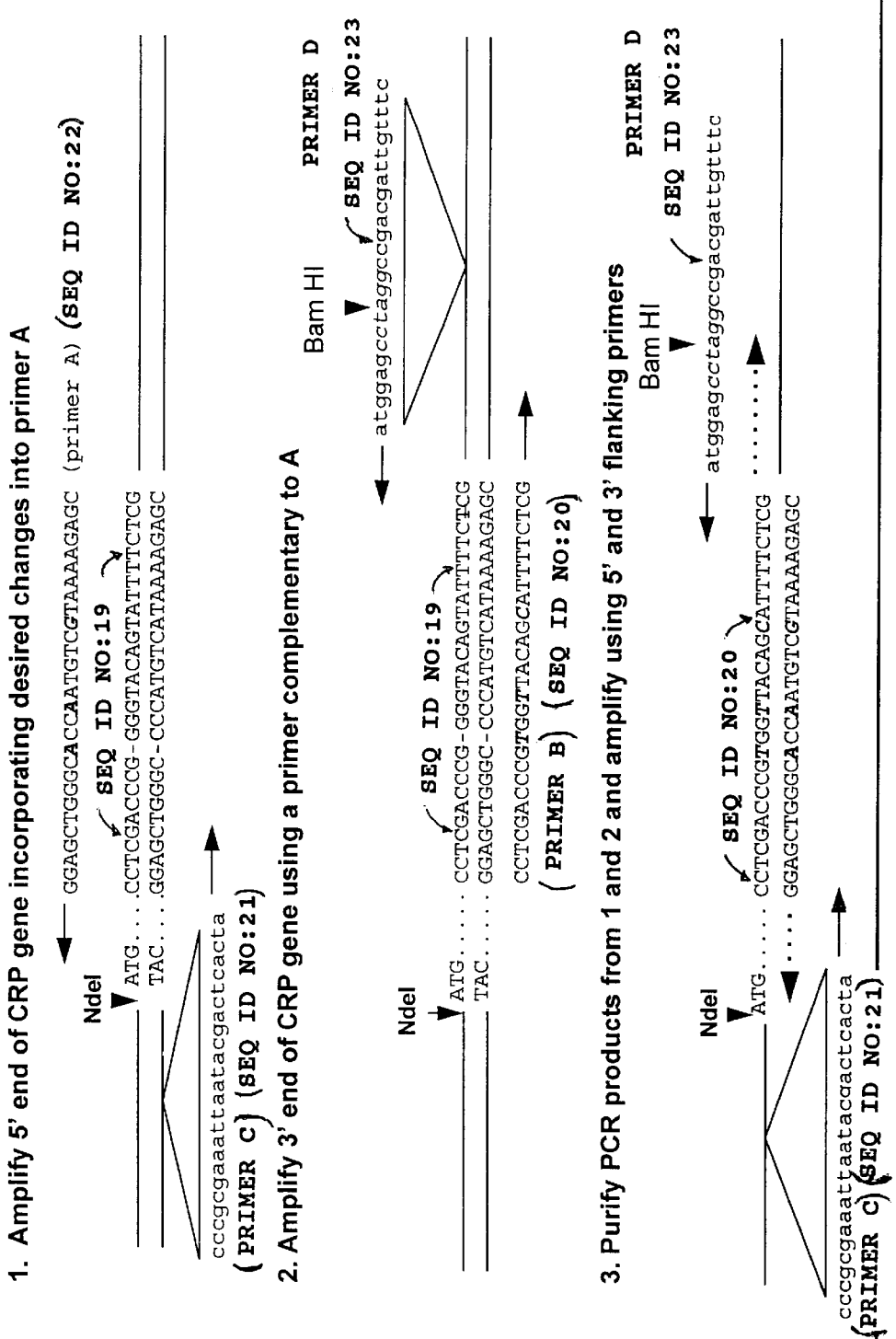
FIGS. 7 is a diagram of a series of polymerase chain reactions.

Complementary oligonucleotide primers spanning the target sequence were synthesized by the phosphoramidite method on an Eppendorf Synostat-D synthesizer using Eppendorf reagents. The sequences of these primers are shown as A and B in Table 5 below. Two additional oligonucleotides (C and D) were synthesized for use as flanking primers. Their sequences and locations relative to the CRP sequence and a schematic diagram of each o if the reactions performed are shown in FIG. 7.

TABLE 5

| Primer | Name | Length | Sequence | Note |
|---|---|---|---|---|
| C | Upstrm 1 | 25 | CCCGCGAAATTAATACGACTCACTA SEQ ID NO:21 | 5' flanking primer |
| B | SmaI upper | 29 | CCTCGACCCGTGGTTACAGCATTTTCTCG SEQ ID NO:20 | Mutagenic primer, puts T in and removes putative stem loop |
| A | SmaI lower | 29 | CGAGAAAATGCTGTAACCACGGGTCGAGG SEQ ID NO:22 | As above, but opposite strand |

TABLE 5-continued

| Primer | Name | Length | Sequence | Note |
|---|---|---|---|---|
| D | BamHI lower | 26 | CTTTGTTAGCAGCCGGATCCGAGGTA SEQ ID NO:23 | 3' flanking primer, introduces Bam HI site |

Reactions 1 and 2 illustrated in FIG. 7 employed 10 nmol of HindIII-linearized pIT4 as template, 10 nmol of each primer, 0.2 mM deoxynucleotide triphosphates (Pharmacia), 10 μl of 10×GeneAmp$^R$ reaction buffer (Perkin Elmer Cetus), and 2.5 units AmpliTaq$^R$ Taq DNA Polymerase (Perkin Elmer Cetus) in a total volume of 100 μl. Reaction buffer contains 50 mM KCl, 10 mM Tris-HCl (pH 8.3), 1.5 mM MgCl$_2$ and 0.001% (w/v) gelatin (final concentrations). Reactions were carried out in a DNA Thermal Cycler Model 480 from Perkin Elmer Cetus. Following a three-minute incubation at 94° C., the unit was programmed to run 20 cycles of 94° C., 1 min.; 50° C., 1 min.; 74° C., 1 min., ending with a 7 min. incubation at 72° C.

PCR products were purified on a vertical 1.6% agarose gel (1.5 mm thick) run in TAE (Tris. Acetate/EDTA). Prior to casting the gel, plates, combs and spacers were soaked in 1 N HCl for 30 minutes to guard against contamination. The appropriate bands were excised and the PCR products purified using a GeneClean II$^R$ kit (Bio101 Inc.) according to the manufacturer's instructions. The DNAs were eluted in a volume of 100μl TE (10 mM Tris-Cl, pH 8.0, 1 mM EDTA). The yields of DNA were estimated from the prep gel.

A second set of PCR reactions was performed to splice together the first-round products, thus restoring the full-length coding sequence. Fifty ng of the 3' product and 20 ng of the 5' product were used as template, and 10 pmol each of primers A and B were used for amplification. Other conditions for the reactions were as in the first round. Four thermal cycles were performed prior to the addition of the primers to give a chance for the extension reaction to begin. After primers were added, the reactions were continued for another 20 cycles.

The vector pETV and the final PCR product were digested with NdeI and BamHI. The fragments were gel-purified using GeneClean. The vector was then treated with calf intestinal alkaline phosphatase. Vector and insert were ligated, and the ligation mixture was used to transform *E. coli* BL21(DE3). Transformants were screened by minipreps performed as described in Sambrook et al., *Molecular Cloning: A Laboratory Manual* (2nd ed., 1989, Cold Spring Harbor Laboratory Press). Analytical digests were performed on the miniprep DNA using SmaI, NdeI and KpnI, NdeI and BamHI, and XbaI and HindIII. The products were separated on a 1% agarose gel and visualized with ethidium bromide. The DNA was demonstrated to be recombinant without the SmaI site. Subsequent sequence analysis confirmed that the CRP coding sequence had the expected sequence with all of the intended changes incorporated (see section G below); no errors in the sequence were detected. This plasmid was designated pIT10.

G. Selection Of Optimum Expression System

*E. coli* BL21(DE3) cells bearing pIT10 were cultured to assess the effects of the modifications described in section F above on mutant rCRP expression. Cells were grown at 37° C. in a fourteen-liter New Brunswick Model FS614 fermentor in a medium containing NZ amine A$^R$ (enzymatic hydrolysate of casein; Quest International; 20 g/l), (NH$_4$)$_2$SO$_4$ (2 g/l), KH$_2$PO$_4$ (1.6 g/l), Na$_2$HPO$_4$:7H$_2$O (9.9 g/l), sodium citrate (0.65 g/l), MgSO$_4$ (0.24 g/l), glucose (22 g/l) and 100 μg/ml ampicillin. The culture was aerated using compressed air at 50 liters per minute. A sample of the culture was taken just prior to induction and plated on various media to assess plasmid stability (assay for plasmid stability performed as described below). Synthesis of the mutant CRP subunit was induced with 1 mM IPTG (Gold Biotechnology Inc.) when the cell density reached OD$_{600}$=5. Three hours after induction, the fermentation vessel was placed at 4° C. and allowed to chill overnight. The cells were harvested by centrifugation at 12,000×g for 10 minutes at 4° C. in a Beckman JA10 rotor, and the inclusion bodies isolated by the procedure described in section H below.

The inclusion body protein was analyzed by SDS-PAGE and Western blot. To perform the SDS-PAGE, the inclusion body protein was electrophoresed using the standard Pharmacia Phast electrophoresis system and reagents. In particular, commercially prepared SDS-PAGE buffer strips and 20% acrylamide gels (20% Phast gels) were used. Commercially available molecular weight standards were run in parallel wells to assess apparent molecular weights. Gels were stained for protein using Coomassie Brilliant Blue. Gels were subjected to Western blot analysis by transferring electrophoreticahly-separated protein onto nitrocellulose paper and adding monospecific goat anti-neo-CRP antiserum LP4-HRP (prepared as described in section F above). The results of both tests showed that the sequence modifications introduced into the CRP coding region had eliminated any detectable expression of the 7000 Mr fragment. Furthermore, the yield of inclusion body protein increased from roughly 800 mg/10 liters for pIT4 to nearly 8 g/10 liters for pIT10. In contrast with pIT4, significant mutant rCRP expression prior to induction was obtained using pIT10.

Plasmid stability was assessed by a simple plating test described in Studier and Moffat, *J. Mol. Biol.*, 189, 113–120 (1986). Briefly, prior to induction, samples are withdrawn and plated on LB medium, LB medium with ampicillin, LB medium with IPTG, and LB medium with ampicillin and IPTG. Since ampicillin resistance is conferred on *E. coli* BL21(DE3) by the β-lactamase gene on the plasmid, only cells bearing the plasmid will grow on LB with ampicillin. In contrast, cells with the plasmid grow poorly, if at all, on LB medium with IPTG, since rapid transcription of the target gene by T7 RNA polymerase occurs in the presence of IPTG. Cells that have lost the plasmid will grow since there is no promoter for the T7 RNA polymerase. Finally, the LB plate (no ampicillin or IPTG) permits growth of all cells, while the addition of both IPTG and ampicillin should restrict all growth.

When this test was performed on *E. coli* BL21(DE3) containing pIT4, the plasmid was found to be stably maintained as judged by similar colony counts on LB medium and LB medium with ampicillin and by the absence of colonies in the presence of IPTG. However, when *E. coli* BL21(DE3) containing pIT10 was subjected to the same analysis, a considerable number of colonies was found to grow in the presence of IPTG, and a corresponding decrease was observed in the number of colonies on LB medium with ampicillin. A more careful inspection of the plates revealed that the colonies growing on the LB medium with ampicillin had a distinctly different morphology (small and opaque) than those on the LB medium with IPTG (larger, translucent), while the colonies on LB medium without additives exhibited mixed phenotypes. It was concluded that expression of the mutant rCRP was correlated with colonies that appeared small and opaque compared with the larger, translucent colonies formed by cells that had lost the plasmid. When coupled with the observation that the mutant rCRP is expressed at significant levels from pIT10 prior to induction, these results suggest that the mutant rCRP is toxic to the cells. As ampicillin is depleted from the medium by the secreted β-lactamase, cells that have lost the plasmid grow considerably more rapidly than those expressing the recombinant protein. The result is that by the time of induction, only ~50% of the cells are capable of producing the mutant rCRP.

Novagen, Inc. has developed several variants of the BL21(DE3) expression strain and of the pET3a vector used in the work described above. Eight additional expression strains utilizing some of these vectors (pET-9a and pET-24a (+), as well as pET-3a) and *E. coli* strains (BLR(DE3) and BLR(DE3)pLysS, as well as BL21(DE3)) were constructed with the aims of increasing induced expression, decreasing basal transcription, and improving plasmid stability.

Plasmids pET-9a and pET-24a(+) are derivatives of plasmid pET-3a in which the β-lactamase gene has been replaced with the gene conferring resistance to kanamycin. Both plasmids possess the T7 promoter, but pET24a(+) has been further modified by inserting the lac operator sequence between the promoter and the multiple cloning site. This vector is designed to provide a binding site for the lac repressor which will, in the absence of inducer, prevent transcription of the target gene.

*E. coli* strain BLR(DE3) is identical to BL21(DE3), except that it is rec A⁻ and is therefore recombination deficient. Strain BLR(DE3)pLysS is a derivative of BLR (DE3) which carries a plasmid-borne copy of the T7 lysozyme gene. This strain is designed to provide a small quantity of T7 lysozyme to bind and inhibit any T7 RNA polymerase synthesized prior to induction.

Figure 8:
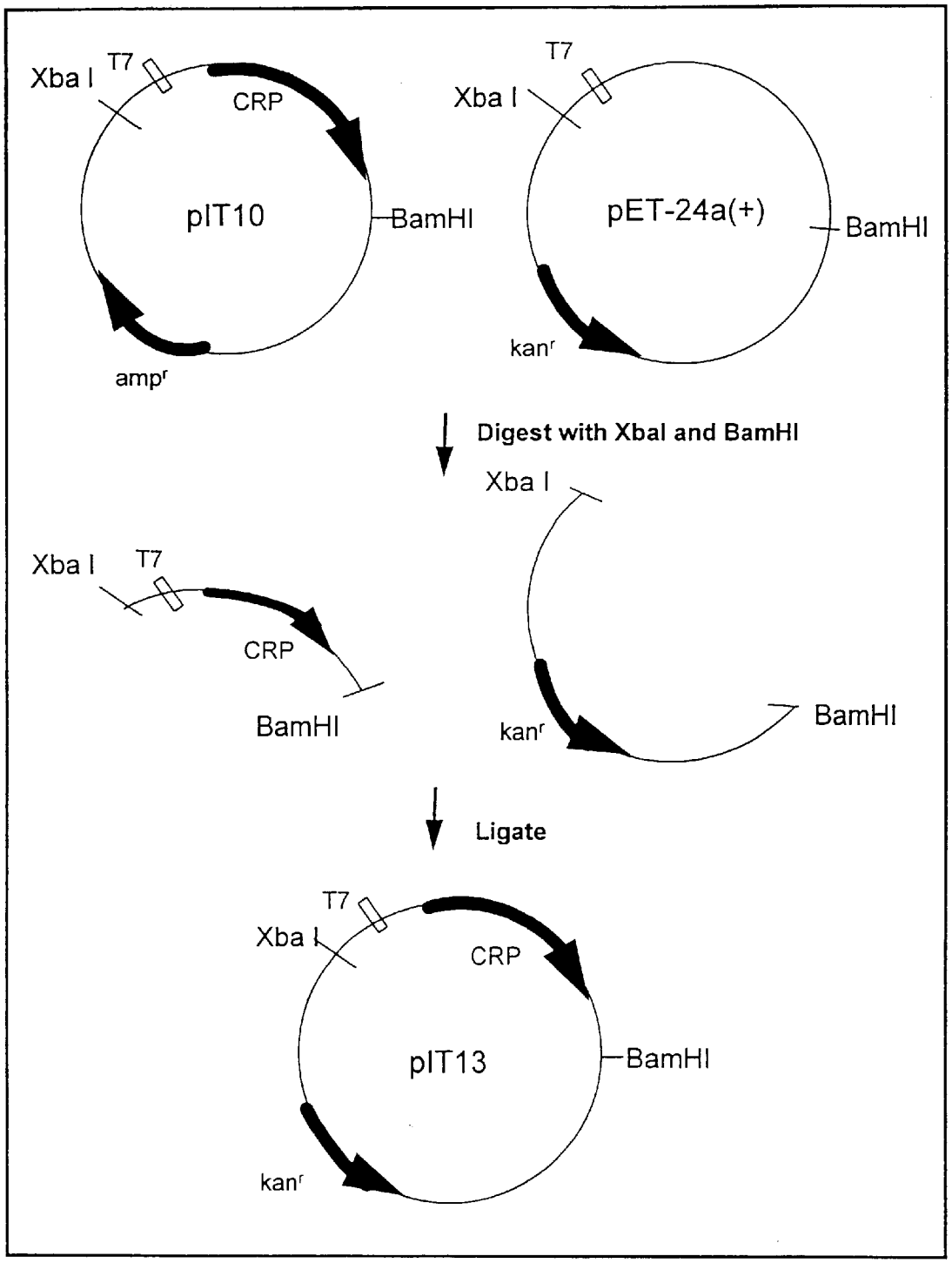
FIG. 8 illustrates the preparation of plasmid pIT13.

Since pET-9a and pET-24a(+) are derivatives of pET-3a, both plasmids have the XbaI and BamHI sites in the same positions as in the pETV vector used in the previous expression systems. The mutant CRP coding sequence was therefore excised from pIT10 and cloned into each vector digested with the same enzymes. The ligation mixtures were transformed into *E. coli* DH5α cells, and transformants were selected by kanamycin resistance. Colonies were screened by restriction analysis of miniprep DNA (procedure described above in section F). Plasmid DNAs from confirmed recombinants were purified on cesium chloride gradients. These plasmids were designated pIT12 (derived from pET-9a) and pIT13 (derived from pET-24a(+))., The preparation of pIT13 is shown in FIG. 8.

Expression plasmids pIT10, pIT12 and pIT13 were independently transformed into *E. coli* BL21(DE3), BLR(DE3) or BLR(DE3)pLysS. Transformants were selected by resistance to appropriate antibiotics (see Table 6 below), and the colonies screened by restriction analysis of miniprep DNA (procedure described above in section F). Confirmed recombinants were expanded in liquid culture in LB medium with the following antibiotics:

TABLE 6

| Plasmid/*E. coli* | Antibiotics |
| --- | --- |
| pIT4/BL21(DE3) | ampicillin (100 μg/ml) |
| pIT10/BL21(DE3) | ampicillin (100 μg/ml) |
| pIT10/BLR(DE3) | ampicillin (100 μg/ml) |
| pIT10/BLR(DE3)pLysS | ampicillin (100 μg/ml) + chloramphenicol (34 μg/ml) |
| pIT12/BL21(DE3) | kanamycin (50 μg/ml) |
| pIT12/BLR(DE3) | kanamycin (50 μg/ml) |
| pIT12/BLR(DE3)pLysS | kanamycin (50 μg/ml) + chloramphenicol (34 μg/ml) |
| pIT13/BL21(DE3) | kanamycin (50 μg/ml) |
| pIT13/BLR(DE3) | kanamycin (50 μg/ml) |
| pIT13/BLR(DE3)pLysS | kanamycin (50 μg/ml) + chloramphenicol (34 μg/ml) |

To expand the recombinants, 0.5 ml of an overnight culture of each strain was used to inoculate 50 ml of the appropriate medium in a 250 ml flask. The cultures were incubated at 35° C. with shaking until the $A_{600}$ reached 0.8–1.0. Then, 10 ml of each culture were removed and the cells harvested by centrifugation for 5 minutes at 8000 rpm in a Sorvall SM24 rotor. An additional sample of each culture was removed for plasmid stability testing. Mutant rCRP synthesis was then induced by the addition of IPTG to the remaining 40 ml culture to a final concentration of 0.4 mM. After a three-hour induction period, 10 ml of each culture was harvested by centrifugation as just described.

Plasmid stability was determined as described above using the appropriate antibiotics (see Table 6). The greatest plasmid loss was observed in *E. coli* BL21(DE3) bearing PIT10 which confers ampicillin resistance (~10%). With plasmids pIT12 and pIT13, which confer kanamycin resistance, the extent of plasmid loss in *E. coli* BL21(DE3) was <1%. In the rec A⁻ strains BLR(DE3) and BLR(PE3) pLysS, no plasmid loss was detected with either pIT12 or pIT13. With pIT10 in *E. coli* BLR(DE3), about 3% of cells had lost plasmid, whereas this plasmid appeared stable in *E. coli* BLR(DE3)pLysS. Plasmid stability is set forth in Table 7 below.

TABLE 7

| Plasmid/*E. coli* | Plasmid Stability |
| --- | --- |
| pIT4/BL21(DE3) | Stable |
| pIT10/BL21(DE3) | about 10% loss |
| pIT10/BLR(DE3) | about 3% loss |
| pIT10/BLR(DE3)pLysS | no loss |
| pIT12/BL21(DE3) | <1% loss |
| pIT12/BLR(DE3) | no loss |
| pIT12/BLR(DE3)pLysS | no loss |
| pIT13/BL21(DE3) | <1% loss |
| pIT13/BLR(DE3) | no loss |
| pIT13/BLR(DE3)pLysS | no loss |

To assess the level of mutant rCRP synthesis in the cell strains prior to induction, a sample of a lysate of each culture was subjected to SDS-PAGE electrophoresis on a 20% Phast gel and subsequent Western blotting (procedure described above, this section) using mAb 3H12. The lysates were prepared by suspending the cell pellets (obtained by centrifuging the 10 ml samples of each culture as described above) in 1 ml of 50 mM Tris-Cl, pH 8.0, 2 mM EDTA. To 500 μl of this suspension were added 100 μg/ml DNase, 50 μl Triton X-100 and 100 μg/ml lysozyme. After vortexing, the suspension were incubated for 15 minutes at 37° C. Lysates which remained viscous were passed through a 23 guage needle attached to a syringe. This experiment showed that in both *E. coli* BL21(DE3) and BLR(DE3), a fairly high level of uninduced expression occurred whether ampicillin (pIT10) or kanamycin (pIT12) was used for selection. In contrast, little or no expression was detected using the T7-lac promoter (kanamycin-resistant plasmid pIT13) in either strain. In *E. coli* BLR(DE3)pLysS, uninduced expression could be detected only with the ampicillin-resistant plasmid pIT10.

A sample of a lysate from each induced culture was also subjected to SDS-PAGE electrophoresis on a 20% Phast gel, and the proteins were visualized by staining with Coomassie Brilliant Blue (procedure described above, this section). As expected, significantly higher levels of expression were observed in all strains when compared with *E. coli* BL21 (DE3) bearing the pIT4 plasmid. The expression levels observed in the strains appeared to be similar, suggesting that the modifications made to lower the basal expression were having little effect on the induced levels of the protein. It did appear that in strain BLR(DE3), pIT13 gave higher expression than did pIT10 or pIT12, while in strain BLR (DE3)pLysS, pIT10 gave a little better expression.

Given the levels of mutant rCRP production in uninduced cultures and the potential benefit of using a rec A⁻ strain, the use of pIT12 and pIT13 in the BLR(DE3) BLR(DE3)pLysS strains looked promising. The relative amounts of induced protein in the lysates were, there-fore, compared again using Western blotting (performed as described above, this section, after SDS-PAGE electrophoresis on 20% Phast gels) using mAb 3H12. As with SDS-PAGE, the Western blot results showed that there was little detectable difference among these strains in their abilities to express significant amounts of mutant rCRP.

As a final analysis, the growth rates of the various strains on LB medium plus antibiotic were compared. Most of the rec A⁻ strains were found to grow somewhat more slowly than their recombination-competent counterparts. Furthermore, those strains which exhibited significant levels of expression prior to induction grew more slowly than those which did not.

As noted above, BLR(DE3)pLysS strains bear a plasmid encoding T7 lysozyme. In addition to its ability to bind to and inhibit the activity of T7 RNA polymerase, this protein digests the bacterial cell wall. Cells expressing this protein are somewhat more fragile than those that do not, and will lyse after freezing and thawing. While this has some advantages, our protocol for storing and resuspending the harvested cell paste on a large scale (see next section) would be complicated by this. Furthermore, the BLR(DE3)pLysS expression strains have two separate plasmids. In addition to the requirement for two antibiotics to maintain selection for both plasmids, the analysis of plasmids isolated from these strains is complicated by the fact that a mixture is always present.

On the basis of all of the above data, the expression system chosen was plasmid pIT13 in *E. coli* BLR(DE3). The combination of the kanamycin resistance marker and the T7-lac operator promoter help to ensure that the plasmid will remain under selection and that very little, if any, expression will occur prior to induction. The rec A⁻ genotype of the strain limits the possibility of recombination. Finally, the characteristics of the strain permit ease of handling on a production scale. Culturing the pIT13/BLR(DE3) strain under the same conditions as the pIT10/BL21(DE3) strain (except for the type of antibiotic) resulted in the production of 12.5 g of inclusion body protein for the pIT13/BLR(DE3) strain as compared to 8.0 g for the pIT10/BL21(DE3) strain.

Plasmid pIT13 was isolated from the *E. coli* BLR(DE3) expression strain and purified on a cesium chloride gradient. The CRP coding region was sequenced in the expression vector by the dideoxy chain terminator method of Sanger et al., *Proc. Nat'l. Acad. Sci. USA*. 74, 5463–5467 (1977) using Sequence version 2.0 (U.S. Biochemical Corp.) and $^{33}$P-dATP as the radiolabel.

Figure 9:
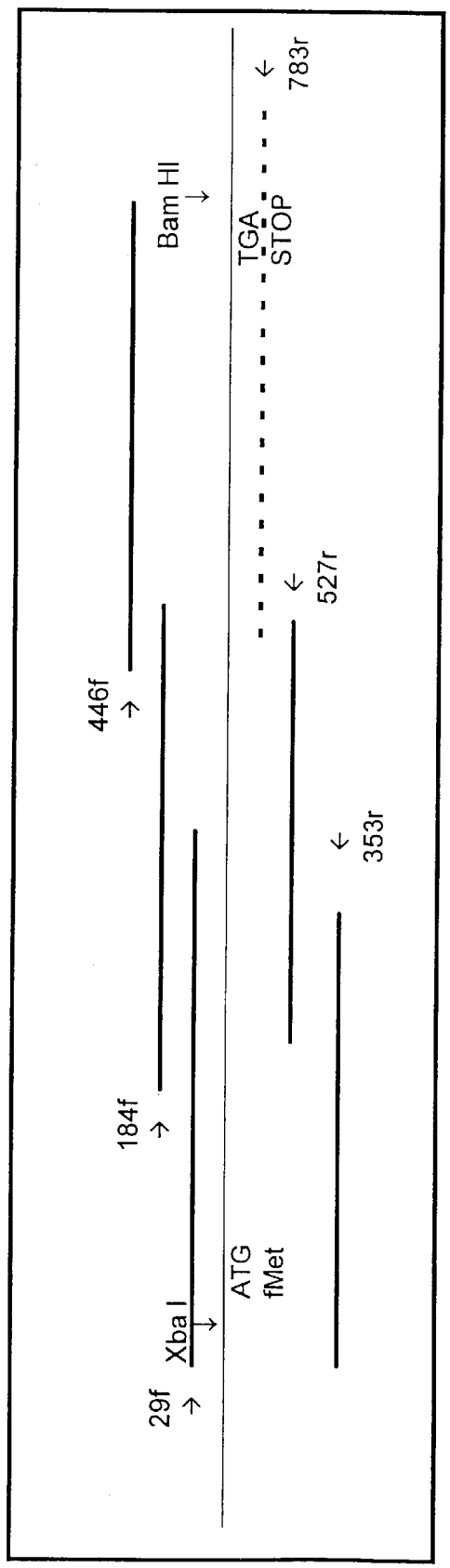
FIG. 9 illustrates the strategy for DNA sequencing of the mutant CRP coding region of pIT13.

FIG. 9 illustrates the sequencing strategy. In FIG. 9, the plasmid is represented by the long narrow line in the center. The start and stop codons and the restriction sites used for cloning into pET24a(+) are marked. The primers are represented by small arrows, and the region of the sequence read from each primer is shown in bold. Three forward (29f, 184f 446f) and three reverse (353r, 527r, 783r) primers were used to cover the entire coding region. The dashed line is the region designed to be read by the 783r primer (see below).

Reaction products were separated on a 5% Hydrolink Long Ranger gel (AT Biochem Corp.). A sample of each reaction mixture was loaded and electrophoresed until the bromphenol blue dye marker reached the bottom of the gel (1st load). Identical samples were then applied to the remaining wells (2nd load) and electrophoresis continued until the bromphenol blue dye marker contained in the second set of samples reached the bottom of the gel. The gel was then dried and contacted with X-ray film for 2, 6.5, or 17 hours, and the sequence was read from the developed film.

The sequence determined by this procedure corresponded exactly to the coding sequence reported by Woo et al., *J. Biol. Chem.*, 260, 13384–88 (1985) with the following differences: the synonymous substitution in the wobble position of codon 152 (see section F above); the deletion of the leader sequence and introduction of an ATG codon for translation initiation; the substitution of a T for the G in the wobble position of codon 48; the substitution of a C for the T in the wobble position of codon 50; the substitution of a CGC codon (alanine) for the TGC codon for cysteine 36; and the substitution of a CGC codon (alanine) for the TGT codon for cysteine 97. It was, therefore, concluded that the predicted amino acid sequence of the mutant rCRP is identical to the sequence reported for unmutated CRP, except for the three changes purposefully factored into the molecule: 1) the N-terminal PCA amino acid of unmutated CRP is preceded by a formylated-methionine and is itself changed to glutamine; 2) cysteine residue number 36 is substituted with an alanine residue; and 3) cysteine residue number 97 is substituted with an alanine residue.

The DNA sequence results demonstrate that the genetic manipulations performed on the CRP coding sequence of pIT4 to correct the sequence and to obtain better expression of the mutant rCRP were performed correctly. No base additions, deletions, or substitutions were unintentionally introduced into the sequence.

H. Purification Of Mutant CRP Subunits

The bacterial fermentations and the preparation of inclusion bodies were peformed by Bio-Technical Resources (Manitowoc, Wis.) under aseptic conditions following the Good Laboratory Practices (GLP) guidelines of the Food and Drug Administration. Briefly, *E. coli* BLR(DE3) bearing the pIT13 plasmid was cultured in a 250 liter pilot fermentor (New Brunswick Scientific) using the conditions described in the first paragraph of section G above, except that the culture medium contained 50 µg/ml kanamycin instead of the ampicillin. After the three-hour induction period, the cells were harvested by continuous flow centrifugation at 15,000 rpm in a Sharples model AS16VB tubular bowl centrifuge. The harvested cell paste was transferred into sterile plastic bags and frozen at −80° C.

The cell paste was thawed by placing the sealed plastic bags in a 45° C. water bath. The thawed cell paste was then suspended in cold breakage buffer (20 mM Tris-HCl, pH 7.6, 5 mM EDTA, 1 mM phenylmethyl sulfonyl fluoride (PMSF; Sigma Chemical Co.) at a ratio of 200 ml buffer per gram cell paste and processed in a sterile blender at low speed for 30–45 seconds. The homogeneous suspension was passed twice through a Nyro Soave homogenizer (equipped with a cell disruption valve) at a pressure of 500 bar. As it exited the homogenizer, the suspension was passed through a sterile cooling coil packed in an ice bath for cooling. It was then collected in a sterile covered container on ice.

This lysate was centrifuged at 12,000×g in a Beckman model J2–21 centrifuge for 10 minutes at 4° C. The pellet was resuspended in breakage buffer at 100 ml buffer per gram of initial cell paste. The suspension was then passed twice through the homogenizer, this time at 700 bar. The extract was centrifuged at 12,000×g for 25 minutes at 4° C. in a Beckman model J2-21 centrifuge to collect the inclusion body pellet.

The inclusion bodies were washed once with breakage buffer at a ratio of 150–200 ml buffer per 100 grams of initial cell paste by suspending the pellet in the buffer with a sterile glass rod and then centrifuging as described above. They were then washed three times with wash buffer (breakage buffer containing 0.5% Triton X-100 (Sigma Chemical Co.) at a ratio of 100–150 ml per 100 grams initial cell paste. The pellets were finally suspended in approximately 75 ml of breakage buffer per 100 grams of initial cell paste, aliquoted into sterile tubes, and frozen at −80° C. until further processing.

Figure 10B:
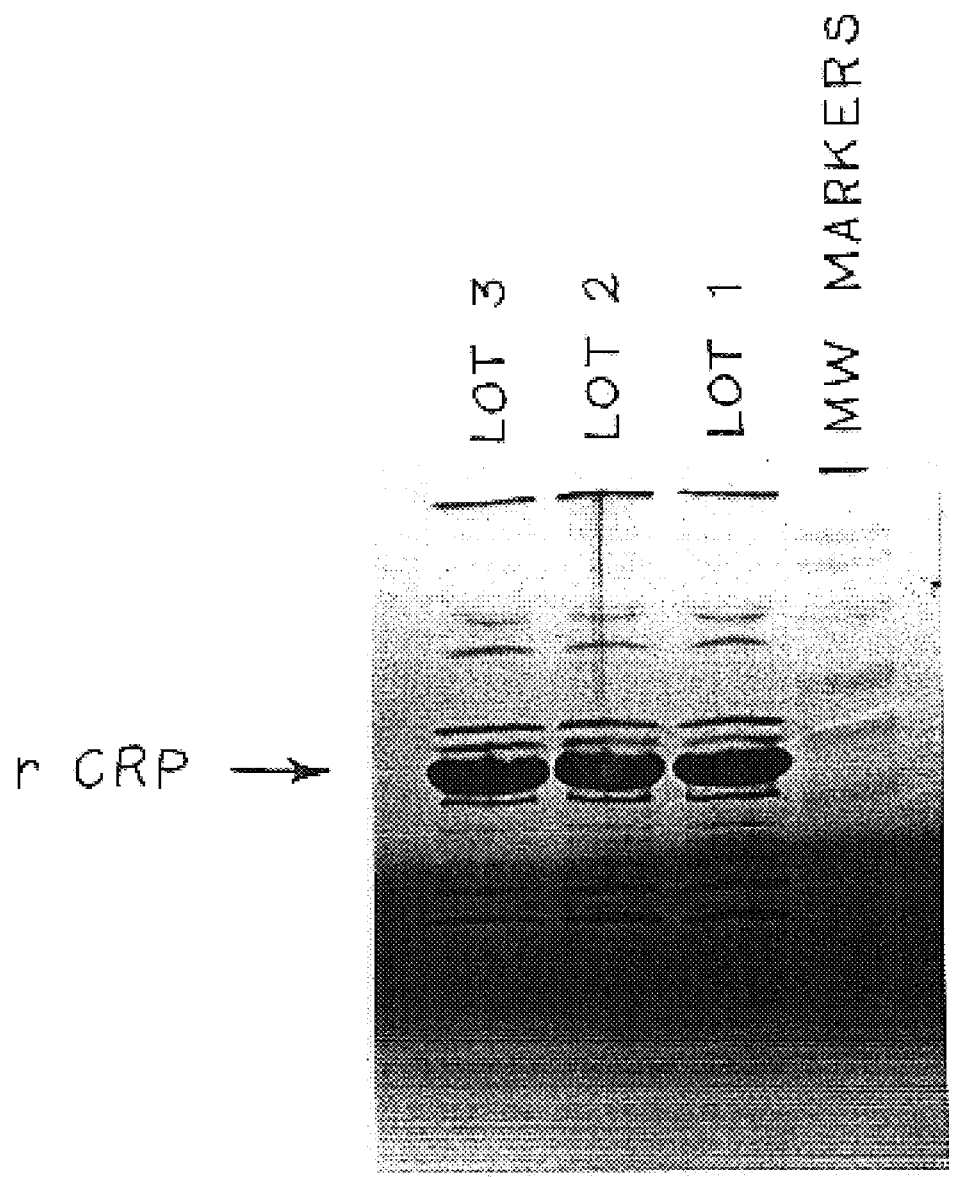
FIG. 10B is a Western blot obtained by using monospecific goat anti-neo-CRP antiserum LP3-HRP to stain the SDS-PAGE electrophoretic patterns of three lots of inclusion body preparations isolated from *E. coli* BLR(DE3) bearing plasmid pIT13.

Representative SDS-PAGE and Western blot analyses of three lots of inclusion bodies are shown in FIGS. 10A and 10B. To perform the SDS-PAGE, samples were diluted to approximately 1 mg/ml and boiled in SDS and β-mercaptoethanol, and 41 µl of each treated sample were loaded onto a homogenous 20% Phast gel. The gel was either stained with Coomassie Brilliant Blue (FIG. 10A) or the proteins were transferred to nitrocellulose and probed with monospecific goat anti-neo CRP antiserum LP4-HRP (FIG. 10B).

The concentration of protein in the inclusion body suspension was estimated using the Bicinchoninic acid protein assay (Pierce Chemical Co.) or by solubilizing the protein in 6M GuHCl and measuring the $A_{280}$ (using the extinction coefficient for pure mCRP; $1.95[mg/ml]^{-1}$)). The inclusion bodies were then pelleted by centrifuging for 10 minutes at 12,000 rpm in a Sorvall GSA rotor. The supernatant was discarded, and the pellet was dissolved in a solution of 6M GuHCl in 25 mM Tris, pH 8 (6M GuHCl/Tris), to a concentration of between 5–10 mg protein/ml. The concentration of solubilized protein was determined by measuring the $A_{280}$ of a diluted sample. The inclusion body preparation was then diluted to a final concentration of 5 mg protein per ml with the 6M GuHCl/Tris buffer.

Once the protein had been solubilized and diluted as just described, an initial ammonium sulfate fractionation step was performed. Using a peristaltic pump, a saturated solution of ammonium sulfate was added dropwise with stirring to a final concentration of 25% saturation at 0° C. The resulting suspension was stirred on ice for another 30 min following the completion of the ammonium sulfate addition, after which it was centrifuged 10 min at 12,000 rpm in a Sorvall GSA rotor. The supernatant, which contains primarily impurities, was discarded. The pellets were washed with sterile saline in a volume equivalent to that of the original solubilized protein solution to remove residual ammonium sulfate. Pellets were stored at 4° C. until further processing.

A Q-Sepharose Fast Flow$^R$ anion exchange column was equilibrated with 25 mM Tris-Cl, pH 8. The washed ammonium sulfate precipitate containing the mutant rCRP was solubilized at a concentration of 0.5 mg/ml by adding 10 mM Tris base and stirring until a suspension was formed. NaOH was then added until the solution became clear (pH 12.2–12.5). The pH was then titrated to 9.0 with HCl. The solubilized protein was loaded onto the Q-Sepharose Fast Flow$^R$ column at a linear flow rate of 30 cm/hour, with the total protein load not exceeding 5 mg/ml of resin. The column was washed with 1 volume of the equilibration buffer (25 mM Tris-Cl, pH 8), and then developed with a two-column volume linear gradient of 0–1 M NaCl in 25 mM Tris-Cl, pH 8. After the NaCl concentration was rapidly returned to 0, the column was washed with an additional column volume of the equilibration buffer. The mutant rCRP was finally eluted from the column with 8M GuHCl in 25 mM Tris, pH 8. $A_{280}$ was measured using the BioPilot$^R$ system. A representative elution profile generated by the Biopilot$^R$ system is shown in FIG. 11.

The mutant rCRP adsorbs very strongly to the Q-Sepharose Fast Flow$^R$ column in the absence of a denaturant and will not elute with the NaCl gradient or with a pH gradient up to at least pH 12, allowing for an excellent separation of the mutant rCRP from endotoxin. The mutant rCRP readily elutes from the column in the presence of a denaturant, such as GuHCl. However, urea should not be used for this elution step.

The eluate from the Q-Sepharose Fast Flow$^R$ column was concentrated by precipitation with 25% saturated ammonium sulfate as described above. After the pellet was washed with saline, it was dissolved in 3% (w/v) sodium dodecyl sulfate (SDS), 25 mM Tris-Cl, pH 9.0 at a concentration of 5–10 mg protein/ml (estimated using absorbance at 280 nm and extinction coefficient for pure mCRP). It was then applied to a 5 cm×92 cm Superdex 200 gel filtration column previously equilibrated in 1% SDS, 25 mM Tris-Cl, pH 8.0. The sample size was 1–1.5% of the column volume, and the linear flow rate was 30 cm/hr. The mutant rCRP typically eluted at a volume of 1120 ml (60% of the total bed volume), and collection began when the peak reached 25–30% of its expected height and was terminated when it returned to the same level. $A_{280}$ was measured on the Biopilot$^R$ system. FIG. 12 illustrates a representative chromatogram for this column.

The mutant rCRP collected from the Superdex 200 column were first chilled to 0–4° C. Any precipitated SDS was then removed by a 5–10 min centrifugation at 12,000 rpm in a Sorvall GSA rotor. Then 5µl of a 25% (w/v) solution of KCl per ml of supernatant was added, and the insoluble potassium dodecyl sulfate was removed by centrifugation at 12,000 rpm in a Sorvall GSA rotor. The KCl addition and centrifugation were repeated twice more. Finally, the supernatant was brought to 30% saturated ammonium sulfate and the resulting precipitate was collected by centrifugation at 12,000 rpm in a Sorvall GSA rotor. The pellet was dissolved at 3–4 mg protein/ml (estimated as described above) in 10 mM Tris-Cl, pH 9.2.

The solubilized mutant rCRP was next applied to a Sephadex G-25 (fine) column (Pharmacia) equilibrated in 10 mM Tris-Cl, pH 7.4, at a linear flow rate of 70 cm/hr with the sample volume not to exceed 20% of the column volume. $A_{280}$ and conductivity were measured on the Biopilot$^R$ system, and the mutant rCRP was usually present at a concentration of 1.5–2 mg/ml. A typical chromatogram for this column is shown in FIG. 13.

Figure 14:
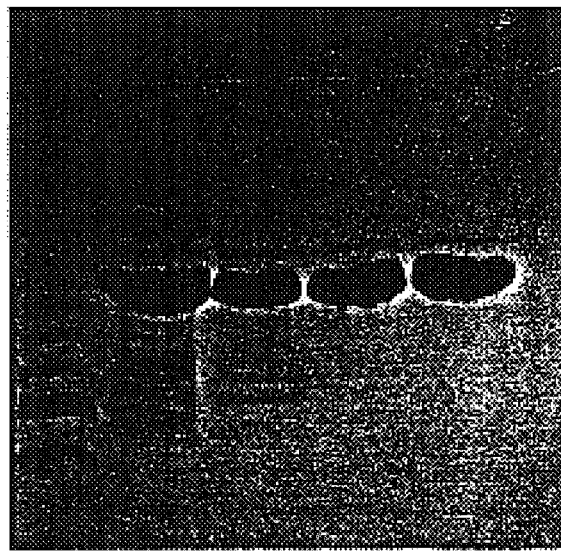
FIG. 14 presents representative SDS-PAGE results for the complete purification scheme for isolating a mutant protein according to the invention from *E. coli* BLR(DE3) bearing plasmid pIT13.

FIG. 14 presents the SDS-PAGE results for the complete purification scheme and illustrates the increase in purity attained in each step. The final mutant rCRP preparation is nearly homogenous. To perform the SDS-PAGE, samples were boiled in 2.5% SDS and 5% (v/v) β-mercaptoethanol, and 8 μg of each sample was loaded onto a 20% homogeneous Phast gel. Proteins were visualized by staining with Coomassie Brilliant Blue.

The concentration of residual SDS in the mutant rCRP preparation was measured using the acridine orange binding assay described in Anal. Biochem., 118, 138–141 (1981). Following the purification protocol described above, the concentration of residual SDS in the mutant rCRP preparation is routinely below the limit of detection (~0.001% w/v) of the, assay.

Finally, the purified mutant rCRP was sterile filtered through 0.2μ filters. The filtered, sterile mutant rCRP was then bottled in pyrogen-free sterile vials for injection.

I. Characterization Of The Mutant rCRP

1. SDS-PAGE and Western Blot

Purified mutant rCRP produced by the method described in section H was compared with mCRP in SDS-PAGE and Western blot analyses using 20% Phast gels as described in section G above. The mCRP was prepared from purified native CRP as described in section C above.

Figure 15A:
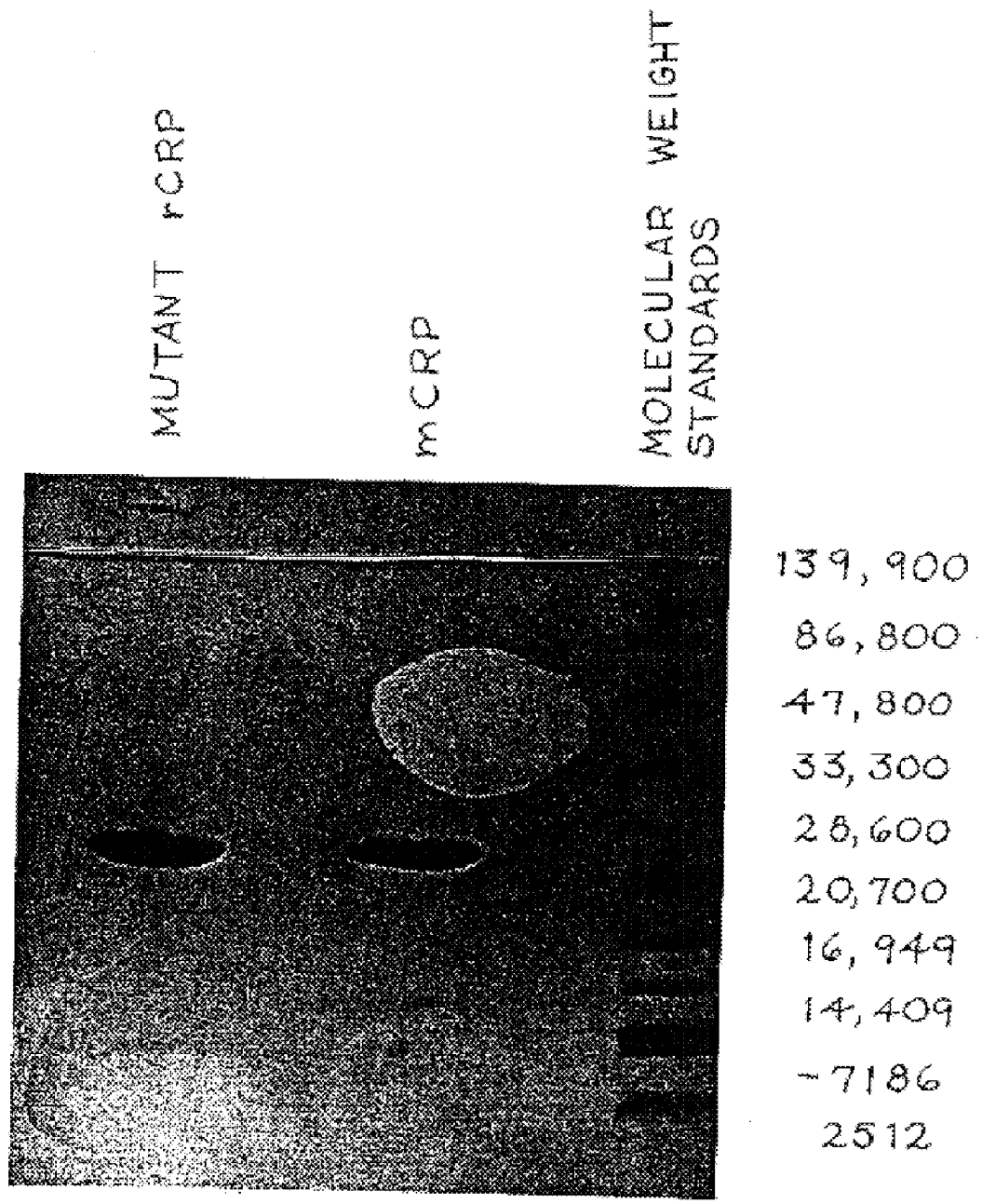
FIG. 15A is an SDS-PAGE gel obtained by electrophoresing mCRP and a mutant protein according to the invention purified from *E. coli* BLR(DE3) bearing plasmid pIT13.
Figure 15B:
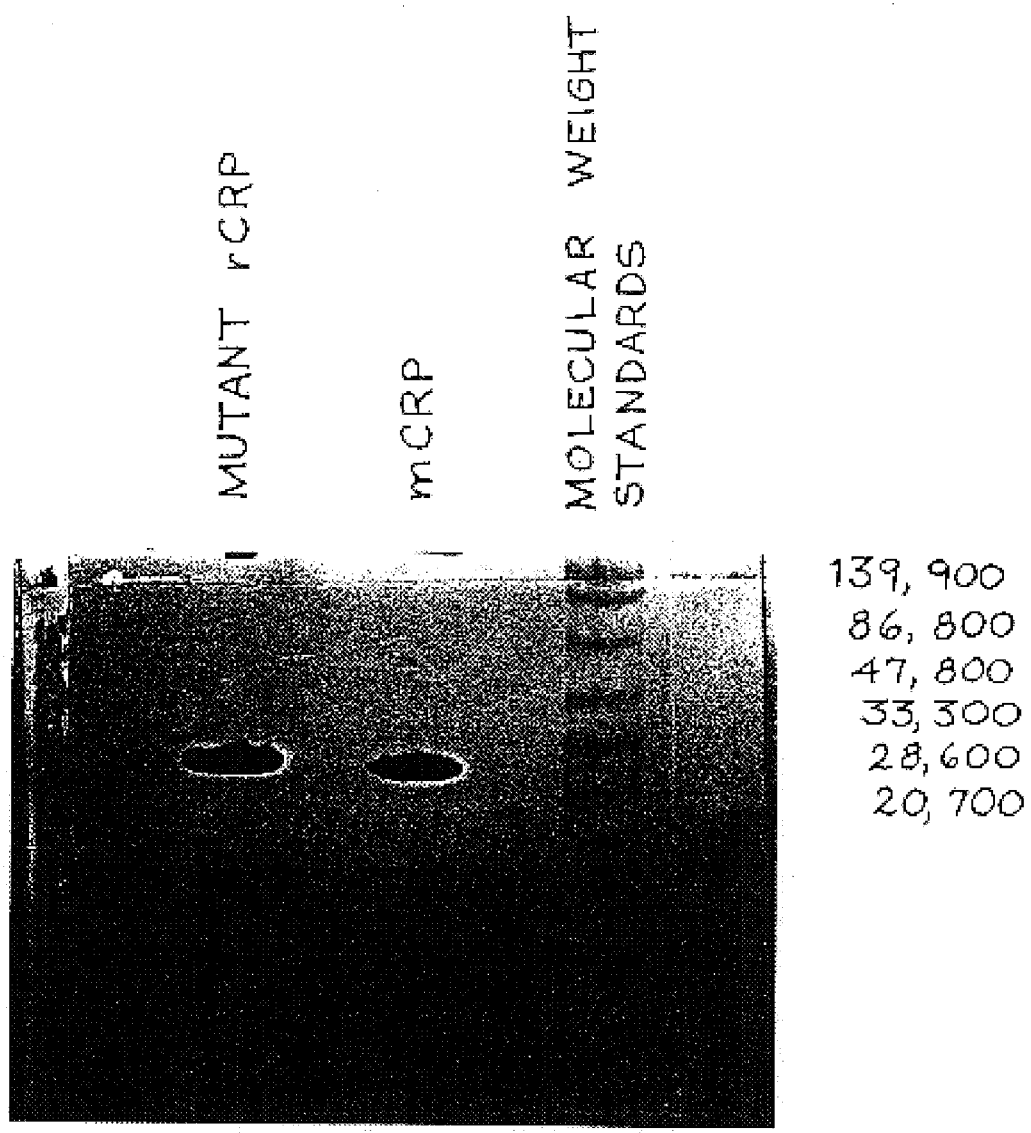
FIG. 15B is the Western blot obtained by using anti-neo-CRP monoclonal antibody 3H12 to stain the SDS-PAGE electrophoretic patterns of mCRP and a mutant protein according to the invention purified from *E. coli* BLR(DE3) bearing plasmid pIT13.

The results are shown in FIGS. 15A and 15B. In particular, the mutant rCRP and mCRP migrated as single bands on SDS-PAGE; no extraneous Coomassie-staining bands were noted in either sample suggesting that both the mCRP and the mutant rCRP are pure to the level of sensitivity of this analytical procedure. Each protein migrated with identical apparent molecular weights of Mr 23,000. This agrees with the literature values for the molecular weight of the unmutated CRP subunit in SDS-PAGE and with the molecular weights calculated from the known primary sequences of the unmutated CRP subunit (Mr 22,976) and mutant rCRP (Mr 23,114). These data show that the mutant rCRP has a molecular weight and purity essentially identical to mCRP.

Western blot analysis using mCRP-specific monoclonal antibody 3H12 demonstrates that the protein bands of both the mutant rCRP and of mCRP strongly reacted with this antibody (see FIG. 15B). No additional bands appeared in the transblotted lanes of either isolated protein, indicating an even greater level of purity than indicated by the SDS-PAGE results, since the Western blot results are more sensitive than the Coomassie staining technique. Monoclonal antibody 3H12 is known to react with the carboxy-terminal octapeptide of mCRP. These data show that the mutant rCRP expresses a very similar (probably identical) epitope as that of mCRP.

2. ELISA Analyses

An ELISA assay was performed to determine if monoclonal antibodies specific for different epitopes on mCRP would react with the mutant rCRP produced by pIT13 and purified as described in section H. The ELISA assay was performed as described in section D above using the following three monoclonal antibodies: 3H12, 8C10 and 7A8. The preparation and properties of mAb 3H12 and 8C10 are described above in section D. The preparation and properties of mAb 7A8 are described in U.S. Pat. No. 5,272,257, PCT application WO 91/00872, Ying et al., J. Immunol., 143, 221–228 (1989) and Ying et al., Mol. Immunol., 29, 677–687 (1992). Monoclonal antibody 3H12 reacts with the terminal octapeptide of mCRP, as noted above. Monoclonal antibody 8C10 reacts with an epitope near the amino end of the mCRP sequence; this epitope is presumed to involve residues 22–45, which includes cysteine 36 which is mutated in the mutant rCRP. See Ying et al., Mol Immunol., 29, 677–687 (1992). Monoclonal antibody 7A8 reacts with a third region of mCRP presumed to involve residues 130–138. See Ying et al., Mol Immunol., 29, 677–687 (1992).

The ELISA results are shown in FIG. 16A–C. All three monoclonal antibodies reacted equivalently with mCRP and the mutant rCRP produced by pIT13, including mAb 8C10 which reacts with an epitope believed to include cysteine 36. Each binding curve had a similar shape and relative intensity, suggesting that the mutant rCRP and mCRP both are comprised of, and express, these three distinct epitopes.

3. Biological Activity

Figure 17A:
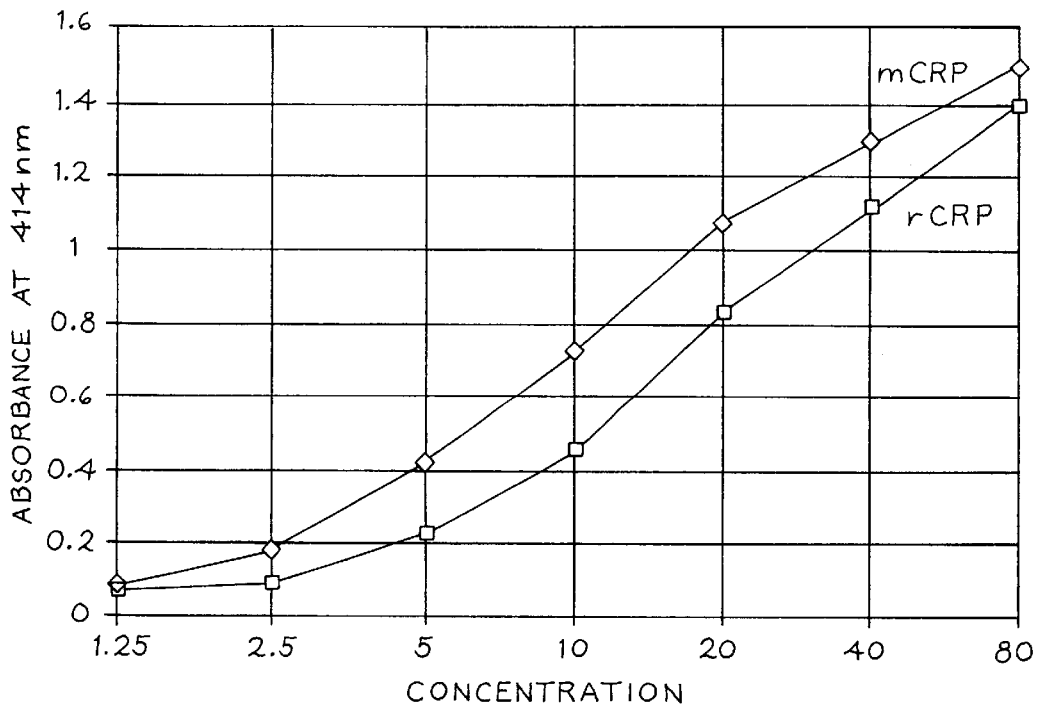
FIG. 17A is a graph of the results of an ELISA assay performed to detect binding of mCRP and a mutant protein according to the invention purified from *E. coli* BLR(DE3) bearing plasmid pIT13 to aggregated IgG.

Modified-CRP has been characterized as a protein which selectively binds immune complexes and aggregated immunoglobulin. The ability of the mutant rCRP produced by pIT13 and purified as described in section H above to bind aggregated immunoglobulin was evaluated and compared with the binding of aggregated immunoglobulin by mCRP. This evaluation was made using the ELISA assay described in section E above, except that only 0.2 μg of each test protein was immobilized per well. The results are presented in FIG. 17A which shows that both mutant rCRP and mCRP bound aggregated IgG. Binding levels for the two proteins were approxima-tely equivalent.

Figure 17B:
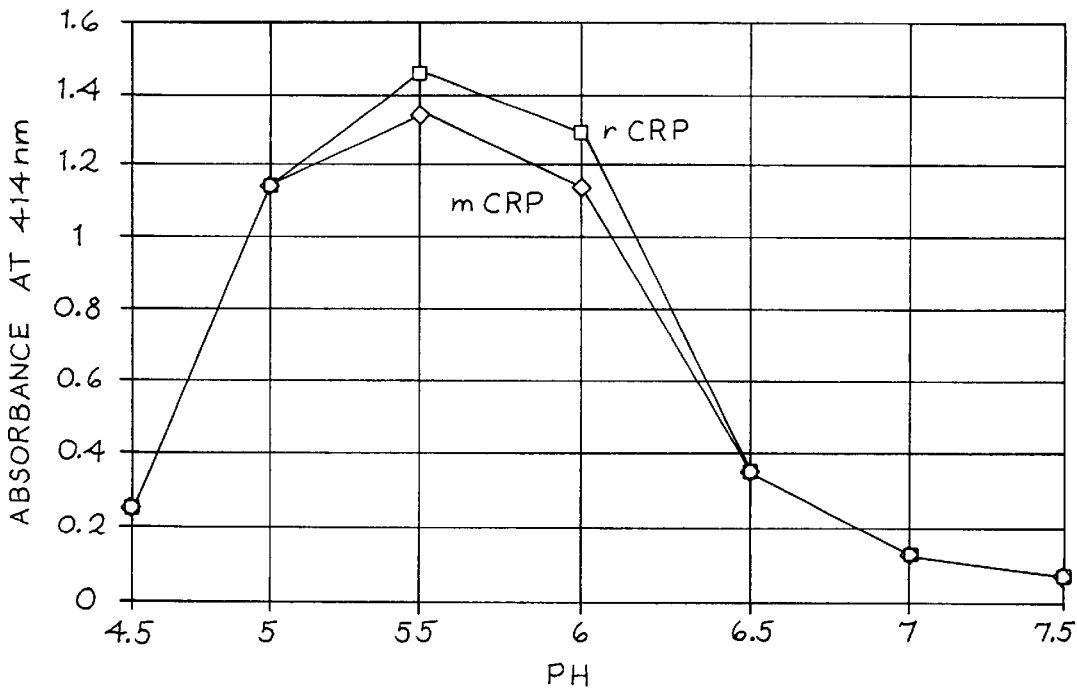
FIG. 17B is a graph of the results of an ELISA assay performed to detect binding of mCRP and a mutant protein according to the invention purified from *E. coli* BLR(DE3) bearing plasmid pIT13 to immune complexes.

Next, defined complexes of peroxidase-anti-peroxidase (PAP) containing three molecules of peroxidase antigen and two molecules of rabbit anti-peroxidase anti-bodies (purchased from Organon Teknika Corp.) were diluted approximately 1:1000 in assay buffer (20 mM sodium citrate/phosphate containing 1% bovine serum albumin) adjusted to various pH values from 4.5 to 7.5 with NaOH. The pH-adjusted PAP reagent (100 μl) was used in the ELISA assay described in section E in place of the aggregated immunoglobulin. After appropriate washings with TBS plus 0.05% Tween 20, bound immune complexes at each pH were detected using ABTS as substrate as described in section E above. The results are presented in FIG. 17B which shows that both mutant rCRP and mCRP bound PAP complexes with a pH maximum between 5.0 and 6.0. Negligible binding was observed at pH 7.0 or 7.5 for both proteins. Approximately equivalent levels of binding were obtained, indicating that the mutant rCRP, like mCRP, is able to bind immune complexes.

J. Amino Acid Seguence Of Mutant rCRP Produced BV pIT4

Experiments were conducted to determine the amino acid sequence of the full-length mutant rCRP subunit produced by pIT4. Since this full-length product is believed to be produced by a ribosomal frameshift during translation of the mRNA, its amino acid sequence cannot be determined from the DNA sequence of pIT4 (see section F above).

First, mCRP and the full-length mutant rCRP subunits produced by pIT4 and pIT13 were digested with 2-(2'-nitrophenylsulfenyl)-3-methyl-3'-bromoindolenine (BNPS-Skatole; Pierce Biochemicals) which cleaves on the C-terminal side of tryptophan residues mCRP was prepared as described in section C above. The full-length products of pIT4 and pIT13 were produced by culturing E. coli BL21 (DE3) and BLR(DE3), respectively, and purifying the full-length products from the cultures, all as described above in sections G and H. The mCRP and the final purified pIT4 and pIT13 products were solubilized at a concentration of 50 mg/ml in 25 mM Tris-Cl, pH 8, containing 6M GuHCl. The reactions were initiated by the addition of four volumes of glacial acetic acid containing 25 mg/ml BNPS-Skatole. Thus, the final reaction conditions were 10 mg/ml protein, 1.2 M GuHCl, 80% acetic acid and 20 mg/ml BNPS-Skatole. After a 24-hour digest at room temperature in the dark, 42.5 μl of each sample were transferred to an Eppendorf tube, and an equal volume of saturated ammonium sulfate was added to each tube. After a two-minute centrifugation in an eppendorf microcentrifuge, the supernatants were discarded, and the pellets were washed with 200μl of 0.1 M Tris-Cl, pH 7.4. The pellets were finally suspended in 42.5μl of 8 M urea in 25 mM Tris-Cl, pH 8.5. The samples were then analyzed by SDS-PAGE performed as described in section G above.

Figure 18A:
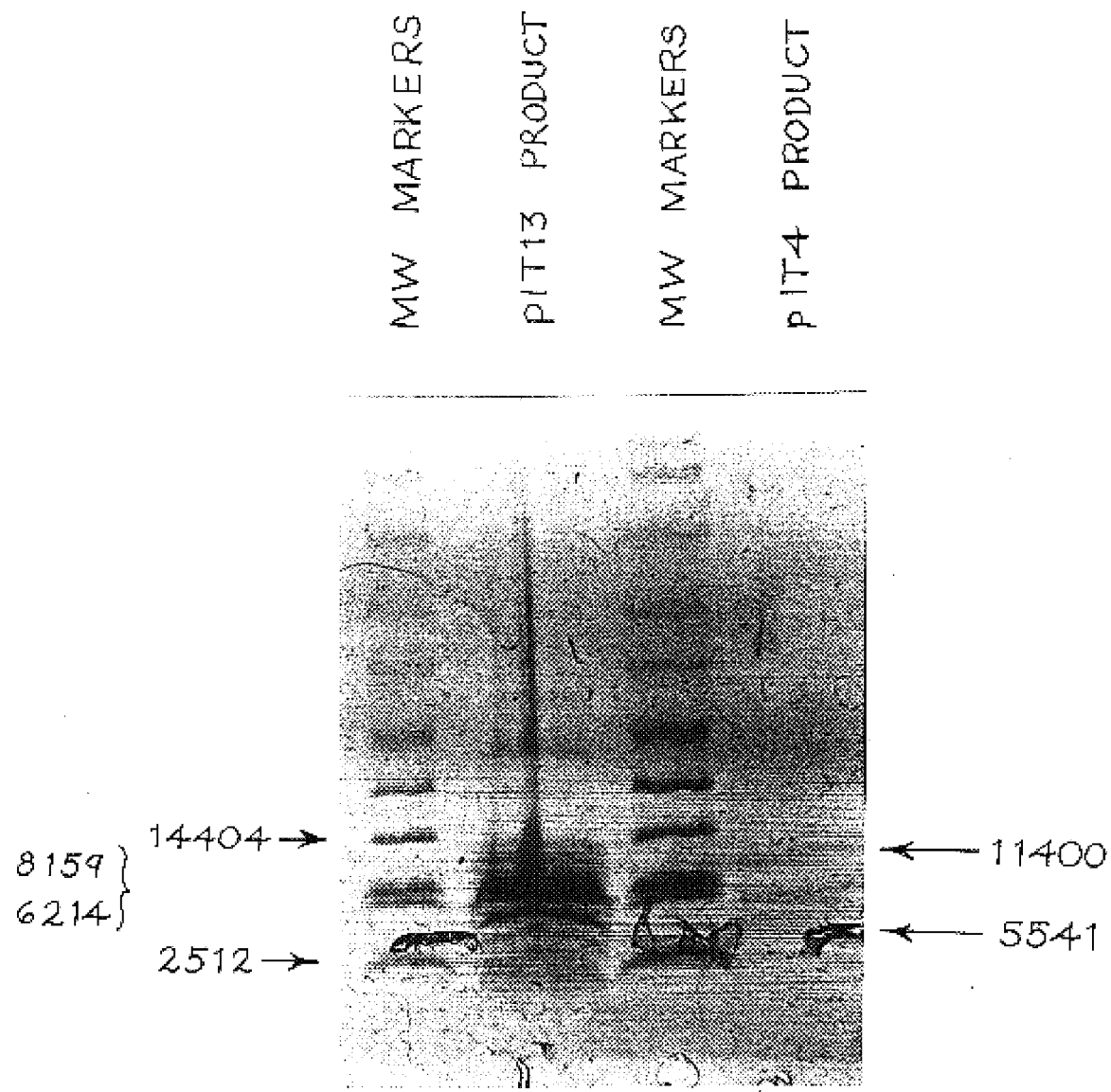
FIG. 18A is an SDS-PAGE gel obtained by electrophoresing the digests produced by treating mCRP and the mutant proteins produced by plasmids pIT4 and pIT13 with BNPS-Skatole.

There is a Trp in the CRP'sequence at position 67 which is also found in the Tenchini et al. sequence (see Table 3). Cleavage at this site would produce a fragment of ~8006 Mr. As shown in FIG. 18A, digestion of the mCRP and of the pIT13 product produced a prominent fragment of this size, whereas digestion of the pIT4 product produced a fragment of ~11,000 Mr, the expected size if Trp68 were absent. Since the pIT4 and pIT13 products were digested under identical conditions, these results strongly suggest that Trp68 is missing in the pIT4 product and that the out-of-frame sequence of pIT4 extends at least to codon 67.

In a second experiment, the two mutant rCRP's were digested with endoproteinase LysC (Boehringer Mannheim Biochemicals), which cleaves specifically at the C-terminal side of lysine residues. The purified mutant rCRP's (prepared as described above, this section) were solubilized in 8 M urea, 25 mM Tris-Cl, pH 8.0, at a concentration of 5 mg/ml. Then, 0.1 M Tris-Cl, pH 7.4, enzyme and water were added in sufficient quantities to give final conditions of 25 mM Tris-Cl, pH 7.4, 4 M urea, 0.05 U enzyme, and 2.5 mg/ml protein. The digests were incubated for 24 hours at room temperature, and the digestion products were analyzed by SDS-PAGE as described in section G above, except that high density gels designed for peptide separations were used.

Figure 18B:
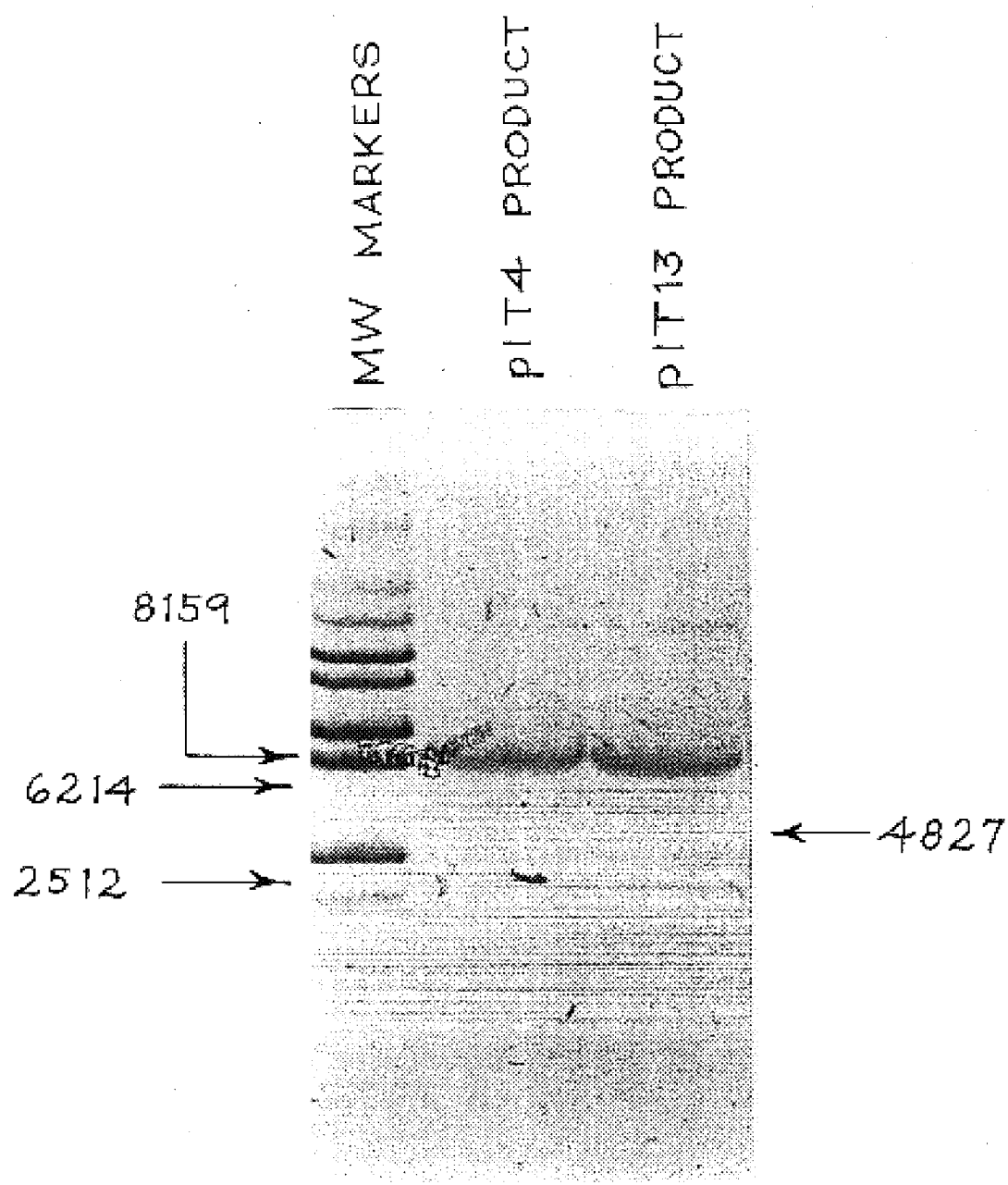
FIG. 18B is an SDS-PAGE gel obtained by. electrophoresing the digests produced by treating the mutant proteins produced by plasmids pIT4 and pIT13 with endoproteinase Lys C.

The results are shown in FIG. 18B. In the region of the protein sequence in question, digestion of the pIT13 product with LysC would be expected to yield fragments of Mr 2961 (residues 32–57), 1548 (residues 58–69) and 4827 (residues 70–114). In the pIT4 product, the lysine at position 57 is predicted to be absent, and a novel lysine present at position 59 (see Table 3). If the lysine at position 69 is present in this protein, digestion with LysC should produce fragments of Mr ~3200 (residues 32–59), ~1100 (residues 60–69) and 4827 (residues 70–114). In contrast, if it is absent, the 4827 and ~1100 Mr fragments would be replaced by a fragment of ~6000 Mr. As shown in FIG. 18B, there is a fragment produced by digesting both the pIT4 and pIT13 proteins which migrates at ~4800 Mr and there is no trace of a ~6000 Mr fragment in the pIT4 protein digest. These results indicate that there is a lysine at position 69 in the mutant rCRP's produced by both pIT4 and pIT13.

Taken together with the original amino acid composition and DNA sequence data (see section F above), the results of these two experiments strongly suggest that the sequence of the full-length mutant rCRP produced by pIT4 has the following amino acid sequence from position 47 to position 69:

```
Arg Gly Thr Val Phe Ser Arg Met     (SEQ ID
                5                    NO:24)

Pro Pro Arg Asp Lys Thr Met Arg
    10                  15

Phe Ser Tyr Phe Gly Leu Lys
            20
```

Residues shown in bold are those that likely differ from the bona fide CRP sequence and from the Tenchini et al. sequence (see Table 3 above). Those residues which are underlined are still questionable in terms of their identity.

The results in section E which show that the mutant rCRP produced by pIT4 binds aggregated IgG and the above results giving the likely amino acid sequence of this mutant rCRP from position 47 to position 69 show that the identity of the amino acids in this region, particularly from position 49 to position 68, is not critical for the binding of aggregated IgG and immune complexes. Accordingly, mutant rCRP's having amino acids in this region deleted or substituted or having amino acids added to this region can be prepared (by culturing host cells transformed with DNA coding for them), and such mutant rCRP's should bind aggregated immunoglobulin or immune complexes as do the products of pIT4 and pIT13.

We claim:

1. A mutant mammalian C-reactive protein (CRP) subunit selected from the group consisting of a subunit:
    (i) having at least one cysteine deleted or replaced as compared to SEQ ID NO: 27,
    (ii) having at least one amino acid of amino acids of SEQ ID NO: 27 deleted or replaced between positions 43–57 of said, SEQ ID NO: 27,
    (iii) having a combination of such changes and wherein said subunit also reacts with an antibody specific for neo-CRP antigenicity.

2. The protein subunit of claim 1 wherein at least one of the cysteines has been replaced by an amino acid selected from the group consisting of glycine, alanine, valine, leucine, isoleucine, serine, threonine or methionine.

3. The mutant protein of claim 2 wherein at least one of the cysteines has been replaced by an alanine.

4. The mutant protein of claim 3 wherein all of the cysteines have been replaced by alanines.

5. A mutant human C-reactive protein (CRP) subunit selected from the group consisting of a subunit:
    (i) having at least one cysteine deleted or replaced as compared to SEQ ID NO: 27,
    (ii) having at least one amino acid of the following sequence of) SEQ ID NO: 27 deleted or replaced between positions 43–57 of said SEQ ID NO: 27,
    (iii) having a combination of such changes; said subunit also reacting with an antibody specific for neo-CRP antigenicity.

6. The mutant protein of claim 5 where at least one of the cysteines has been replaced by an amino acid selected from the group consisting of glycine, alanine, valine, leucine, isoleucine, serine, threonine or methionine.

7. The mutant protein of claim 6 wherein at least one of the cysteines has been replaced by an alanine.

8. The mutant protein of claim 7 wherein all of the cysteines have been replaced by alanines.

9. The protein subunit of claim 5 wherein all of the amino acids in the sequence portion SEQ ID NO: 26 have been substituted to give the following sequence:

```
Thr Val Phe Ser Arg Met Pro Pro        SEQ ID NO:26
              5

Arg Asp Lys Thr Met Arg Phe Ser
 10                      15

Tyr Phe Gly Leu
         20.
```

10. A mutant mammalian C-reactive protein (CRP) subunit selected from the group consisting of a subunit:
    (i) having at least one cysteine deleted or replaced as compared to SEQ ID NO: 27,
    (ii) having at least one amino acid of the amino acids of SEQ ID NO: 27 deleted or replaced between positions 43–57 of said SEQ ID NO: 27,
    (iii) having a combination of such changes; said subunit also reacting with an antibody specific for neo-CRP antigenicity.

11. The protein subunit of claim 10 wherein at leas one of the cysteines has been replaced by an amino acid selected from the group consisting of glycine, alanine, valine, leucine, isoleucine, serine, threonine or methionine.

12. The mutant protein of claim 11 wherein at least one of the cysteines has been replaced by an alanine.

13. The mutant protein of claim 12 wherein all of the cysteines have been replaced by alanines.

14. The mutant protein of claim 5 wherein at least one hydrophobic amino acid has been deleted or replaced by a charged amino acid other than lysine, a charged amino acid other than lysine has been added, or a combination of such changes has been made to increase the solubility of the mutant protein as compared to the unmutated CRP subunit.

15. A mutant human C-reactive protein (CRP) subunit selected from the group consisting of a subunit:
  (i) having at least one cysteine deleted or replaced as compared to SEQ ID NO: 27,
  (ii) having at least one amino acid of SEQ ID NO: 27 deleted or replaced between positions 43–57 of said SEQ ID NO: 27,
  (iii) having a combination of such changes; said subunit also reacting with an antibody specific for neo-CRP antigenicity.

16. The mutant protein of claim 15 wherein at least one of the cysteines has been replaced by an amino acid selected from the group consisting of glycine, alanine, valine, leucine, isoleucine, serine, threonine or methionine.

17. The mutant protein of claim 16 wherein at least one of the cysteines has been replaced by an alanine.

18. The mutant protein of claim 17 wherein all of the cysteines have been replaced by alanines.

19. A pharmaceutical composition comprising a mutant C-reactive protein (CRP) subunit selected from the group consisting of a subunit:
  (i) having at least one cysteine deleted or replaced as compared to SEQ ID NO: 27,
  (ii) having at least one amino acid of the amino acids of SEQ ID NO: 27 deleted or replaced between positions 43–57 of said SEQ ID NO: 27,
  (iii) having a combination of such changes; said subunit also reacting with an antibody specific for neo-CRP antigenicity.

20. The pharmaceutical composition of claim 19 wherein all of the cysteines have been deleted or replaced.

21. The pharmaceutical composition of claim 19 or 20 wherein at least one of the cysteines has been replaced by an amino acid selected from the group consisting of glycine, alanine, valine, leucine, isoleucine, serine, threonine or methionine.

22. The pharmaceutical composition of claim 21 wherein at least one of the cysteines has been replaced by an alanine.

23. The pharmaceutical composition of claim 22 wherein all of the cysteines have been replaced by alanines.

24. A pharmaceutical composition comprising a mutant C-reactive protein (CRP) subunit selected from the group consisting of a subunit:
  (i) having at least one cysteine deleted or replaced as compared to SEQ ID NO: 27,
  (ii) having at least one amino acid of SEQ ID NO: 27 deleted or replaced between positions 43–57 of said SEQ ID NO: 27,
  (iii) having a combination of such changes; said subunit also reacting with an antibody specific for neo-CRP antigenicity.

25. The pharmaceutical composition of claim 24 wherein all of the cysteines have been deleted or replaced.

26. A The pharmaceutical composition of claim 24 or 25 wherein at least one of the cysteines has been replaced by an amino acid selected from the group consisting of glycine, alanine, valine, leucine, isoleucine, serine, threonine or methionine.

27. The pharmaceutical composition of claim 26 wherein at least one of the cysteines has been replaced by an alanine.

28. The pharmaceutical composition of claim 27 wherein all of the cysteines have been replaced by alanines.

29. The pharmaceutical composition of claim 24 wherein at least one of the amino acids in SEQ ID NO: 25 is deleted or replaced:

```
Tyr Ser Ile Phe Ser Tyr Ala Thr      SEQ ID NO:25
            5
Lys Arg Gln Asp Asn Glu Ile Leu
 10                      15
Ile Phe Trp Ser
        20.
```

30. The pharmaceutical composition of claim 29 wherein all of the amino acids in the sequence portion SEQ ID NO: 25 have been substituted to give the following sequence:

```
Thr Val Phe Ser Arg Met Pro Pro      SEQ ID NO:26
            5
Arg Asp Lys Thr Met Arg Phe Ser
 10                      15
Tyr Phe Gly Leu
        20.
```

31. A pharmaceutical composition comprising a mutant C-reactive protein (CRP) subunit selected from the group consisting of a subunit:
  (i) having at least one cysteine deleted or replaced as compared to SEQ ID NO: 27,
  (ii) having at least one amino acid of the amino acids of SEQ ID NO: 27 deleted or replaced between positions 43–57 of said SEQ ID NO: 27,
  (iii) having a combination of such changes; and wherein said subunit also reacts with an antibody specific for neo-CRP antigenicity.

32. The pharmaceutical composition of claim 31 wherein all of the cysteines have been deleted or replaced.

33. The pharmaceutical composition of claim 31 or 32 wherein at least one of the cysteines has been replaced by an amino acid selected from the group consisting of glycine, alanine, valine, leucine, isoleucine, serine, threonine or methionine.

34. The pharmaceutical composition of claim 33 wherein at least one of the cysteines has been replaced by an alanine.

35. The pharmaceutical composition of claim 34 wherein all of the cysteines have been replaced by alanines.

36. A pharmaceutical composition comprising a mutant C-reactive protein (CRP) subunit selected from the group consisting of a subunit:
  (i) having at least one cysteine deleted or replaced as compared to SEQ ID NO: 27,
  (ii) having at least one amino acid of SEQ ID NO: 27 deleted or replaced between positions 43–57 of said SEQ ID NO: 27,
  (iii) having a combination of such changes; and wherein said subunit also reacts with an antibody specific for neo-CRP antigenicity.

37. The pharmaceutical composition of claim 36 wherein all of the cysteines have been deleted or replaced.

38. The pharmaceutical composition of claim 36 or 37 wherein at least one of the cysteines has been replaced by an amino acid selected from the group consisting of glycine, alanine, valine, leucine, isoleucine, serine, threonine or methionine.

39. The pharmaceutical composition of claim 38 wherein at least one of the cysteines has been replaced by an alanine.

40. The pharmaceutical composition of claim 39 wherein all of the cysteihes have been replaced by alanines.

41. The pharmaceutical composition of claim 36 wherein at leas one the amino acids in SEQ ID NO: 25 is deleted or replaced:

```
Tyr Ser Ile Phe Ser Tyr Ala Thr      SEQ ID NO:25
              5
Lys Arg Gln Asp Asn Glu IIe Leu
     10                  15
Ile Phe Trp Ser
             20.
```

42. The pharmaceutical composition of claim 41 wherein all of the amino acids in the sequence portion SEQ ID NO: 25 have been substituted to give the following sequence:

```
Thr Val Phe Ser Arg Met Pro Pro      SEQ ID NO:26
              5
Arg Asp Lys Thr Met Arg Phe Ser
     10                  15
Tyr Phe Gly Leu
             20.
```

43. A mutant mammalian C-reactive protein (CRP) subunit or preCRP which has all of the cysteines deleted or replaced by another amino acid.

* * * * *

SEQUENCE LISTING

```
<160> NUMBER OF SEQ ID NOS: 27

<210> SEQ ID NO 1
<211> LENGTH: 28
<212> TYPE: DNA
<213> ORGANISM: Artificial sequence
<220> FEATURE:
<223> OTHER INFORMATION: primer
<220> FEATURE:
<221> NAME/KEY: exon
<222> LOCATION: (8)..(28)
<223> OTHER INFORMATION:

<400> SEQUENCE: 1 gggccat atg cag aca gac atg tcg agg                                    28
        Met Gln Thr Asp Met Ser Arg
        1               5

<210> SEQ ID NO 2
<211> LENGTH: 20
<212> TYPE: DNA
<213> ORGANISM: Artificial sequence
```

```
<220> FEATURE:
<223> OTHER INFORMATION: primer

<400> SEQUENCE: 2
gaagcgccac agtgaaggct                                             20

<210> SEQ ID NO 3
<211> LENGTH: 16
<212> TYPE: DNA
<213> ORGANISM: Artificial sequence
<220> FEATURE:
<223> OTHER INFORMATION: primer
<220> FEATURE:
<221> NAME/KEY: exon
<222> LOCATION: (2)..(16)
<223> OTHER INFORMATION:

<400> SEQUENCE: 3 c act gtg gcg ctc cac                                             16
  Thr Val Ala Leu His
  1               5

<210> SEQ ID NO 4
<211> LENGTH: 19
<212> TYPE: DNA
<213> ORGANISM: Artificial sequence
<220> FEATURE:
<223> OTHER INFORMATION: primer

<400> SEQUENCE: 4
ttgtcgcgat gtgtactgg                                              19

<210> SEQ ID NO 5
<211> LENGTH: 17
<212> TYPE: DNA
<213> ORGANISM: Artificial sequence
<220> FEATURE:
<223> OTHER INFORMATION: primer
<220> FEATURE:
<221> NAME/KEY: exon
<222> LOCATION: (1)..(16)
<223> OTHER INFORMATION:

<400> SEQUENCE: 5 cac atc gcg aca agc t g                                           17
His Ile Ala Thr Ser
1               5

<210> SEQ ID NO 6
<211> LENGTH: 24
<212> TYPE: DNA
<213> ORGANISM: Artificial sequence
<220> FEATURE:
<223> OTHER INFORMATION: primer

<400> SEQUENCE: 6
ggcgagatct gaggtacctt cagg                                        24

<210> SEQ ID NO 7
<211> LENGTH: 12
<212> TYPE: DNA
<213> ORGANISM: Homo sapiens
<220> FEATURE:
<221> NAME/KEY: exon
<222> LOCATION: (1)..(12)
<223> OTHER INFORMATION:

<400> SEQUENCE: 7
```

```
ttt ggc cag aca                                                    12
Phe Gly Gln Thr
  1

<210> SEQ ID NO 8
<211> LENGTH: 15
<212> TYPE: DNA
<213> ORGANISM: bacteriophage phi-10
<220> FEATURE:
<221> NAME/KEY: exon
<222> LOCATION: (4)..(15)
<223> OTHER INFORMATION:

<400> SEQUENCE: 8 cat atg gct agc atg                                                15
    Met Ala Ser Met
      1

<210> SEQ ID NO 9
<211> LENGTH: 21
<212> TYPE: DNA
<213> ORGANISM: Homo sapiens
<220> FEATURE:
<221> NAME/KEY: exon
<222> LOCATION: (1)..(21)
<223> OTHER INFORMATION:

<400> SEQUENCE: 9 gct ttt ggc cag aca gac atg                                        21
Ala Phe Gly Gln Thr Asp Met
  1               5

<210> SEQ ID NO 10
<211> LENGTH: 24
<212> TYPE: DNA
<213> ORGANISM: Artificial sequence
<220> FEATURE:
<223> OTHER INFORMATION: mutant
<220> FEATURE:
<221> NAME/KEY: exon
<222> LOCATION: (4)..(24)
<223> OTHER INFORMATION:

<400> SEQUENCE: 10 cat atg gct agc cag aca gac atg                                    24
    Met Ala Ser Gln Thr Asp Met
      1               5

<210> SEQ ID NO 11
<211> LENGTH: 10
<212> TYPE: PRT
<213> ORGANISM: Homo sapiens

<400> SEQUENCE: 11

Leu Ser Ser Thr Arg Gly Tyr Ser Ile Phe
  1               5                  10

<210> SEQ ID NO 12
<211> LENGTH: 7
<212> TYPE: PRT
<213> ORGANISM: Artificial sequence
<220> FEATURE:
<223> OTHER INFORMATION: mutant

<400> SEQUENCE: 12

Ser Tyr Phe Gly Leu Arg Ile
  1               5
```

<210> SEQ ID NO 13
<211> LENGTH: 27
<212> TYPE: PRT
<213> ORGANISM: Homo sapiens

<400> SEQUENCE: 13

Thr Arg Gly Tyr Ser Ile Phe Ser Tyr Ala Thr Lys Arg Gln Asp Asn
1               5                   10                  15
Glu Ile Leu Ile Phe Trp Ser Lys Asp Ile Gly
            20                  25

<210> SEQ ID NO 14
<211> LENGTH: 81
<212> TYPE: DNA
<213> ORGANISM: Homo sapiens
<220> FEATURE:
<221> NAME/KEY: exon
<222> LOCATION: (1)..(81)
<223> OTHER INFORMATION:

<400> SEQUENCE: 14 acc cgt ggg tac agt att ttc tcg tat gcc acc aag aga caa gac aat       48
Thr Arg Gly Tyr Ser Ile Phe Ser Tyr Ala Thr Lys Arg Gln Asp Asn
1               5                   10                  15 gag att ctc ata ttt tgg tct aag gat ata gga                           81
Glu Ile Leu Ile Phe Trp Ser Lys Asp Ile Gly
            20                  25

<210> SEQ ID NO 15
<211> LENGTH: 25
<212> TYPE: PRT
<213> ORGANISM: Artificial sequence
<220> FEATURE:
<223> OTHER INFORMATION: mutant

<400> SEQUENCE: 15

Thr Arg Gly Thr Val Phe Ser Arg Met Pro Pro Arg Asp Lys Thr Met
1               5                   10                  15
Arg Phe Ser Tyr Phe Gly Leu Arg Ile
            20                  25

<210> SEQ ID NO 16
<211> LENGTH: 80
<212> TYPE: DNA
<213> ORGANISM: Artificial sequence
<220> FEATURE:
<223> OTHER INFORMATION: mutant
<220> FEATURE:
<221> NAME/KEY: exon
<222> LOCATION: (1)..(75)
<223> OTHER INFORMATION:

<400> SEQUENCE: 16 acc cgg ggt aca gta ttt tct cgt atg cca cca aga gac aag aca atg       48
Thr Arg Gly Thr Val Phe Ser Arg Met Pro Pro Arg Asp Lys Thr Met
1               5                   10                  15 aga ttc tca tat ttt ggt cta agg ata tagga                             80
Arg Phe Ser Tyr Phe Gly Leu Arg Ile
            20                  25

<210> SEQ ID NO 17
<211> LENGTH: 27
<212> TYPE: PRT
<213> ORGANISM: Homo sapiens

<400> SEQUENCE: 17

Thr Arg Gly Thr Val Phe Ser Arg Met Pro Pro Arg Asp Lys Thr Met
1               5                   10                  15

```
Arg Phe Phe Ile Phe Trp Ser Lys Asp Ile Gly
            20                  25
```

<210> SEQ ID NO 18
<211> LENGTH: 81
<212> TYPE: DNA
<213> ORGANISM: Homo sapiens
<220> FEATURE:
<221> NAME/KEY: exon
<222> LOCATION: (1)..(81)
<223> OTHER INFORMATION:

<400> SEQUENCE: 18

```
acc cgg ggt aca gta ttt tct cgt atg cca cca aga gac aag aca atg      48
Thr Arg Gly Thr Val Phe Ser Arg Met Pro Pro Arg Asp Lys Thr Met
1               5                   10                  15 aga ttc ttc ata ttt tgg tct aag gat ata gga                          81
Arg Phe Phe Ile Phe Trp Ser Lys Asp Ile Gly
            20                  25
```

<210> SEQ ID NO 19
<211> LENGTH: 28
<212> TYPE: DNA
<213> ORGANISM: Homo sapiens
<220> FEATURE:
<221> NAME/KEY: exon
<222> LOCATION: (3)..(26)
<223> OTHER INFORMATION:

<400> SEQUENCE: 19

```
cc tcg acc cgg ggt aca gta ttt tct cg                                28
   Ser Thr Arg Gly Thr Val Phe Ser
   1               5
```

<210> SEQ ID NO 20
<211> LENGTH: 29
<212> TYPE: DNA
<213> ORGANISM: Artificial sequence
<220> FEATURE:
<223> OTHER INFORMATION: primer
<220> FEATURE:
<221> NAME/KEY: exon
<222> LOCATION: (3)..(29)
<223> OTHER INFORMATION:

<400> SEQUENCE: 20

```
cc tcg acc cgt ggt tac agc att ttc tcg                               29
   Ser Thr Arg Gly Tyr Ser Ile Phe Ser
   1               5
```

<210> SEQ ID NO 21
<211> LENGTH: 25
<212> TYPE: DNA
<213> ORGANISM: Artificial sequence
<220> FEATURE:
<223> OTHER INFORMATION: primer

<400> SEQUENCE: 21

```
cccgcgaaat taatacgact cacta                                          25
```

<210> SEQ ID NO 22
<211> LENGTH: 29
<212> TYPE: DNA
<213> ORGANISM: Artificial sequence
<220> FEATURE:
<223> OTHER INFORMATION: primer

<400> SEQUENCE: 22

```
cgagaaaatg ctgtaaccac gggtcgagg                                         29
```

<210> SEQ ID NO 23
<211> LENGTH: 26
<212> TYPE: DNA
<213> ORGANISM: Artificial sequence
<220> FEATURE:
<223> OTHER INFORMATION: primer
<400> SEQUENCE: 23

```
ctttgttagc agccggatcc gaggta                                            26
```

<210> SEQ ID NO 24
<211> LENGTH: 23
<212> TYPE: PRT
<213> ORGANISM: Artificial sequence
<220> FEATURE:
<223> OTHER INFORMATION: mutant
<400> SEQUENCE: 24

```
Arg Gly Thr Val Phe Ser Arg Met Pro Pro Asp Lys Thr Met Arg
1               5                  10                  15

Phe Ser Tyr Phe Gly Leu Lys
            20
```

<210> SEQ ID NO 25
<211> LENGTH: 20
<212> TYPE: PRT
<213> ORGANISM: Homo sapiens
<400> SEQUENCE: 25

```
Tyr Ser Ile Phe Ser Tyr Ala Thr Lys Arg Gln Asp Asn Glu Ile Leu
1               5                   10                  15

Ile Phe Trp Ser
            20
```

<210> SEQ ID NO 26
<211> LENGTH: 20
<212> TYPE: PRT
<213> ORGANISM: Artificial sequence
<220> FEATURE:
<223> OTHER INFORMATION: mutant
<400> SEQUENCE: 26

```
Thr Val Phe Ser Arg Met Pro Pro Arg Asp Lys Thr Met Arg Phe Ser
1               5                   10                  15

Tyr Phe Gly Leu
            20
```

<210> SEQ ID NO 27
<211> LENGTH: 224
<212> TYPE: PRT
<213> ORGANISM: Homo sapiens
<400> SEQUENCE: 27

```
Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
                20                  25                  30

Ser Asp Thr Ser Tyr Val Ser Leu Lys Ala Pro Leu Thr Lys Pro Leu
            35                  40                  45

Lys Ala Phe Thr Val Cys Leu His Phe Tyr Thr Glu Leu Ser Ser Thr
```

-continued

```
                        50                      55                      60
Arg Gly Tyr Ser Ile Phe Ser Tyr Ala Thr Lys Arg Gln Asp Asn Glu
 65                      70                      75                      80

Ile Leu Ile Phe Trp Ser Lys Asp Ile Gly Tyr Ser Phe Thr Val Gly
                         85                      90                      95

Gly Ser Glu Ile Leu Phe Glu Val Pro Glu Val Thr Val Ala Pro Val
                    100                     105                     110

His Ile Cys Thr Ser Trp Glu Ser Ala Ser Gly Ile Val Glu Phe Trp
            115                     120                     125

Val Asp Gly Lys Pro Arg Val Arg Lys Ser Leu Lys Lys Gly Tyr Thr
    130                     135                     140

Val Gly Ala Glu Ala Ser Ile Ile Leu Gly Gln Glu Gln Asp Ser Phe
145                     150                     155                     160

Gly Gly Asn Phe Glu Gly Ser Gln Ser Leu Val Gly Asp Ile Gly Asn
                165                     170                     175

Val Asn Met Trp Asp Phe Val Leu Ser Pro Asp Glu Ile Asn Thr Ile
                180                     185                     190

Tyr Leu Gly Gly Pro Phe Ser Pro Asn Val Leu Asn Trp Arg Ala Leu
        195                     200                     205

Lys Tyr Glu Val Gln Gly Glu Val Phe Thr Lys Pro Gln Leu Trp Pro
    210                     215                     220
```